(12) United States Patent  
Otsuki et al.

(10) Patent No.: US 7,667,840 B2
(45) Date of Patent: Feb. 23, 2010

(54) PARTICLE-MEASURING SYSTEM AND PARTICLE-MEASURING METHOD

(75) Inventors: Hayashi Otsuki, Nakakoma-gun (JP); Tsukasa Matsuda, Kitakoma-gun (JP); Kyoko Ikeda, Kofu (JP)

(73) Assignee: Tokyo Electron Limited, Tokyo (JP)

( * ) Notice: Subject to any disclaimer, the term of this patent is extended or adjusted under 35 U.S.C. 154(b) by 187 days.

(21) Appl. No.: 11/965,357

(22) Filed: Dec. 27, 2007

(65) Prior Publication Data

US 2008/0264338 A1 Oct. 30, 2008

Related U.S. Application Data

(60) Division of application No. 10/321,646, filed on Dec. 18, 2002, now Pat. No. 7,515,264, which is a continuation-in-part of application No. 09/594,479, filed on Jun. 14, 2000, now Pat. No. 6,532,069.

(30) Foreign Application Priority Data

Jun. 15, 1999 (JP) .................................. 11-168968
Dec. 25, 2001 (JP) .............................. 2001-392703

(51) Int. Cl.
*G01N 21/00* (2006.01)

(52) U.S. Cl. ........................ 356/338; 356/339
(58) Field of Classification Search .......... 356/338–339
See application file for complete search history.

(56) References Cited

U.S. PATENT DOCUMENTS 3,770,351 A * 11/1973 Wyatt ......................... 356/336

5,271,264 A   12/1993   Chanayem
5,347,138 A    9/1994   Aqui et al.

(Continued)

FOREIGN PATENT DOCUMENTS

| JP | 6 110870 | 4/1994 |
| JP | 7 263523 | 10/1995 |
| JP | 10-10036 | 1/1998 |

(Continued)

OTHER PUBLICATIONS

Tom Winter, et al., "ISPM Characterization of Gas Phase Nucleation in a Novellus C1 WCVD Process Chamber," IEEE/SEMI Advanced Semiconductor Manufacturing Conference, 1995, pps. 17-22.
Jenny Asbell, et al., "Improving Tungsten CVD Performance With In Situ Particle Monitoring," Micro, Jul./Aug. 1997, pp. 63-73.

*Primary Examiner*—Tarifur Chowdhury
*Assistant Examiner*—Tara S Pajoohi
(74) *Attorney, Agent, or Firm*—Oblon, Spivak, McClelland, Maier & Neustadt, L.L.P.

(57) ABSTRACT

The present invention provides a particle measuring system which is provided in a processing system that generates an atmosphere obtained by exhausting air or a gas in a processing chamber by a vacuum pump and applies a process concerning semiconductor manufacture to a wafer W in the atmosphere, attached to an exhaust pipe which connects an exhaust opening of the processing chamber with the vacuum pump, and measures the number of the particles in the exhaust gas, and a measuring method thereof, the system and method providing a processing system and a cleaning method which terminate etching process by determining an end point based on the number of the particles in the exhaust gas and perform cleaning of unnecessary films.

36 Claims, 32 Drawing Sheets

U.S. PATENT DOCUMENTS

| | | |
|---|---|---|
| 5,438,526 A | 8/1995 | Itoh et al. |
| 5,501,113 A | 3/1996 | Harrison et al. |
| 5,681,752 A | 10/1997 | Prather |
| 5,719,666 A | 2/1998 | Fukuda et al. |
| 5,820,685 A | 10/1998 | Kurihara et al. |
| 5,837,094 A | 11/1998 | Tsukazaki et al. |
| 5,870,189 A | 2/1999 | Uesugi et al. |
| 5,907,399 A | 5/1999 | Shirasawa et al. |
| 6,269,981 B1 | 8/2001 | Nielsen |

FOREIGN PATENT DOCUMENTS

| | | |
|---|---|---|
| JP | 10-106974 | 4/1998 |
| JP | 10 242060 | 9/1998 |
| JP | 11-097386 | 4/1999 |
| JP | 2000-277459 | 10/2000 |
| JP | 2003-142425 | 5/2003 |
| JP | 2004-225162 | 8/2004 |
| KR | 1998-032091 | 7/1998 |

* cited by examiner

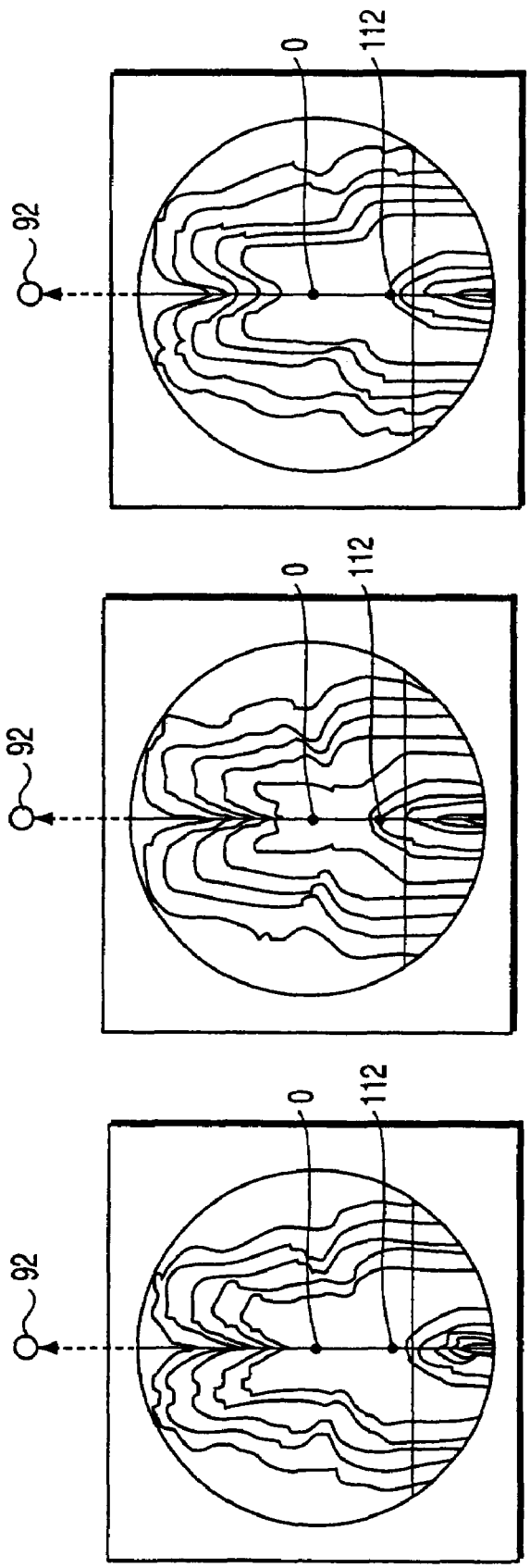

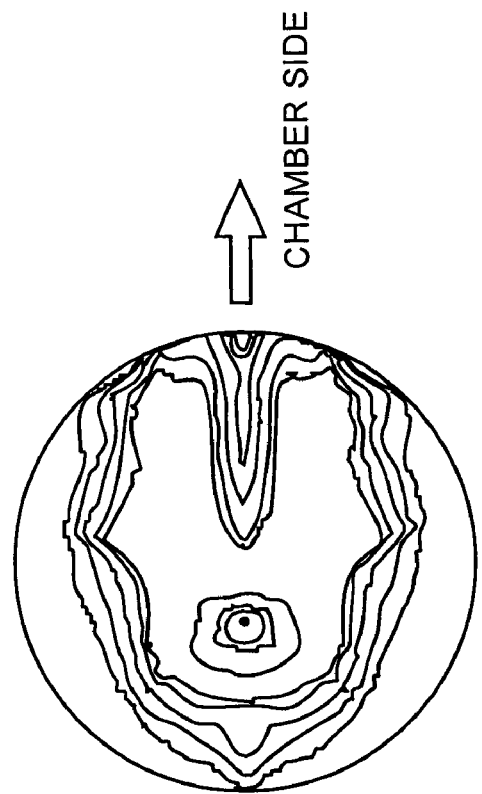
F I G. 15
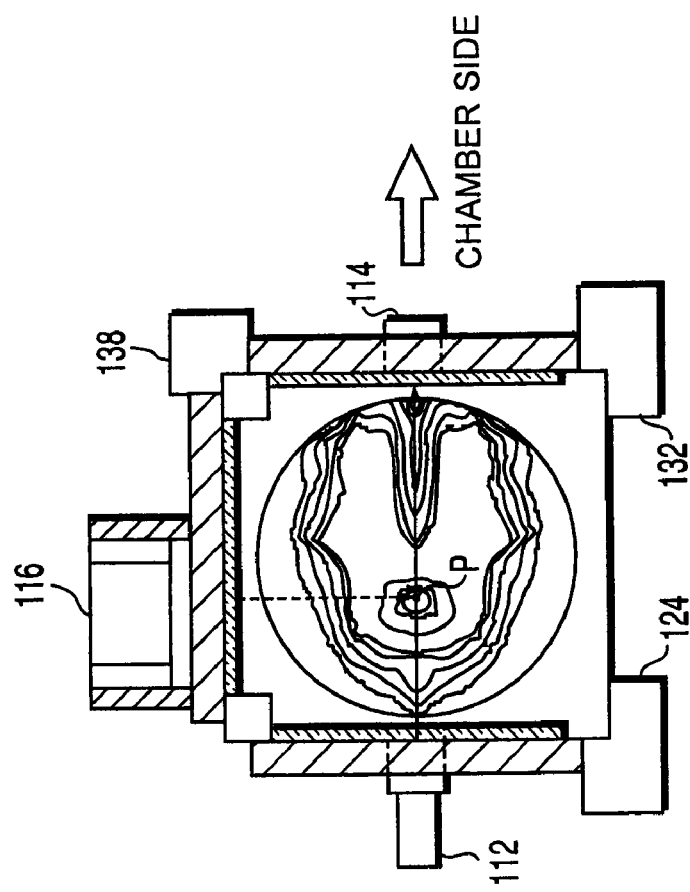
F I G. 16

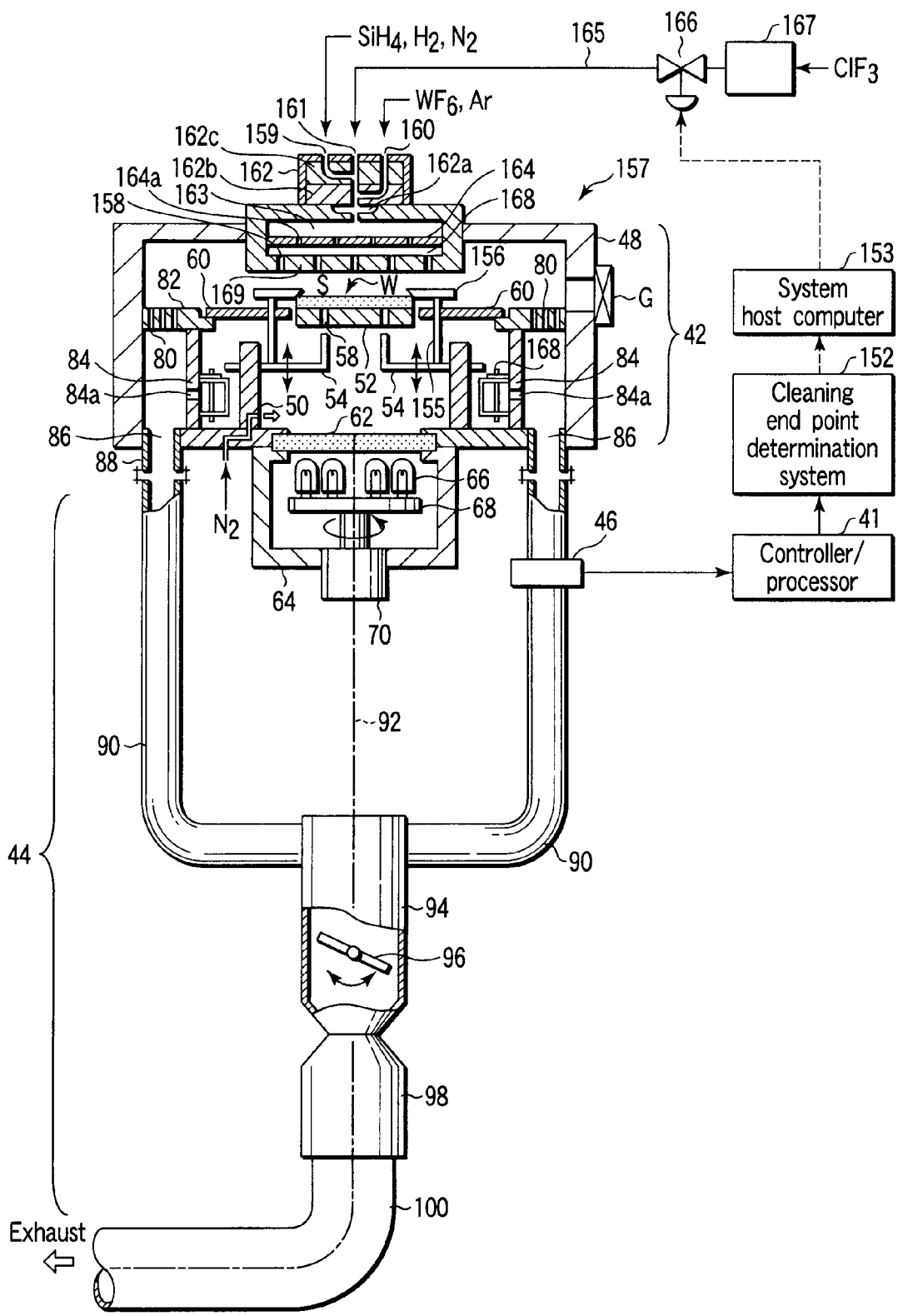
F I G. 20

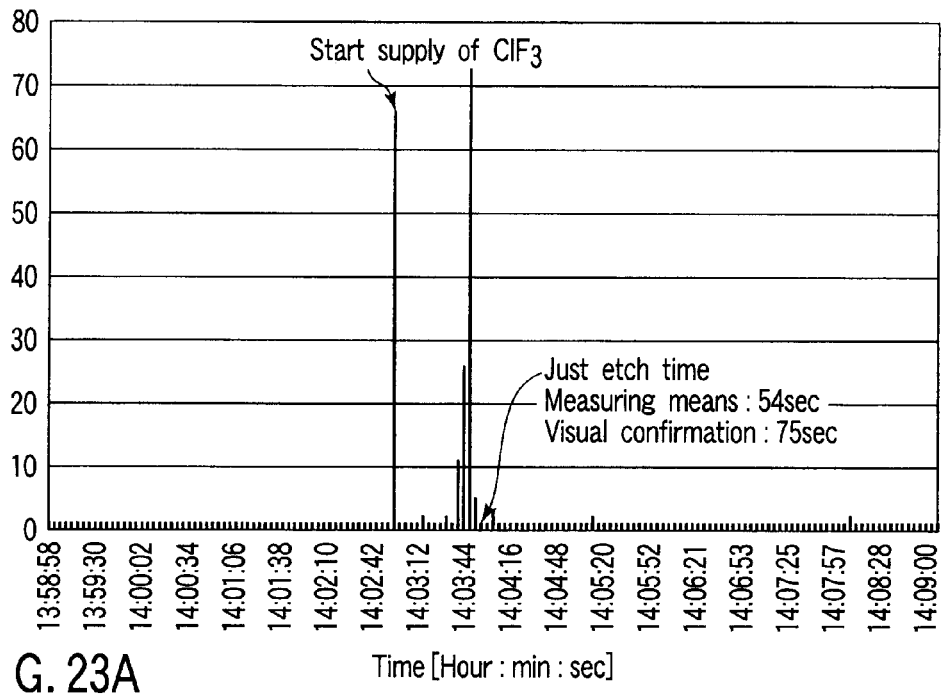
F I G. 23A
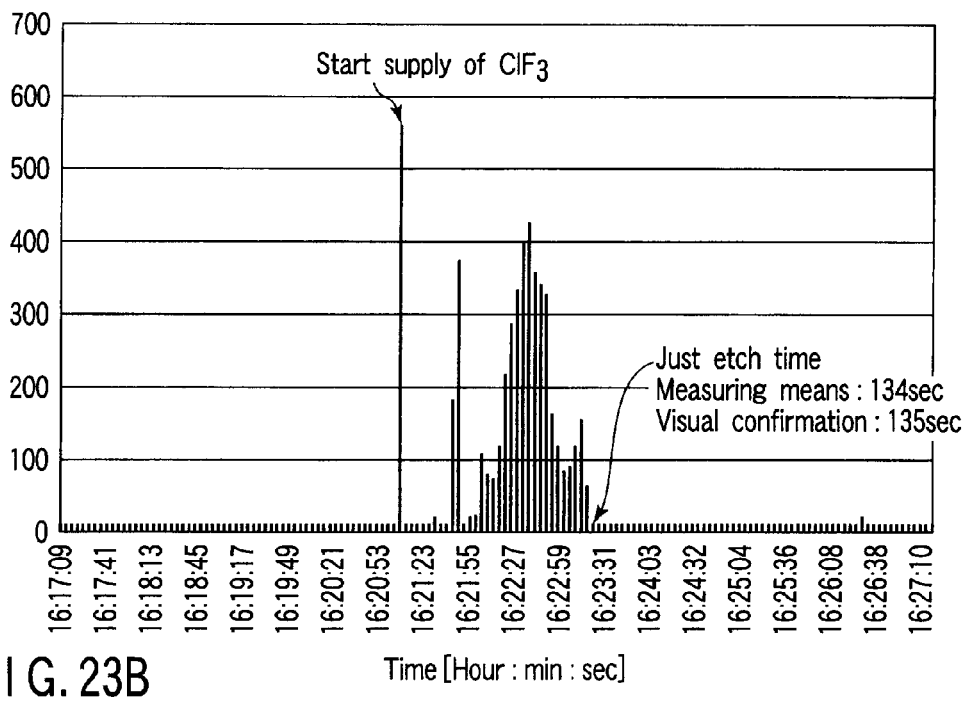
F I G. 23B

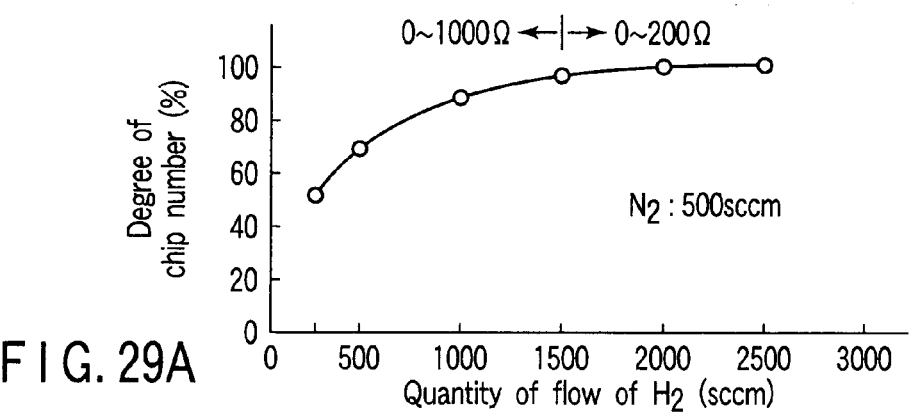
F I G. 29A
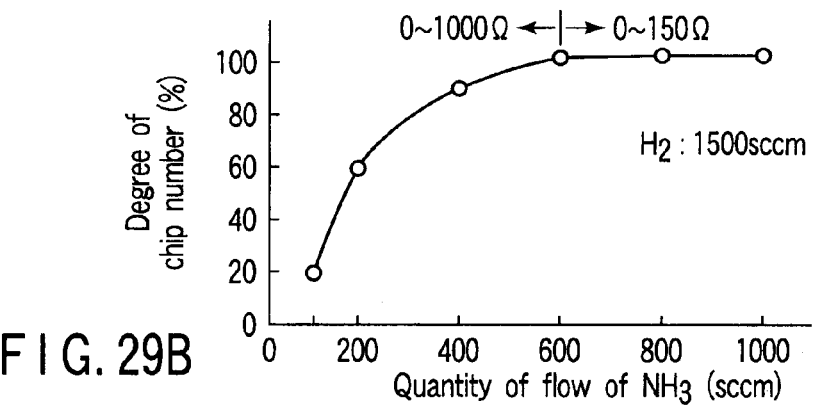
F I G. 29B
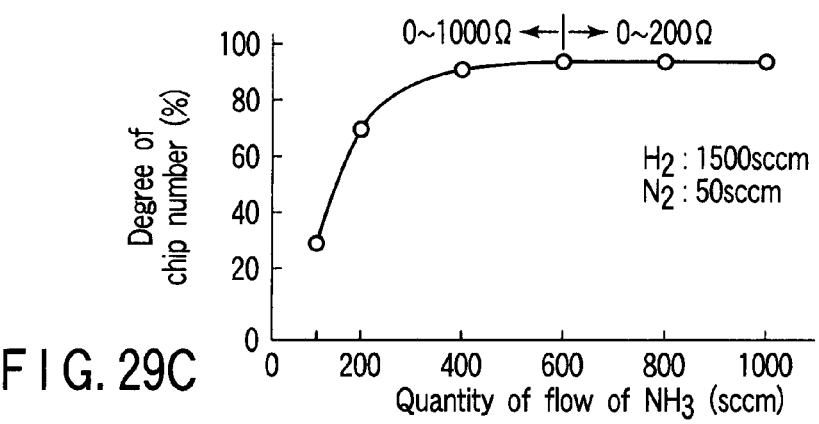
F I G. 29C
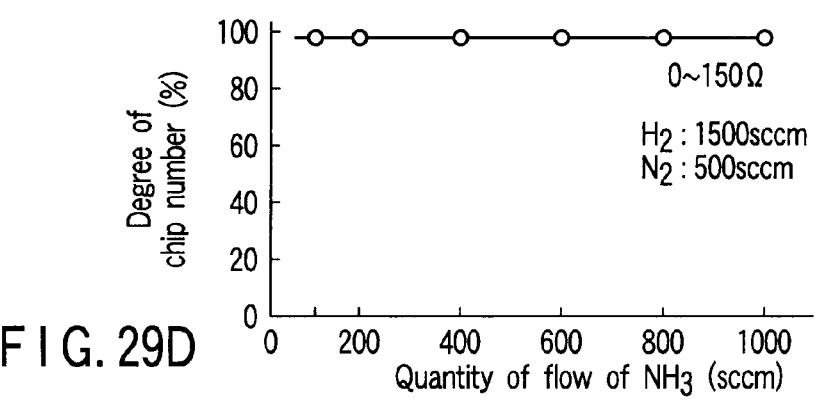
F I G. 29D

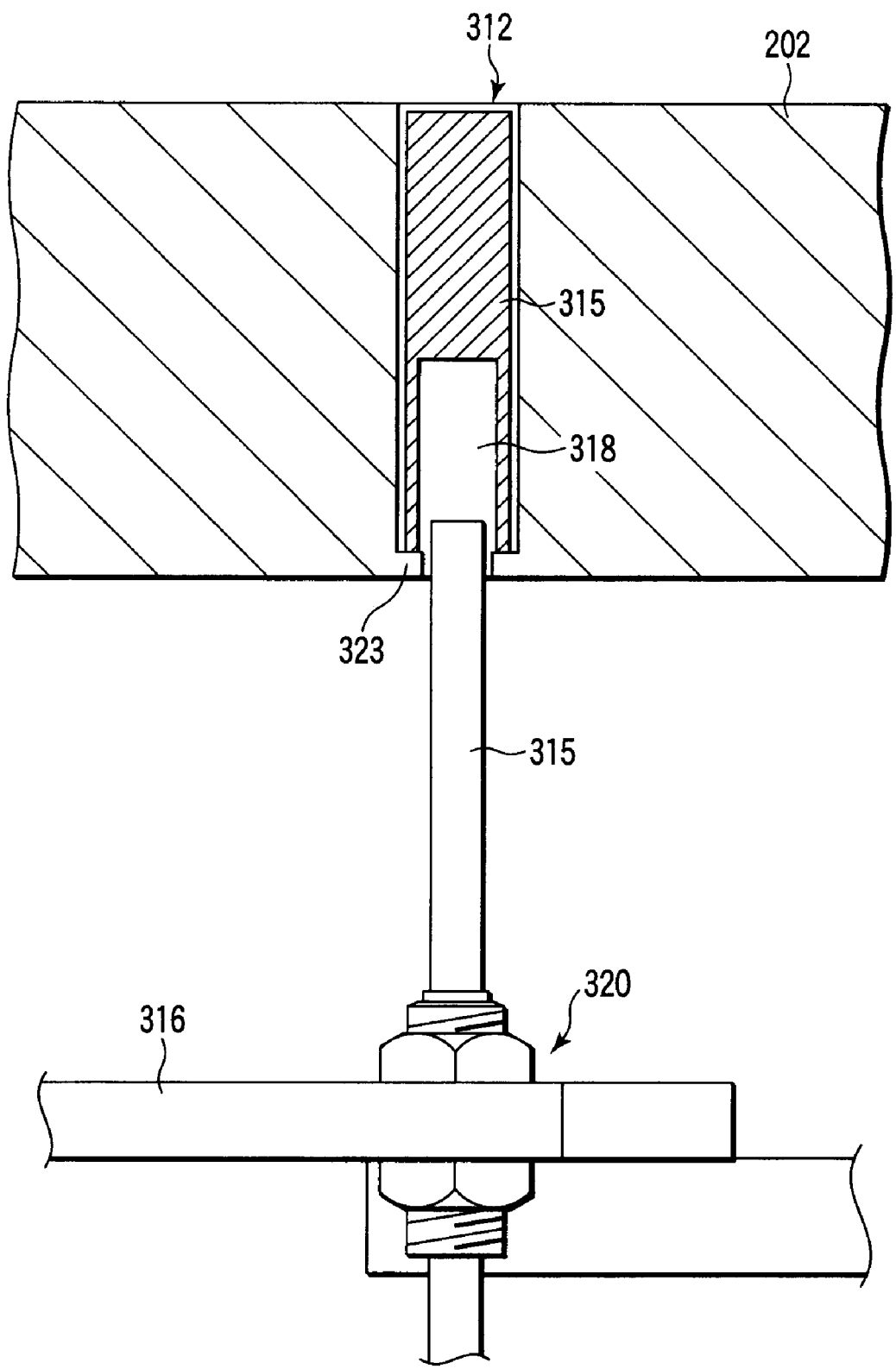
F I G. 34

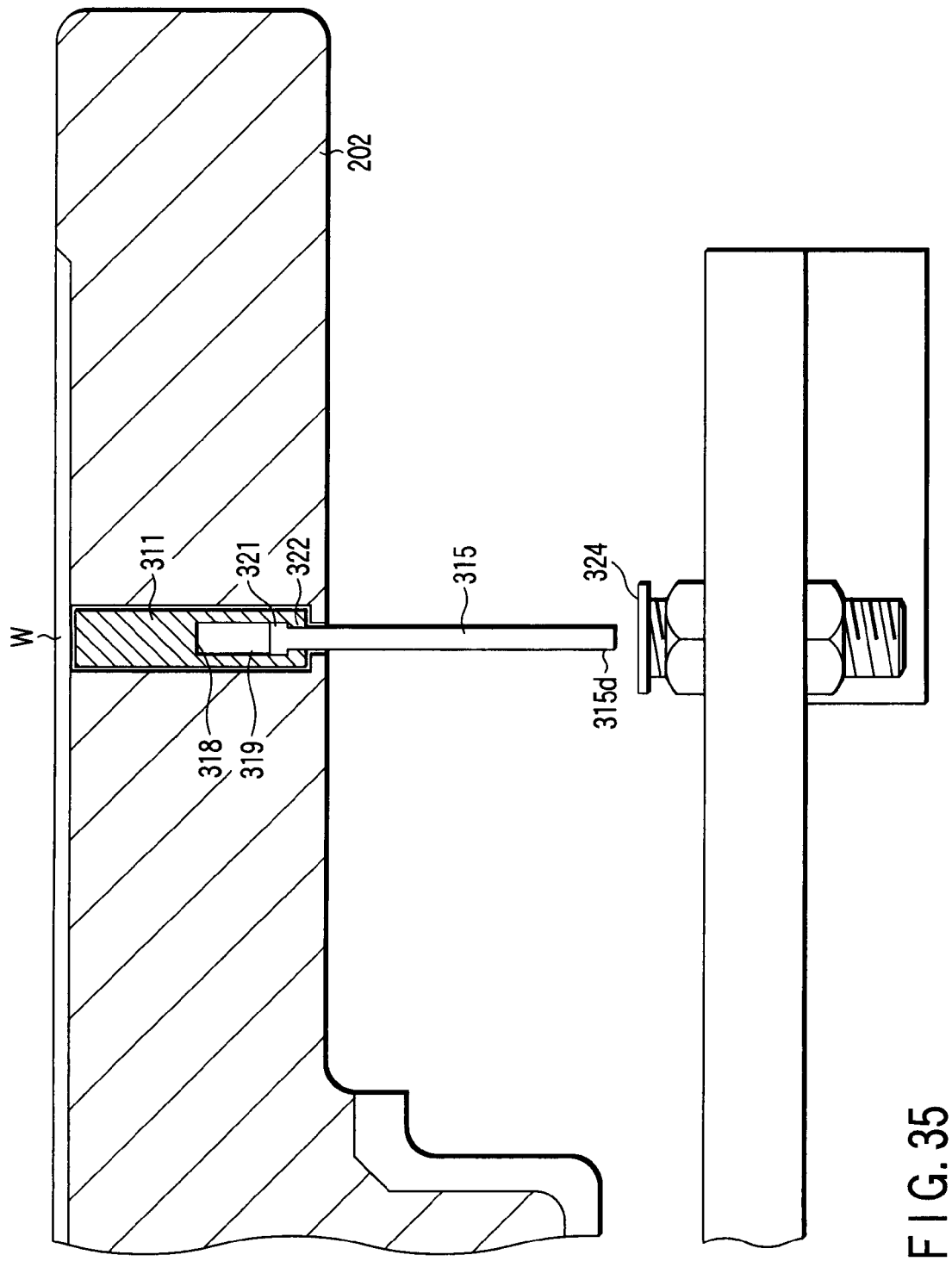
F I G. 35

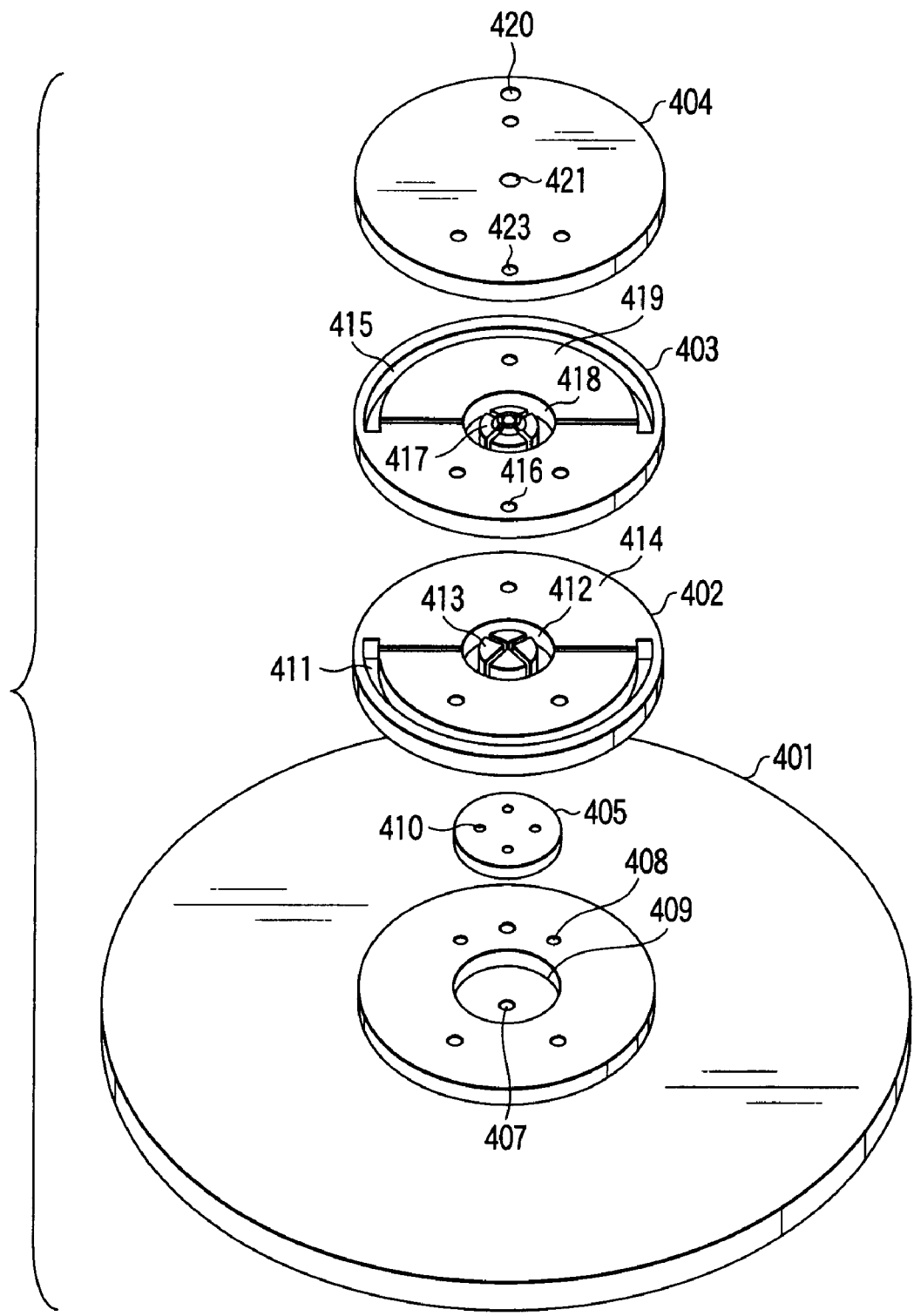
F I G. 36

US 7,667,840 B2

PARTICLE-MEASURING SYSTEM AND PARTICLE-MEASURING METHOD

CROSS-REFERENCE TO RELATED APPLICATIONS

The present divisional application claims the benefit of priority under 35 U.S.C. §120 to application Ser. No. 10/321,646, filed on Dec. 18, 2002, which is a Continuation-in-part application of U.S. patent application Ser. No. 09/594,479, filed Jun. 14, 2000. Application Ser. Nos. 10/321,646 and 09/594,479 are incorporated herein by reference. The present divisional application also claims the benefit of priority under 35 U.S.C. §119 from Japanese Patent Applications Nos. 11-168968, filed Jun. 15, 1999, and 2001-392703 filed on Dec. 25, 2001, the entire contents of both of which are incorporated herein by reference.

BACKGROUND OF THE INVENTION

The present invention relates to a particle-measuring system that is mounted on a processing unit for forming a film on a semiconductor wafer by using a gas, and that measures the number of particles included in an exhaust gas discharged from the processing unit.

Generally, in the manufacturing of semiconductor integrated circuits, various kinds of processing units are used for processing semiconductor wafers (hereinafter to be referred to as wafers) as objects to be processed at various manufacturing stages, including a film deposition (CVD: chemical vapor deposition) process, thermal oxidation and impurity diffusion processes, an etching process, a film forming (sputtering) process, a thermal processing process, etc.

In the film forming process, thin films such as a silicon oxide ($SiO_2$) film, a silicon nitride (SiN) film, and the like are deposited as insulation layers or insulation films on the surface of the wafer using, for example, a CVD unit. For forming wiring patterns and embedding trenches, thin films of tungsten (W), tungsten silicide (WSi), titanium (Ti), titanium nitride (TiN), titanium silicide (TiSi), etc. are deposited.

When these processing systems are used to carry out each processing, it is necessary to avoid as far as possible the generation of particles that become the cause of reduction in product yield.

Therefore, a particle-measuring system is installed on the processing system in order to real-time monitor the state of generation of particles within a processing chamber or in order to know the timing for cleaning the processing chamber. Particularly, in the film-forming system such as a CVD system or a sputtering system, there occurs an adhesion of unnecessary films onto the inner wall of the processing chamber or onto the surface of the parts. These unnecessary films are disposed and accumulated within the chamber during the film-forming process. These unnecessary films are easily peeled off at the next film-forming cycle, and particles are easily generated. Therefore, it has been important to monitor the volume of particles generated during the film-forming process.

One example of a processing system having a conventional particle-measuring system will be explained with reference to FIG. 18.

A mounting table 4 for mounting a wafer W is provided inside a processing chamber 2 of almost a cylindrical shape, and a transmission window 6 made of quartz glass is disposed on the bottom of the chamber. A plurality of heating lamps 10 are disposed on a rotary table 8 below the transmission window 6. Heating beams irradiated from these heating lamps 10 are transmitted through the transmission window 6 to heat the wafer W on the mounting table 4.

A shower head 12 for introducing a processing gas such as a film-forming gas into the processing chamber 2 is provided on a chamber ceiling that faces the mounting table 4. Four exhaust openings 14 (only two openings are shown in the drawing) disposed with approximately equal intervals are provided on the periphery of the bottom of the processing chamber 2. Each of these exhaust openings 14 is connected to an exhaust pipe 16 extending downward.

Respective discharge sides of the exhaust pipes 16 are assembled into one, which is then connected to one absorption side of an assembling pipe 20 of a large diameter. A butterfly valve 18 for adjusting pressure is provided inside the assembling pipe 20. A vacuum pump 22 is provided at a discharge side of the assembling pipe 20, and a main exhaust pipe 24 of a relatively large diameter is connected to a discharge side of the vacuum pump 22. Atmospheric air and a gas within the processing chamber 2 are exhausted to the outside by this vacuum pump 22. A particle-measuring system 26 for counting the number of particles included in the exhaust gas is provided in the middle of the main exhaust pipe 24.

FIG. 19 is a diagram showing a cross-sectional configuration of the main exhaust pipe 24 provided with the particle-measuring system 26.

The particle-measuring system 26 has a laser beam irradiator 28 for emitting laser beams L and a stopper 32 for suctioning the emitted laser beams L disposed opposite to each other so that a line connecting between the two units pass through a center O of the main exhaust pipe 24. Further, a scattered light detector 30 for detecting scattered lights SL generated by a collision of the laser beams L against particles P in the middle of the irradiation of the laser beams L, is disposed facing the center 0 of the main exhaust pipe 24.

Based on this arrangement, for measuring the particles, the scattered light detector 30 detects the scattered lights SL that are generated when the laser beams L irradiated from the laser beam irradiator 28 have collided against the particles P that move within the main exhaust pipe 24. The particle-measuring system 26 counts the number of the particles included in the exhaust gas based on this detection.

According to the above-described conventional processing unit, the particle-measuring system 26 is provided on the main exhaust pipe 24 at the discharge side of the vacuum pump 22 that assembles the exhaust pipes 16 from the processing chamber 2 together. Of course, abnormalities of products adhere onto the inner walls of the exhaust pipes and blades of the pump and the valve due to the exhaust that occurs during the process from the processing chamber 2 to the particle-measuring system 26. These adhered abnormalities are peeled off irregularly, and these generate new particles.

As the particles generated irregularly are added to the discharged particles that have actually been generated from within the processing chamber 2, it has not been possible to accurately grasp the number of particles that have been generated from within the processing chamber 2.

Further, the exhaust gas is swirled within the exhaust pipe near the discharge side of the vacuum pump 22. Therefore, the same particles cross the laser beams repeatedly, and they are counted by a plurality of times.

In principle, the actual number of particles within the processing chamber 2 should be highly correlated with the count number based on the measurement of particle by the particle-measuring system 26. However, for the above reason, there is a very low correlation between the two data. Therefore, according to the conventional particle-measuring system, it has been difficult to accurately understand the state of particles actually generated from within the processing chamber 2.

Further, for example, when forming a thin film by a film-forming system, e.g., a CVD system, generation of particles which can be a factor of reduction in a yield of a product must be suppressed as low as possible. These particles are generally produced when an unnecessary film that has adhered to a surface of an internal structure, such as an inner wall surface of a process chamber, a mounting table or a shower head structure, flakes away. Therefore, after subjecting one lot (for example, 25) of wafers to film formation processing periodically or non-periodically, there is carried out etching processing which removes an unnecessary film by introducing a cleaning gas, such as $ClF_3$, into the processing chamber, namely, cleaning processing. Generation of the particles in the processing chamber can be suppressed by this cleaning processing.

Since the cleaning gas is highly active, the inner wall surface of the chamber and other internal structures are also scraped away after the unnecessary film is removed, if cleaning processing is carried out longer than necessary. Therefore, it is very important to monitor the scraping state of the wafer during the processing, and determine an appropriate end point (point at which the etched film is removed), in order to terminate the cleaning processing with a just timing.

Description will now be given as to a conventional method for determining termination of the cleaning processing, i.e., the end point.

For example, there is a set a sequence to perform the cleaning processing for a predetermined time every time a predetermined number of, e.g., one lot (25) of wafers to be processed is subjected to film formation processing. At this moment, the predetermined number of wafers are actually subjected to the film formation processing, and an unnecessary film is deposited on the inner wall surface of the chamber or the internal structure. A cleaning processing time to remove the unnecessary film or an interval of execution of cleaning is experimentally obtained, and the cleaning processing is carried out based on such a time or interval. At this moment, the cleaning processing time may be determined by utilizing a plasma monitor. When the unnecessary film is, e.g., a silicon oxide film and the internal structure is, e.g., stainless, the color (wavelength) of light generated differs depending on the plasma. Therefore, the color of the plasma varies at a switching part in accordance with etching. The point in time at which the etched film (unnecessary film) has been completely removed, thus exposing a substrate (internal structure and the like) underneath, is referred to as "just etch".

In actual cleaning processing, the cleaning processing is not terminated at just etch, and is continued for a predetermined period. In order to completely remove an unnecessary film which has adhered to a part where removal of the unnecessary film is difficult, as compared with a mounting table surface where removal of an unnecessary film is easiest, over etching, in which etching processing is prolonged for a predetermined period after the just etch point is carried out, and then the cleaning processing is terminated.

The over etching period is approximately ½ the time required from start of the cleaning processing to the just etch point. Therefore, if 300 seconds are required from start of the cleaning processing to the just etch point, cleaning processing continues for a further 150 seconds, thus cleaning processing reaches the end point after performing etching for a total of 450 seconds.

However, in the actual processing, there is rarely a case that one lot (for example, 25) of wafers to be processed is periodically supplied and manufactured. Therefore, when one lot slightly exceeds 25, several wafers are processed in the last processing. Furthermore, there may be a case that only a few wafers are subjected to film formation processing, and the film-forming system stays in the idling state for a long time until the next wafer to be processed is supplied, and the adherent unnecessary film may possibly change its nature in the processing chamber. Therefore, the cleaning processing is necessarily executed before entering the idling state.

In such a case, the thickness of the adherent unnecessary film is slightly less than the predetermined film thickness. Thus, by executing the regular cleaning processing mentioned above, the inner wall surface in the chamber or the internal structure, e.g., the surface of the mounting table, a shield ring, a shower head structure and others may be scraped away by excessive etching, or the surface of that member may be damaged by etching or corrosion. There occurs a problem that the duration of life of the internal structure is shortened by this damage. When a frequency of replacement of the internal structure becomes high, an operating rate of the system is deteriorated, and the throughput is lowered, which results in a problem that a product cost is adversely affected.

BRIEF SUMMARY OF THE INVENTION

It is an object of the present invention to provide a particle-measuring system capable of grasping a state of generation of particles by keeping high correlation between the number of particles generated and exhausted from within a processing chamber and the counted number of particles based on an accurate counting of the number of particles exhausted.

Moreover, it is another object of the present invention to provide a processing apparatus and a cleaning method which can automatically assuredly grasp a timing of the just etch, determine an end point, appropriately terminate the etching processing and perform cleaning of an unnecessary film deposited in a processing chamber irrespective of the number of objects to be processed before starting the cleaning processing.

The present invention provides a particle-measuring system mounted on a processing system that has a processing unit for carrying out a predetermined processing of an object to be processed and an exhaust system for exhausting an atmospheric gas from within a processing chamber of the processing unit by a vacuum pump. Within the processing system, the particle-measuring system is installed on an exhaust pipe that forms a part of the exhaust system communicating between an exhaust opening of the processing chamber and the vacuum pump. With this arrangement, the particle-measuring system measurers the number of particles included in the exhaust gas discharged from within the processing chamber.

The particle-measuring system is constructed of a laser beam irradiator for irradiating laser beams to within the exhaust pipe so that the laser beams pass along a line connecting between a center point of a cross section of the exhaust pipe and a center axis passing vertically through the center of the processing chamber, and a scattered light detector provided in a direction approximately orthogonal with an irradiation direction of the laser beams, for detecting light scattered from particles.

The present invention also provides a particle-measuring method for measuring the number of particles included in an exhaust gas exhausted from a processing device for generating an atmosphere including atmospheric air or a gas exhausted from within a processing chamber by a vacuum pump, and for processing an object relating to a semiconductor manufacturing in this atmosphere, the method comprising the steps of: modeling parameters; carrying out a numerical simulation for expressing tracks of an exhaust gas that includes particles flowing through an exhaust pipe; carrying out a track numerical simulation of an exhaust gas and particles; confirming an optimum position for measuring particles; determining sensor installation position; installing the sensor; and evaluating a measurement of particle, wherein tracks of particles that flow through the exhaust pipe after the particles have been generated inside the processing chamber and exhausted from the processing chamber are simulated, to select an area where the density of the particles is the highest in the radial direction of the exhaust pipe, a laser beam irradiator is disposed at a position in this area where laser beams for measurement pass through, and a scattered-beam detector is disposed in a direction orthogonal with the laser beams, thereby to measure the particles.

The present invention further provides a particle-measuring method for measuring the number of particles included in an exhaust gas exhausted from a processing device for generating an atmospheric air or a process gas exhausted from within a processing chamber by a vacuum exhaust system, and for processing an object relating to a semiconductor manufacturing in this atmosphere, the particle measuring method using a device having a laser irradiator, a scattered-beam detector and a beam stopper for measuring the number of particles by irradiating laser beams to particles generated within the processing chamber, the particle-measuring method comprising the steps of: selecting an area in which the density of particles is high by carrying out a simulation based on information on constructional members including the processing chamber and other members disposed inside the processing chamber, information on the vacuum exhaust system, and information on the process gas; adjusting a position of the laser beam irradiator so that the laser beam irradiator can irradiate laser beams in an area in which the density of particles is high based on the simulation; adjusting a position of the beam stopper to face the laser irradiator so that the beam stopper can receive laser beams passed through the high-density area; adjusting a position of the scattered-beam detector so that the scattered-beam detector can detect scattered beams of the laser beams passed through the high-density area; irradiating by the laser irradiator the laser beams to an area in which the density of particles is high; detecting by the scattered-beam detector the scattered beams of the laser beams passed through the high-density area; and calculating the number of particles from the scattered beams detected.

BRIEF DESCRIPTION OF THE SEVERAL VIEWS OF THE DRAWING

FIGS. 9A, 9B and 9C are diagrams showing a second example of a particle distribution according to a simulation relating to the present embodiment;

FIG. 15 is a diagram showing one example of a particle distribution state obtained by a simulation according to the second embodiment;

FIG. 16 is a diagram showing a positional relationship among a laser beam irradiator, a stopper member and a scattered light detector when the simulation data has been applied to the second embodiment;

FIG. 20 is a view showing a structural example of a processing system according to a third embodiment having a particle measuring portion mounted thereon;

FIGS. 23A and 23B are views showing results of examining the correlation between a just etch point and increase/decrease in the number of particles;

FIGS. 29A to 29D are views showing a degree (%) a chip number depending on presence/absence of each gas or when a flow quantity of each gas is changed;

FIG. 34 is a view showing a cross-sectional structure of a fourth modification of the delivering mechanism;

FIG. 35 is a view showing a cross-sectional structure of a fifth modification of the delivering mechanism;

FIG. 36 is a view showing a structure of a gas mixing portion which introduces a process gas;

DETAILED DESCRIPTION OF THE INVENTION

An embodiment of the present invention will be explained in detail with reference to the drawings.

Figure 1:
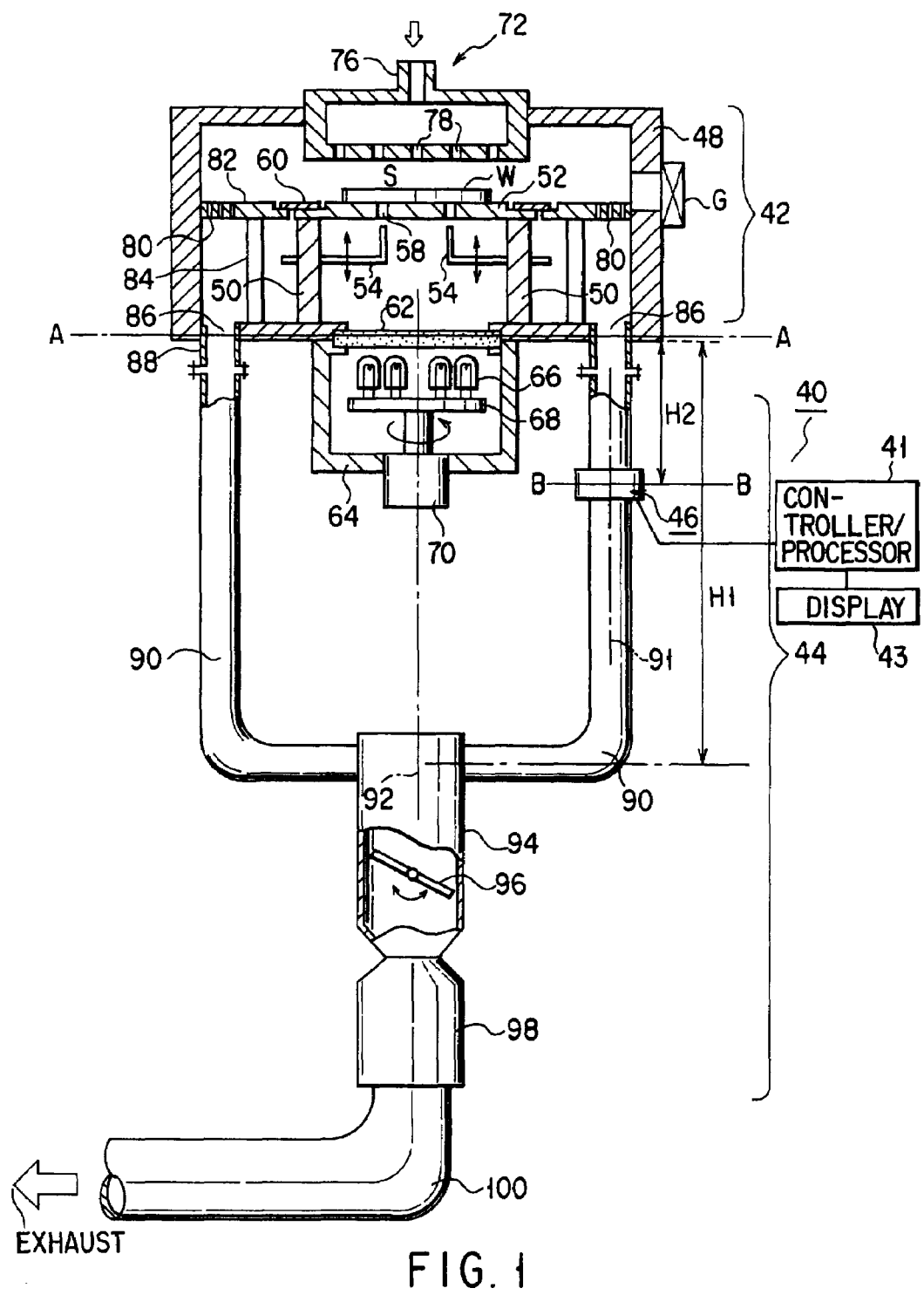
FIG. 1 is a configuration diagram showing a processing system on which a particle-measuring system relating to a first embodiment of the present invention is mounted.

FIG. 1 is a configuration diagram showing a processing system on which a particle-measuring system relating to a first embodiment of the present invention is mounted. The present embodiment will be explained by taking a CVD system as one example of a processing system for forming films on a semiconductor wafer (hereinafter to be referred to as a wafer) as an object to be processed. It is of course possible to similarly apply the particle-measuring system to other processing systems such as a sputtering system and an etching system.

The CVD system 40 is broadly constructed of a processing unit 42 for forming a film by using a film-forming gas on a wafer W, and an exhaust unit 44 for discharging atmospheric air and a film-forming gas within the processing unit 42. A particle-measuring system 46 for measuring the number of particles included in the exhaust gas flowing through the exhaust unit 44 is mounted on the CVD system 40.

The particle-measuring system 46 is controlled by a controller/processor 41 to carry out an arithmetic processing and the like. There is also provided a display 43 for making a display of processing results and expressions and various parameters to be used for simulations.

The control and process section 41 may be provided in or outside the system control section that controls the entire processing system.

This processing unit 42 has a processing chamber 48 made of aluminum (Al) in a cylindrical or boxed shape, for example. A cylindrical reflector 50 extending upward from the bottom of the processing chamber 48 is disposed within the processing chamber 48. Further, a mounting table 52 for mounting the wafer W thereon is installed on the reflector 50.

This reflector 50 is formed using aluminum as a heat-ray reflective material, for example. The mounting table 52 is formed using a carbon material having a thickness of about 1 mm or an aluminum alloy such as aluminum nitride (AlN).

A plurality of lifter pins 54, for example, three lifter pins (only two lifter pins are shown in the example) that move together in up and down directions are disposed below the mounting table 52. A driving unit not shown drives the lifter pins 54 to lift the wafer W upward from the bottom surface of the mounting table 52 through lifter pin holes 58 formed on the mounting table 52. The wafer W is lifted upward by these lifter pins 54, and is carried inside the processing chamber and to the outside by a carrying mechanism having an arm or the like not shown.

A ring-shaped shield ring 60 for guaranteeing a uniform surface of a film deposited on the wafer surface is provided at the periphery of the mounting table 52.

Further, a transmission window 62 made of a heat-ray transmission material of quartz or the like is provided on the bottom of the processing chamber below the mounting table 52 to seal the chamber air-tightly. Further below this transmission window 62, there is provided a boxed-shaped heating room 64 to encircle the transmission window 62.

Within this heating room 64, a plurality of heating lamps 66 as a heat source are installed on a rotary table 68 working also as a reflection mirror. This rotary table 68 is connected to a motor by a rotary axis, and is rotated according to the rotation of the motor 70. It is possible to uniformly heat the wafer W based on this rotation.

Heat beams emitted from the heating lamps 66 are transmitted through the transmission window 62 to irradiate the bottom surface of the mounting table 52 to heat the back side of the wafer W. As the heating source, it is also possible to use a resistance-heating heater by having the resistance-heating heater embedded on the mounting table 52, in place of the heating lamps 66. Alternatively, it is also possible to heat the back side of the wafer W by blowing a heating medium such as a heated gas onto the mounting table 52.

On the ceiling of the processing chamber that faces the mounting table 52, there is provided a shower head 72 having a large number of gas injection holes 78 for introducing a processing gas such as a film-forming gas into the processing chamber 48. This shower head 72 is formed in a round box shape using, for example, aluminum or the like, and is formed with a gas introduction opening 76 for supplying a gas based on a connection to a gas introduction system not shown.

On the outer periphery of the mounting table 52, a ring-shaped rectification plate having a large number of rectification holes 80 is supported in up and down directions by a supporting column 84 formed in a ring shape. A plurality of exhaust holes 86 are formed on the bottom of the chamber below this rectification plate 82.

Figure 2:
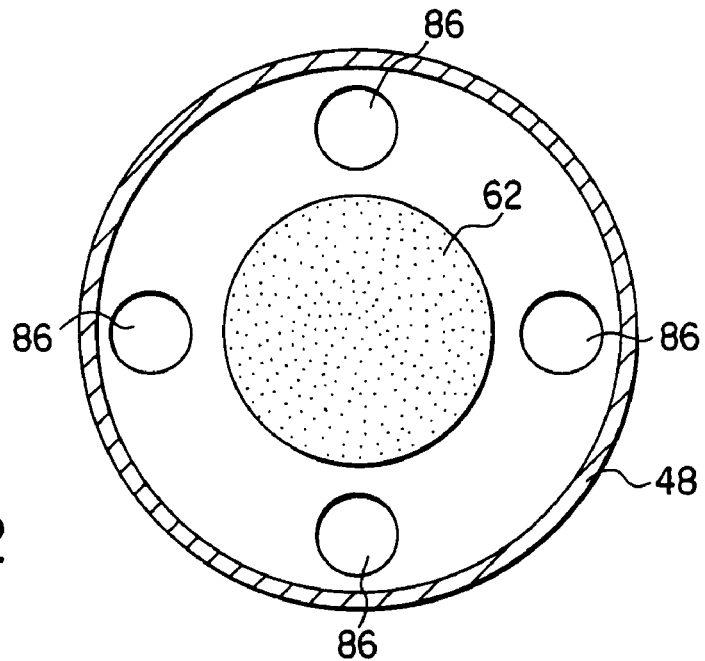
FIG. 2 is a top plan view showing a positional relationship between a transmission window and exhaust openings within a processing chamber.

FIG. 2 is a top plan view cut along a line A-A of FIG. 1 showing a positional relationship between the transmission window and the exhaust holes within the processing chamber. As shown in FIG. 2, in the present embodiment, four exhaust holes 86 are provided in approximately an equal interval along the periphery of the bottom. An exhaust pipe 88 is provided for each exhaust opening 86.

Each exhaust pipe 88 is connected in air tight to each exhaust pipe 90 that forms a part of the exhaust system 44 via a gasket based on a coupling not shown.

These exhaust pipes 90 have straight tubular shapes at the rising portions, and their discharge sides are assembled into one, which is then connected to an assembling pipe 94 having a relatively large diameter. A butterfly valve 96, for example, for adjusting the internal pressure of the processing chamber 48 is provided inside the assembling pipe 94. A vacuum pump 98 such as a turbo molecular pump is provided at a discharge side of the assembling pipe 94. A main exhaust pipe 100 of a relatively large diameter is connected to a discharge side of the vacuum pump 98. Atmospheric air and a film-forming gas within the processing chamber are exhausted to the outside from the chamber through the main exhaust pipe 100 by this vacuum pump 98.

A particle-measuring system 46 for counting the number of particles is provided in the middle of one or more of the four exhaust pipes 90 of the CVD unit.

A film-forming processing by the CVD unit of the present embodiment will be explained next.

At first, a gate valve G provided on the side wall of the processing chamber 48 is opened, and the wafer W is carried into the processing chamber 48 with a carrying arm not shown. The wafer W is delivered to the lifted lifter pins 54. Then, the lifter pins 54 are lowered to mount the wafer W on the mounting table 52. The carrying arm is then retired and the gate valve G is closed. Thereafter, the atmospheric air within the processing chamber 48 is exhausted by the exhaust system 44.

As a processing gas from a processing gas source not shown, gases of $WF_6$ (a raw material gas), $SiH_2Cl_2$, Ar, etc. are supplied by a predetermined volume for each gas to the shower head 72, and the gases are mixed together to form the processing gas. The processing gas is then supplied approximately uniformly to within the processing chamber 48 from the gas injection holes 78.

The supplied film-forming gas is suctioned and exhausted from each exhaust opening 86 to the exhaust system 44, and the inside of the processing chamber 48 is set to a predetermined vacuum level. The heating lamps 66 are operated to emit light beams by rotating the rotary table 68 to irradiate the heating beams onto the wafer W from the back side of the mounting table 52. Thus, the wafer W is promptly heated to a predetermined level of temperature, and this temperature is maintained.

A predetermined chemical reactance of the film-forming gas occurs in the atmosphere within this processing chamber 48. As a result, tungsten silicide, for example, is deposited on the surface of the wafer W.

The film-forming gas within the processing chamber 48 flows down as an exhaust gas through each exhaust pipe 90 from each exhaust opening 86. All the exhaust gases from the exhaust pipes 90 are collected inside the assembling pipe 94. The collected exhaust gas passes through the vacuum pump 98 while being pressure-adjusted by the pressure-adjusting valve 96, and is discharged to the outside of the system from the main exhaust pipe 100. The particle-measuring system 46 counts the number of particles included in the exhaust gas.

The particle-measuring system 46 will be explained next.

Figure 3:
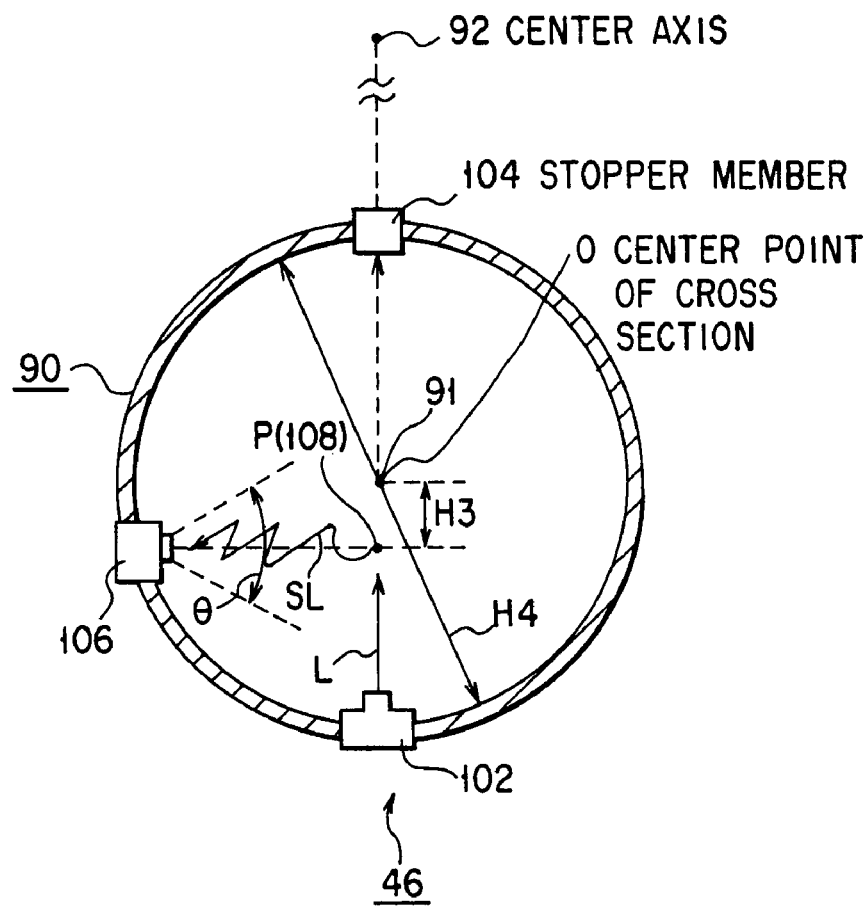
FIG. 3 is a diagram showing an installation state of the particle-measuring system.

As shown in FIG. 3, each particle-measuring system 46 consists of a laser beam irradiator 102 having a laser device for irradiating very fine laser beams L, a stopper member 104 disposed opposite to the laser beam irradiator 102 through a center axis 91 of the exhaust pipe 90, and a scattered light detector 106 of a light receiving element installed on the pipe wall in a direction approximately orthogonal with the irradiation direction of the laser beams L. The laser element described above is a semiconductor laser element which is small in size and formed of GaAlAs, for example.

The laser beam irradiator 102 is provided on the pipe wall so that the irradiated laser beams L pass along a line connecting between a center axis 92 of the chamber and a center point O of the cross section of the center axis 91 (reference FIG. 1) of the exhaust pipe 90.

The laser beams L may be in irradiated in any direction so long as the irradiated laser beams L are directed to the direction in which the center axis 92 of the chamber exists through the center point O of the cross section. However, a relative positional relationship with the scattered light detector 106 is maintained.

The stopper member 104 suctions the laser beams L to avoid the generation of a diffuse reflection or the like of the laser beams L within the exhaust pipe 90.

The scattered light detector 106 made of the light receiving element or the like is provided on the pipe wall in a direction approximately orthogonal with the irradiation direction of the laser beams L as shown in FIG. 3. When the laser beams L are irradiated onto particles P (108) included in the exhaust gas, the scattered light detector 106 receives scattered lights SL that have been generated by the irradiation of the laser beams L. As described later, the center of the scattered light detector 106 is not directed toward the center point 0 of the cross section, but is disposed in an offset distance H3 that has been offset as shown in FIG. 3.

Figure 4:
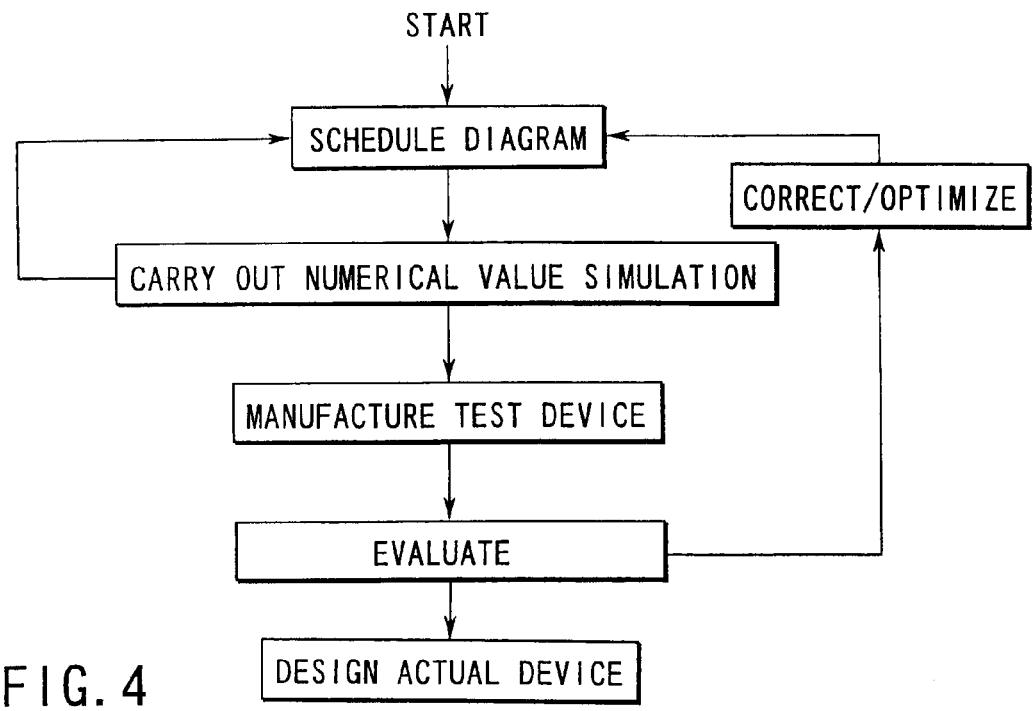
FIG. 4 is a flowchart for explaining a manufacturing of a processing system on which the particle-measuring system is to be mounted.

A position H2 for installing the particle-measuring system 46 on the exhaust pipe 90 is determined based on a computer simulation to be carried out according to a flowchart as shown in FIG. 4. One example of this computer simulation will be explained next.

First, an outline of the processing system is scheduled. Specifically, a basic system design (process conditions) including a chamber capacity, an exhaust ability, a kind of a film-forming gas, a gas supply system, a length and a diameter of an exhaust pipe, etc., is determined. Next, the installation distance H2 of the particle-measuring system 46 and the offset distance H3 are calculated according to a simulation of numerical values to be described later, and a test manufacturing of the particle-measuring system to be mounted on an actual processing system is carried out. Thus, particles are actually measured. In the evaluation of the actual measurement, when a result of the actual measurement is different from a result of the simulation or when an expected performance has not been obtained, the basic system design is corrected or optimized based on the result of the evaluation. In other words, the design is reviewed including changes in the position of installing the particle-measuring system 46, etc.

When a result of the actual measurement is satisfactory, the installation position of the particle-measuring system 46 and the offset position are reflected to a product (a processing system) on a manufacturing line.

Figure 5:
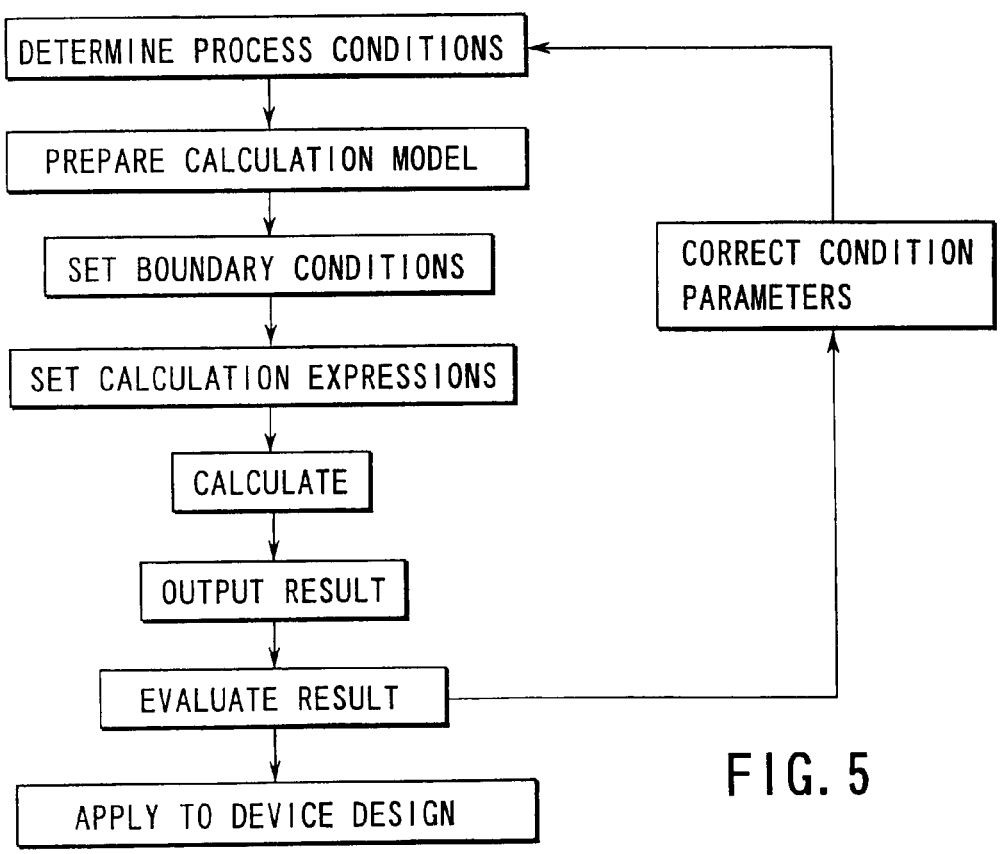
FIG. 5 is a flowchart for explaining a numerical value simulation for calculating a position of installing the particle-measuring system on the processing system.

The numerical simulation will be explained with reference to a flowchart shown in FIG. 5.

First, a calculation model (a mesh model) is prepared using computer software for calculation (for example, GAMBIT manufactured by Fluent Asia Pacific Co., Ltd.). For example, a calculation expression for setting boundary conditions (for example, a wall-surface temperature and pressure of the exhaust pipe, a kind of gas to be exhausted, etc.) is prepared based on the above-described basic system conditions (process conditions) using FLUENT of Fluent Asia Pacific Co., Ltd. This calculation is carried out. A result of the calculation is reflected to an actual system (a test system). In other words, the particle-measuring system 46 is installed on a calculated position, and a result is evaluated. When the result is satisfactory, the result is reflected to a design of a system to be manufactured.

As a result of this simulation, in the present embodiment, about 130 mm is determined as an optimum installation distance H2 from the exhaust opening 86 to the particle-measuring system 46 when a length H1 in a vertical direction is 430 mm, for example, in the exhaust pipe 90 of NW40.

For optimizing the position of installing the particle-measuring system 46, the following are the essential conditions. That is, there is no wraparound of beams generated in the processing chamber, such as, for example, heating beams (when the lamp heaters are the heating source) or plasma beams. There is space around for the installation, and that a density of particles is relatively high in the exhaust pipe or a track of an exhaust gas.

Particularly, the density of the flow of an exhausted film-forming gas within the exhaust pipe or the track of the exhaust gas is different depending on a kind of gas (a diameter and weigh of a particle), a layout shape of the exhaust pipe, a diameter of the exhaust pipe, an exhaust speed, weight, etc. Therefore, the density of particles is not necessarily high at the center of the exhaust pipe. This will be explained next.

Particles included in the exhaust gas flowing through the exhaust pipe 90 are not uniformly distributed in the gas, but tend to be unevenly distributed to an outside direction away from the center axis 92 of the processing chamber 48.

The reason is as follows. The film-forming gas supplied from the showerhead 72 into the processing chamber 48 flows down and is dispersed straight to the periphery of the processing chamber 48. The dispersed gas is then suctioned by each exhaust opening 86, and flows down through the exhaust pipe 90. Inertial force in a dispersion direction, that is, inertial force toward the outside in a radial direction of the processing chamber 48 applies directly to the particles.

Figure 6:
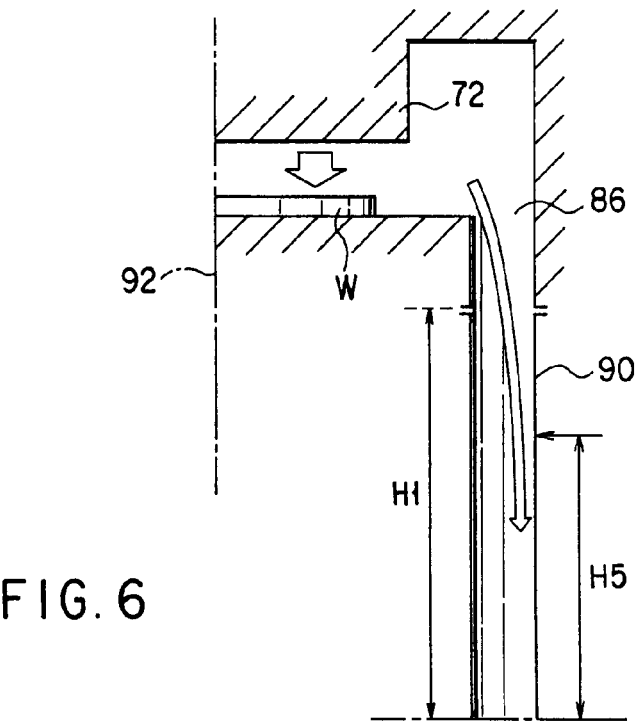
FIG. 6 is a diagram showing a model inside the processing chamber and an exhaust pipe obtained based on the simulation.

Therefore, the particles included in the exhaust gas flowing down through the exhaust pipe 90 are unevenly distributed in an outside direction away from the center axis 92 as shown in FIG. 6. As a result, the density of the particles is highest at a point of the downward offset distance H3 from the center point O of the cross section, as shown in FIG. 3.

FIG. 6 shows one example of a model of the exhaust pipe within the processing chamber based on the above-described simulation, for example. Referring to FIG. 6, the film-forming gas ejected from the showerhead 72 is collided against the surface of the wafer W and is dispersed to the surrounding. The dispersed gas then flows down through the exhaust pipe 90 via each exhaust opening 86. FIG. 6 shows a cross-sectional state of the distribution of the particles where the height H1 of the exhaust pipe 90 is 40 cm, a distance H5 from the bottom end of the exhaust pipe 90 is 30 cm, and the inner diameter of the exhaust pipe is 40 mm.

In this example, the exhaust gas flows down through the exhaust pipe 90, with the inertial force applied straight to the exhaust gas toward the outer peripheral direction of the processing chamber 48. Therefore, the density of the exhaust gas is considered to be higher toward the outside of the processing chamber within the exhaust pipe.

In this example, the exhaust gas flows down through the exhaust pipe 90, with the inertial force applied straight to the exhaust gas toward the outer peripheral direction of the processing chamber 48. Therefore, the density of the exhaust gas is considered to be higher toward the outside of the processing chamber within the exhaust pipe. That is, the density of the particles becomes higher on the outer side or the wall side rather than the center of the exhaust pipe. In the present embodiment, the exhaust pipe extends downwards from the bottom of the process chamber 48. Alternatively, the exhaust pipe may extend upwards from the top of the chamber 48, horizontally from one side thereof, or slantwise from any part thereof. Simulation is performed on these alternative embodiments, too.

Therefore, as shown in FIG. 3, the center of the detection direction of the scattered light detector 106 is directed outside to the center point O of the cross section of the exhaust pipe. Instead, the center of the detection direction of the scattered light detector 106 is directed to a point P (this point P is a point where the density of the particles is approximately the highest as described later) away outside from the chamber center axis 92 by a predetermined offset distance H3.

In this case, the directivity of the scattered light detector 106 has a certain level of an opening angle θ. When the scattered light detector 106 is disposed at a position with a move by the offset distance H3, the scattered light detector 106 can detect with a high sensitivity in an area where the density of the particles is approximately the highest.

Although a maximum value of the offset distance H3 depends on the process conditions, this value is about 0.75 times the radius of the exhaust pipe 90 as described later. Therefore, the center of the scattered light detector 106 is set at one point in an area within the range of an outside distance from the center point O of the cross section to a point 108 shown by the distance H3.

In this example, when the diameter within the processing chamber 48 for processing an 8-inch wafer is about 440 mm and an internal diameter H4 of the exhaust pipe 90 is about 40 mm, the offset distance H3 is set at about 10 mm.

From the above, according to the present embodiment, as the particle-measuring system 46 is installed on the exhaust pipe 90 at the upstream of the vacuum pump 98, the distance of a gas route between the processing chamber 48 and the installation position of the particle-measuring system 46 becomes short. Therefore, the scattered light detector 106 can accurately detect the scattered lights SL generated based on the irradiation of the laser beams L onto the particles P as shown in FIG. 3, without detecting unnecessary particles irregularly generated.

As a result, it is possible to monitor the number of particles in high correlation with the actual volumes of particles within the processing chamber 48.

As shown in FIG. 3, according to the present embodiment, the laser beams L irradiated by the laser beam irradiator 102 pass through the area in which the particles tend to be highly concentrated. Further, the laser beams L are irradiated through the point P at which the particle density is the highest. Further, the center of the scattered light detector 106 is directed toward the point P at which the particle density is the highest. Therefore, it is possible to efficiently irradiate the laser beams L to the concentrated particles. Furthermore, it is possible to efficiently detect the generated scattered lights SL.

Figure 7:
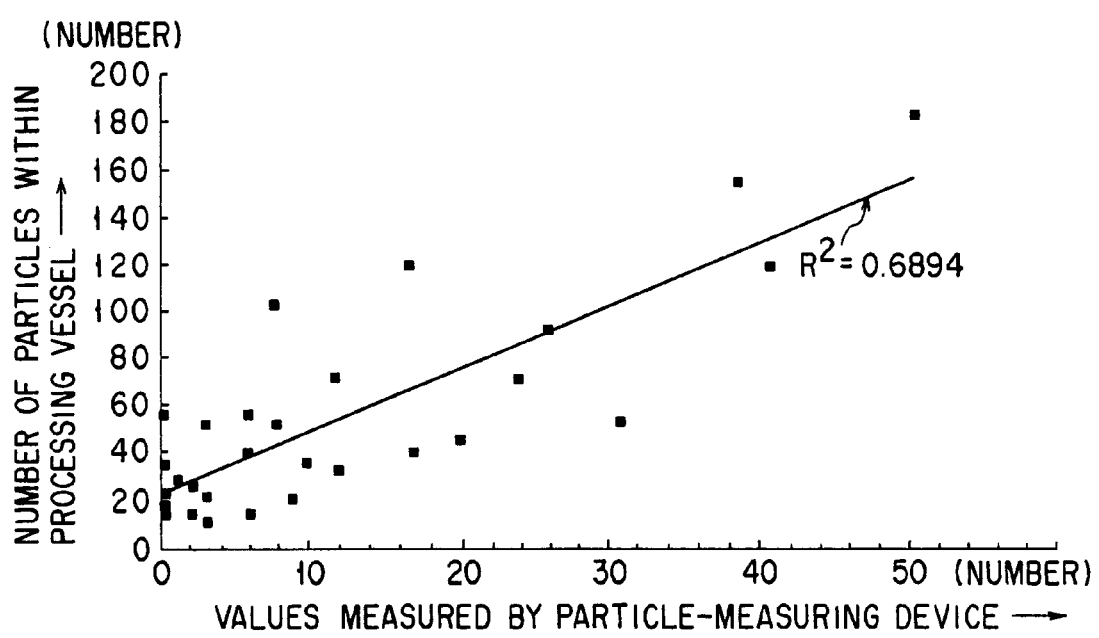
FIG. 7 is a graph showing a correlation between the number of particles within the processing chamber and the number of particles measured by the particle-measuring system.

FIG. 7 is a graph showing a correlation between the actual number of particles within the processing chamber and the number of particles measured by the particle-measuring system of the present embodiment. In this example, the diameter of particles that can be measured is 0.2 μm or above. The number of particles within the processing chamber has been obtained by measuring the number of particles on the surface of a wafer monitored by a monitor installed within the processing chamber 42. The process pressure is 0.7 Torr (93.3 Pa). As is clear from this graph, a correlation coefficient $R^2$ of the correlation between both numbers is 0.6894, and it has been confirmed that it is possible to obtain a considerably high value.

Accordingly, it is possible to detect the number of particles in higher correlation with the actual number of particles within the processing chamber 48. In this case, as the directivity of the scattered light detector 106 has a certain level of the opening angle θ, it is also possible to detect the number of particles in a high correlation when the center of the scattered light detector 106 is directed to a point deviated from the point P, for example, the center point O of the cross section.

Figure 8C:
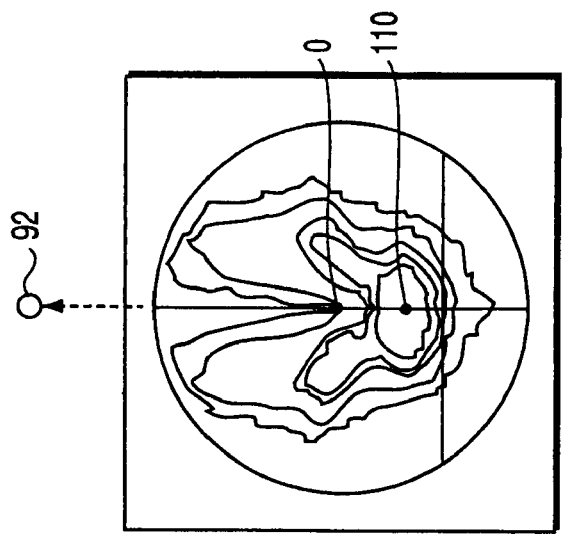
FIGS. 8A, 8B and 8C are diagrams showing a first example of a particle distribution according to a simulation relating to the present embodiment.
Figure 8B:
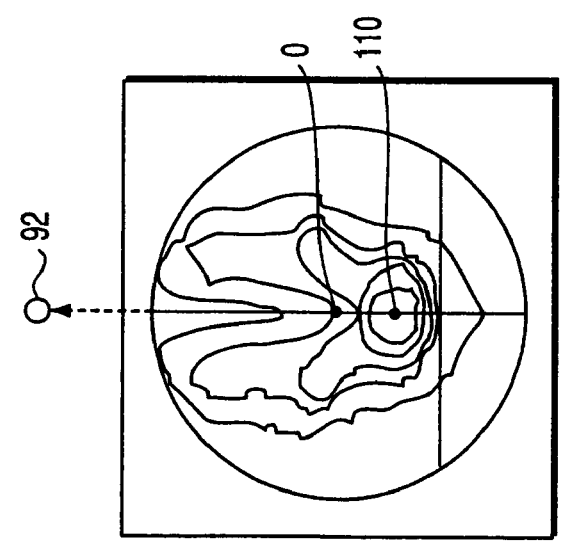
Figure 8A:
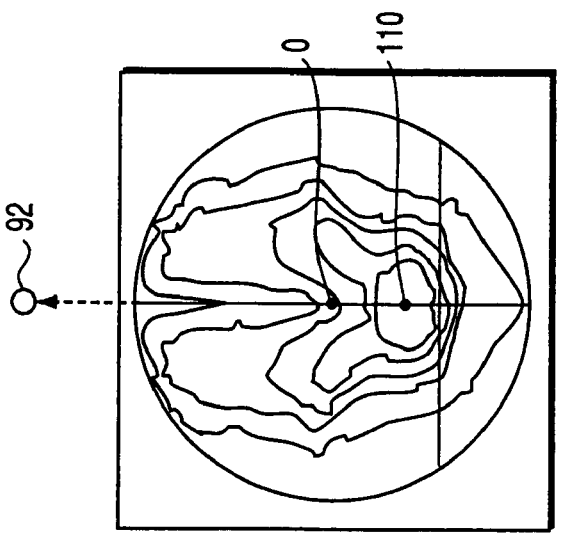

As a result of simulations, FIGS. 8A to 8C show particle distributions within the exhaust pipe when the pressure inside the processing chamber 42 is 0.7 Torr (93.3 Pa) and the film-forming temperature is 520° C. FIGS. 9A to 9C show particle distributions within the exhaust pipe when the pressure inside the processing chamber 42 is 4.5 Torr (599.8 Pa) and the film-forming temperature is 580° C. As a film-forming gas, $WF_6$, $SiH_2Cl_2$ and Ar are used. In each of these drawings, a direction in which the processing chamber center axis 92 is positioned is set above.

As shown in FIGS. 8A to 8C, when the pressure inside the processing chamber 42 is 0.7 Torr (93.3 Pa), the particles are collected in a relatively higher concentration in a direction (downward in the drawings) opposite to the direction in which the center axis 92 of the processing chamber is positioned. Particularly, the particles are concentrated at a lower position than the center point O of the cross section of the exhaust pipe. In other words, the particles are positioned in an outside direction away from the center axis 92 of the processing chamber.

This trend is the same when the diameter of the particles is 0.2 μm (FIG. 8A), 0.5 μm (FIG. 8B), and 1.0 μm (FIG. 8C). In this case, a distance between the center point O of the cross section of the exhaust pipe and a point 110 where the particle density is the highest is approximately 10 mm.

Further, as shown in FIGS. 9A to 9C, when the pressure inside the processing chamber 42 is 4.5 Torr (599.8 Pa), the particles are also collected in a relatively higher concentration in a direction (downward in the drawings) opposite to the direction in which the center axis 92 of the processing chamber is positioned. Particularly, the particles are concentrated at a lower position than the center point O of the cross section of the exhaust pipe. In other words, the particles are positioned in an outside direction away from the center axis 92 of the processing chamber. This trend is the same when the diameter of the particles is 0.2 μm (FIG. 9A), 0.5 μm (FIG. 9B), and 1.0 μm (FIG. 9C). In this case, a distance between the center point O of the cross section of the exhaust pipe and a point 112 where the particle density is the highest is approximately 15 mm.

As explained above, the center point of the particle density is slightly shifted downward in FIGS. 9A to 9C from those points shown in FIGS. 8A to 8C.

As a result of carrying out a similar simulation for each particle material of $WSi_2$, C, and Al, approximately the same distributions have been obtained. As explained above, although it depends on the process, it is possible to efficiently detect scattered lights when a particle high-density area exists within an area sandwiched between the center point O of the cross section of the exhaust pipe 90 and a point of about a maximum 15 mm away downward from this center point O and also when the center of the scattered light detector 106 (reference FIG. 3) is directed to within this area in each drawing. When the diameter of the exhaust pipe 90 is 40 mm (that is, the radius is 20 mm), the maximum 15 mm corresponds to 0.75 times the radius.

In the present embodiment, the laser beams L irradiated from the laser beam irradiator 102 have been set in a direction toward the center axis 92 of the processing chamber through the center point O of the cross section of the exhaust pipe 90. However, the setting of the laser beams L is not limited to this. The laser beams L may be set in any direction when the laser beams L are set to transmit through the area in which the particle density is high.

Figure 10:
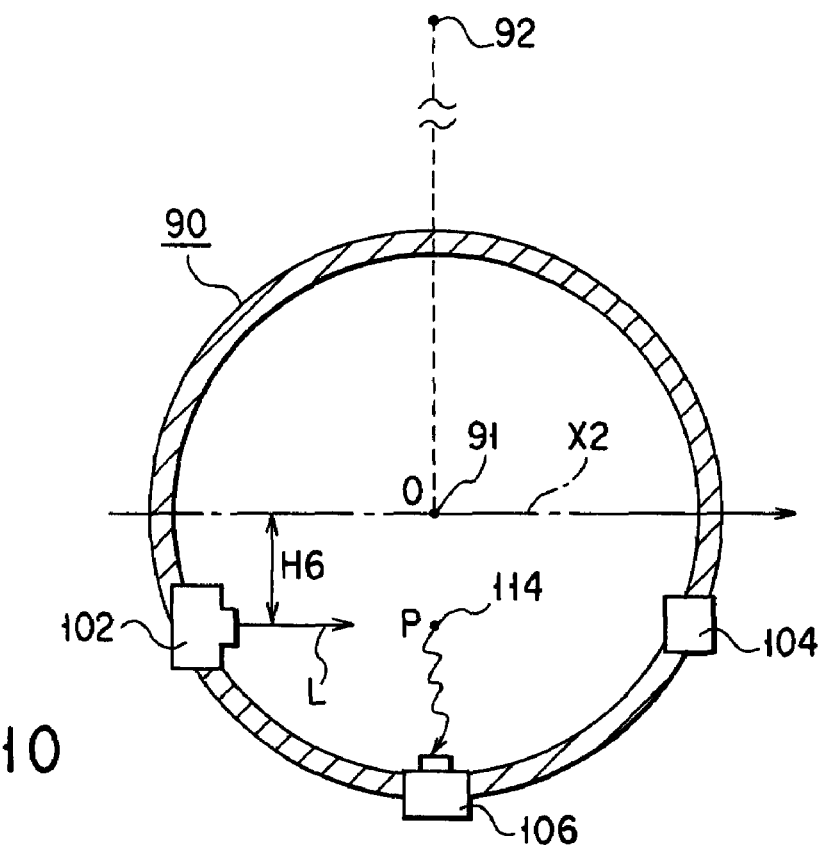
FIG. 10 is a diagram showing a modification of an installation state of the particle-measuring system in the present embodiment.

For example, as shown in FIG. 10, the laser beam irradiator 102 is set so that the laser beams L can be transmitted through a point P that is a position with a predetermined offset distance H6 from the center point O of the cross section of the exhaust pipe 90 to a direction opposite to the direction in which the center axis 92 of the processing chamber is positioned. In this example, the irradiation direction of the laser beams L is along a direction approximately orthogonal with a direction from the center point O of the cross section to the center axis 92 of the processing chamber. The scattered light detector 106 is set in a direction approximately orthogonal with the irradiation direction of the laser beams L. The center of the scattered light detector 106 is directed toward the point P where the density of the particles is high. As described above, a maximum value of the offset distance H6 from the center point O is 0.75 times of the radius of the exhaust pipe. In this case, the offset distance H6 is set to about 12 mm, for example.

Figure 11:
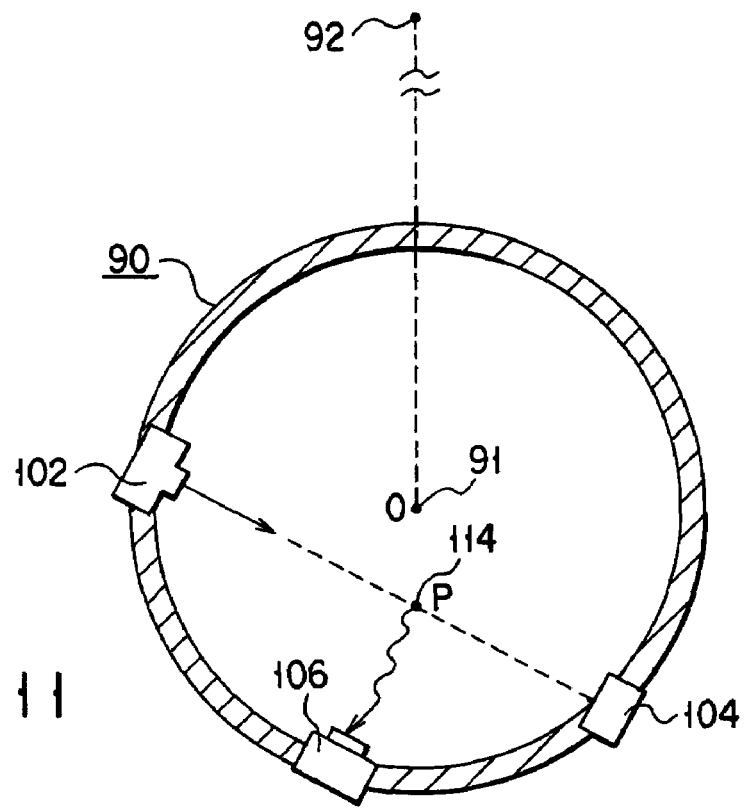
FIG. 11 is a diagram showing another modification of an installation state of the particle-measuring system in the present embodiment.

When the irradiation direction of the laser beams L passes through an area between a center point O (91) of the cross section and a point P (114), this direction is not particularly limited. For example, as shown in FIG. 11, the laser beams L may be irradiated from an inclined direction as compared with the direction shown in FIG. 10. A measurement of particles carried out based on the example of the particle-measuring system shown in FIG. 10 has been evaluated, and a result of this evaluation will be explained with reference to FIGS. 12 and 17.

Figure 12:
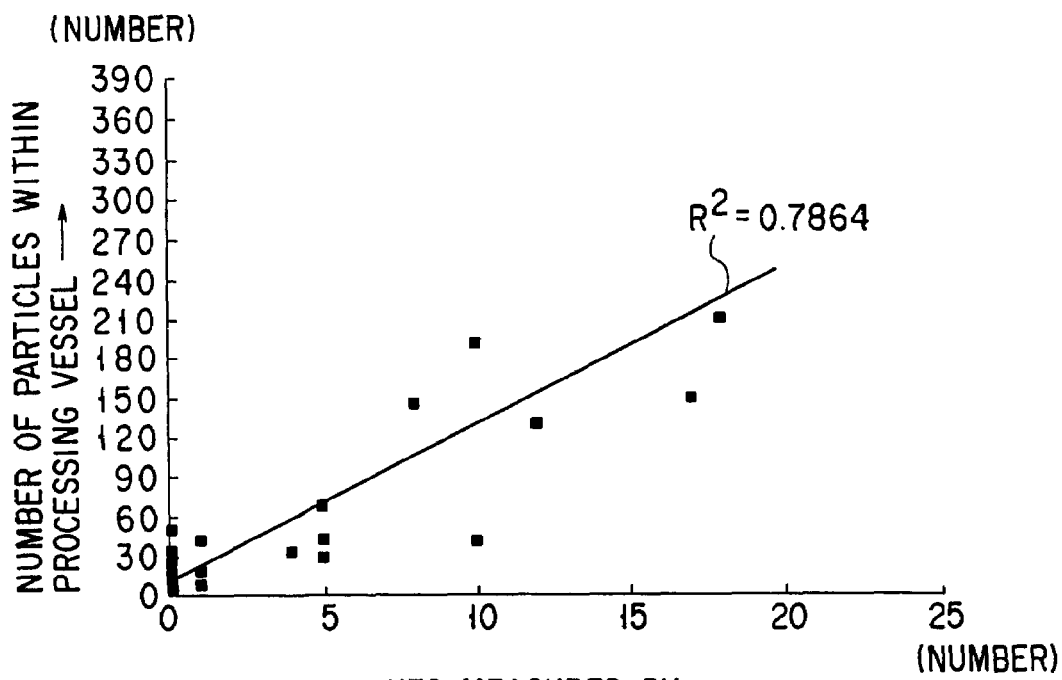
FIG. 12 is a graph showing an evaluation result of a measurement of the number of particles by passing laser beams through a portion (a point P) of a high particle density within the exhaust pipe in the particle-measuring system according to the present embodiment shown in FIG. 10.
Figure 17:
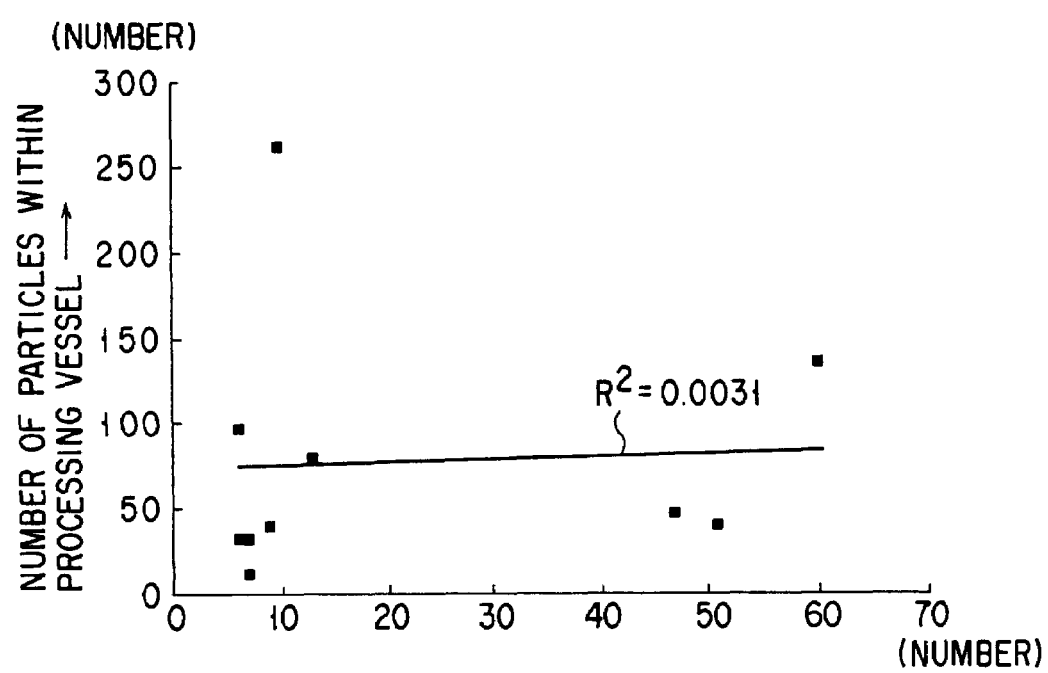
FIG. 17 is a graph showing an evaluation result of a measurement of the number of particles by passing laser beams through an exhaust pipe in a conventional particle-measuring system shown in FIG. 19.
Figure 18:
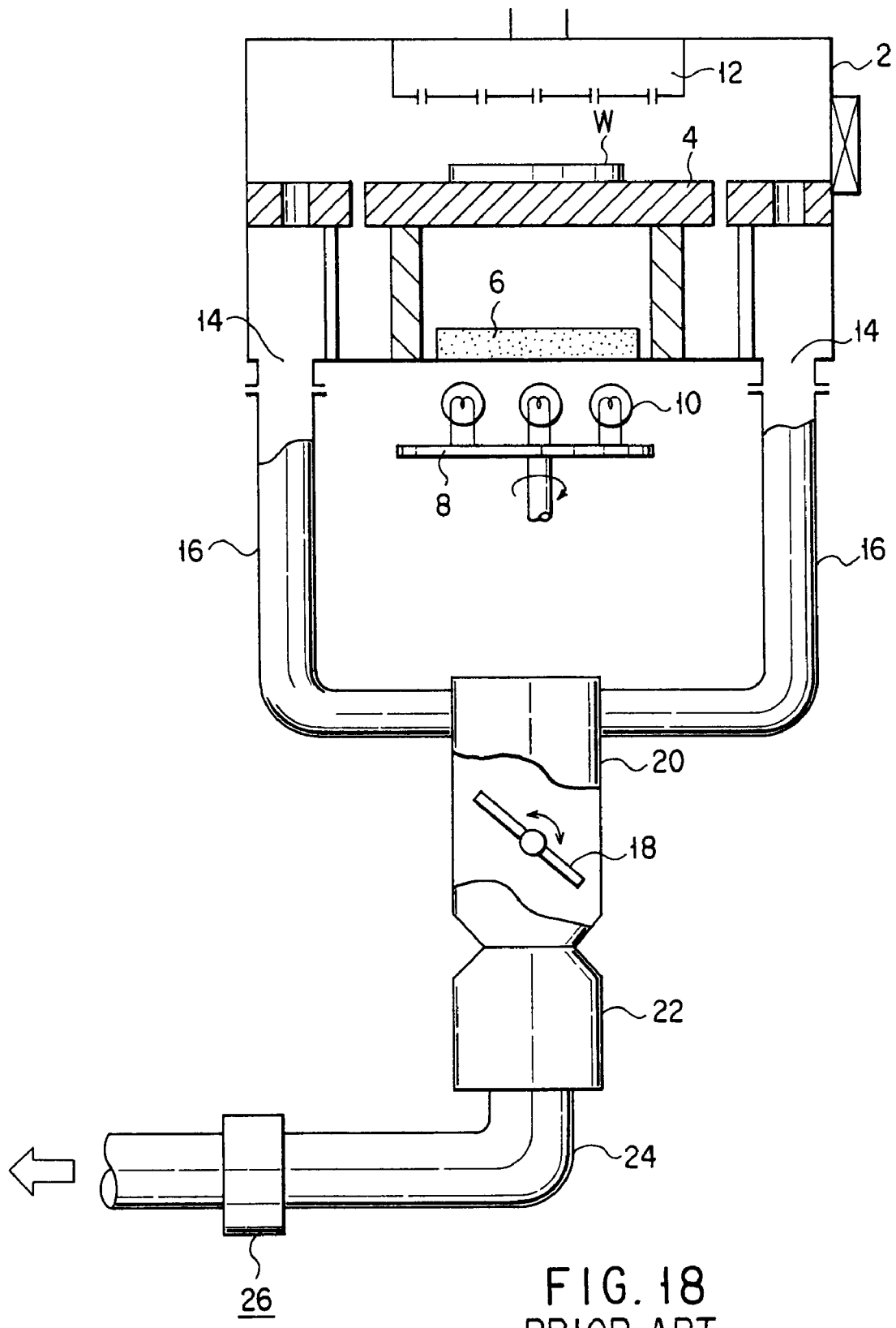
FIG. 18 is a configuration diagram showing one embodiment of a processing system on which the conventional particle-measuring system is mounted.
Figure 19:
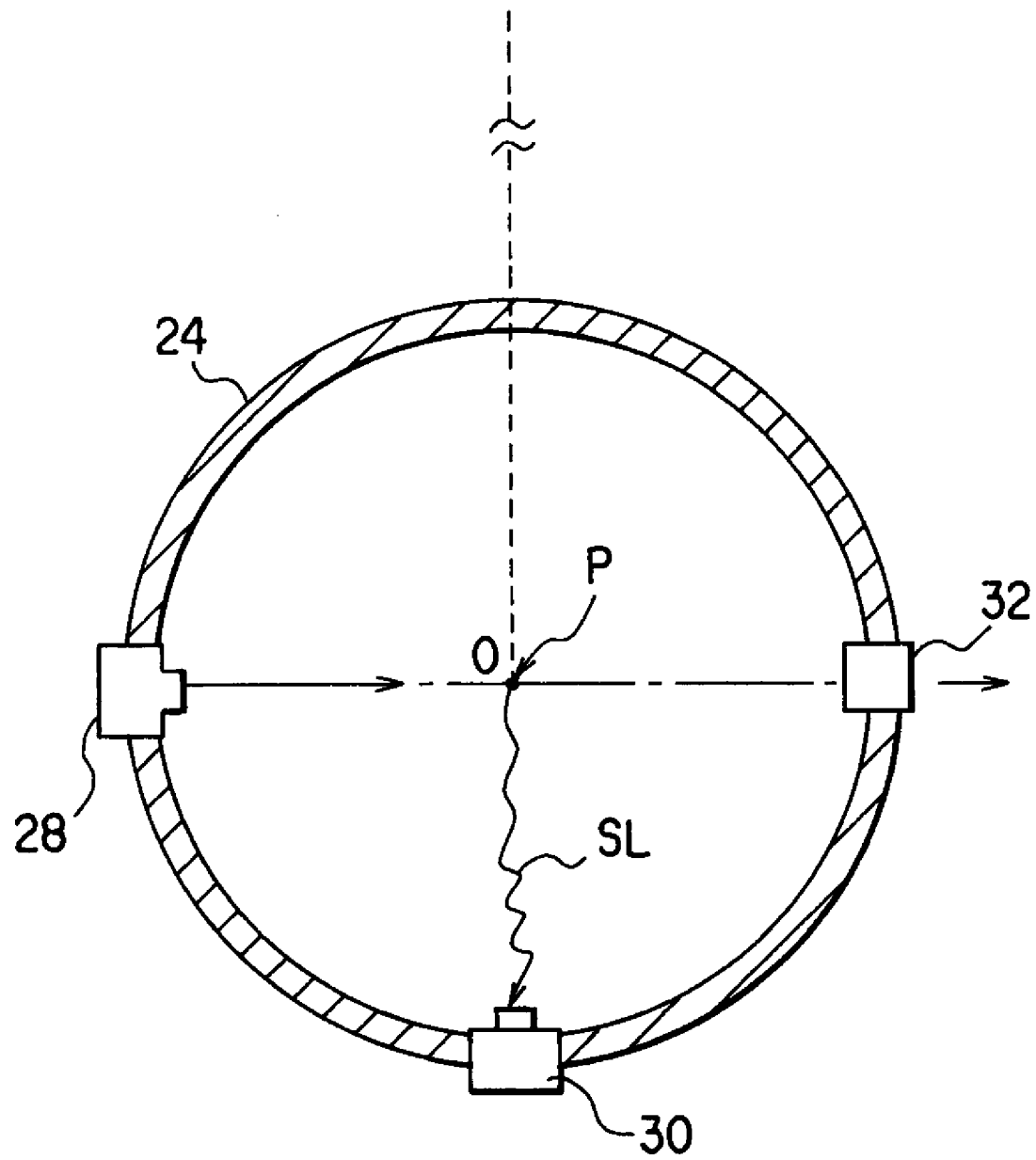
FIG. 19 is a diagram showing an installation state of the conventional particle-measuring system.

FIG. 12 is a graph showing an evaluation result of a measurement of the number of particles by passing the laser beams L through the point (the point P) where the density of the particles within the exhaust pipe is high, using the particle-measuring system according to the embodiment shown in FIG. 10. FIG. 17 is a graph showing an evaluation result of a measurement of the number of particles by passing the laser beams L through the exhaust pipe 90 using the conventional particle-measuring system shown in FIG. 18. In both cases, the particles measured have a diameter of 0.23 μm or above.

According to the present embodiment, a correlation coefficient $R^2$ becomes 0.7864 as shown in FIG. 12, which is a very high satisfactory value. On the other hand, according to the conventional particle-measuring system, a correlation coefficient $R^2$ becomes 0.0031 as shown in FIG. 17, which is a very low value.

It has been confirmed that it is possible to obtain a substantially improved high coefficient of correlation when laser beams have been passed through the portion where the density of particles is high like the present embodiment.

In the above description, a film-forming system has been explained by taking a lamp-heating system as an example. However, the film-forming system is not limited to this. It is needless to mention that the present invention can also be applied to a resistor-heating type film-forming system or a system using plasma. A film-forming system having a heating lamp, according to the invention, has been described. Nonetheless, the invention is not limited to a film-forming system of this type. The invention can be applied to a film-forming system having a heating resistor and a film-forming system using plasma. Further, it can be applied to other various processing systems such as an oxidation-diffusion system, an etching system and an annealing system. Still further, the invention can be applied to an exhaust system, such as a load lock, for use in a processing system. Further, an object to be processed is not limited to a semiconductor wafer. An LCD substrate, a glass substrate, etc. can also be processed.

As explained above, according to the processing system of the present invention, it is possible to exhibit the following excellent operation effects.

According to the present invention, as the particle-measuring system is installed on the exhaust pipe at the upstream of the vacuum pump, the distance of the gas flowing route between the processing chamber and the particle-measuring system is very short.

Therefore, unlike the conventional processing system, it is possible to avoid measuring abnormalities that fall from the inner walls of the pipes, blades of the vacuum pump and walls. Instead, it is possible to obtain a high correlation between the actual number of particles within the processing chamber and the values measured by the particle-measuring system.

Further, when the irradiation direction of the laser beams L is set to follow the direction connecting between the center point of the exhaust pipe and the center axis of the processing chamber, it is possible to irradiate the laser beams onto the portion where the density of the particles is high. Therefore, it is possible to grasp an accurate volume of particles, with a further increased correlation.

Further, when the center of the scattered light detector is offset in a predetermined direction by a predetermined distance from the center point of the cross section of the exhaust pipe, namely, in a radial outside direction away from the center point or on the wall side, it is possible to direct the center of the scattered light detector to a portion where the density of the particles is high. As a result, it is possible to further increase the correlation.

Further, when the laser beams are transmitted to a position offset by a predetermined distance from the center point of the cross section of the exhaust pipe in a specific direction, namely, in the radial outside direction away from the center point or on the wall side, it is possible to irradiate the laser beams L to a portion where the density of the particles is high. As a result, it is possible to increase the correlation.

Figure 13:
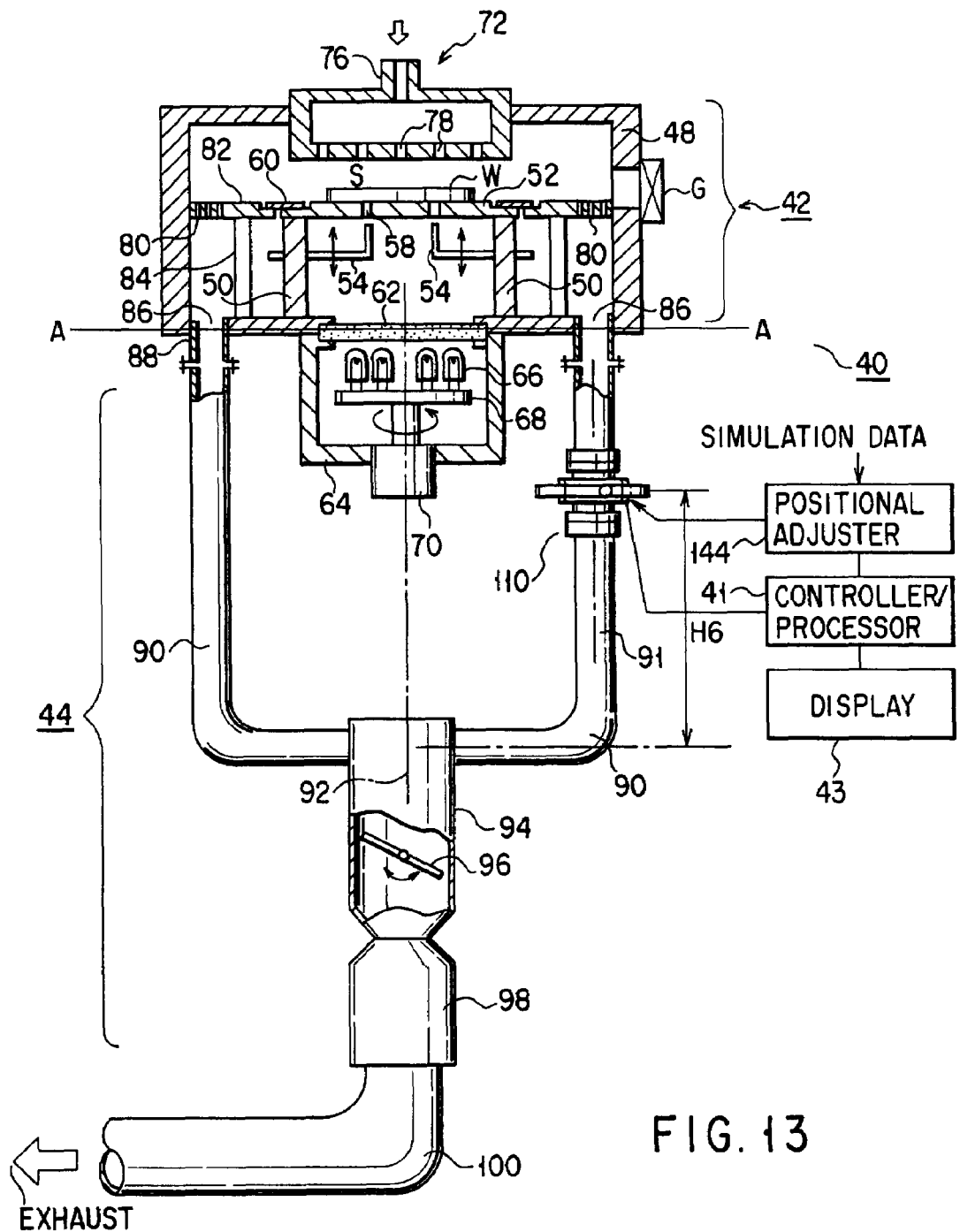
FIG. 13 is a configuration diagram showing a processing system on which a particle-measuring system relating to a second embodiment of the present invention is mounted.

FIG. 13 shows an example of a configuration of a particle-measuring system that can rotate around the piping installed, as a second embodiment of the present invention. In the configuration shown in FIG. 13, portions equivalent to those in FIG. 1 are attached with identical reference numbers, and their detailed explanation will be omitted.

A particle-measuring system 110 is installed on an exhaust pipe 90 in a similar manner to that of the particle-measuring system 46.

Figure 14A:
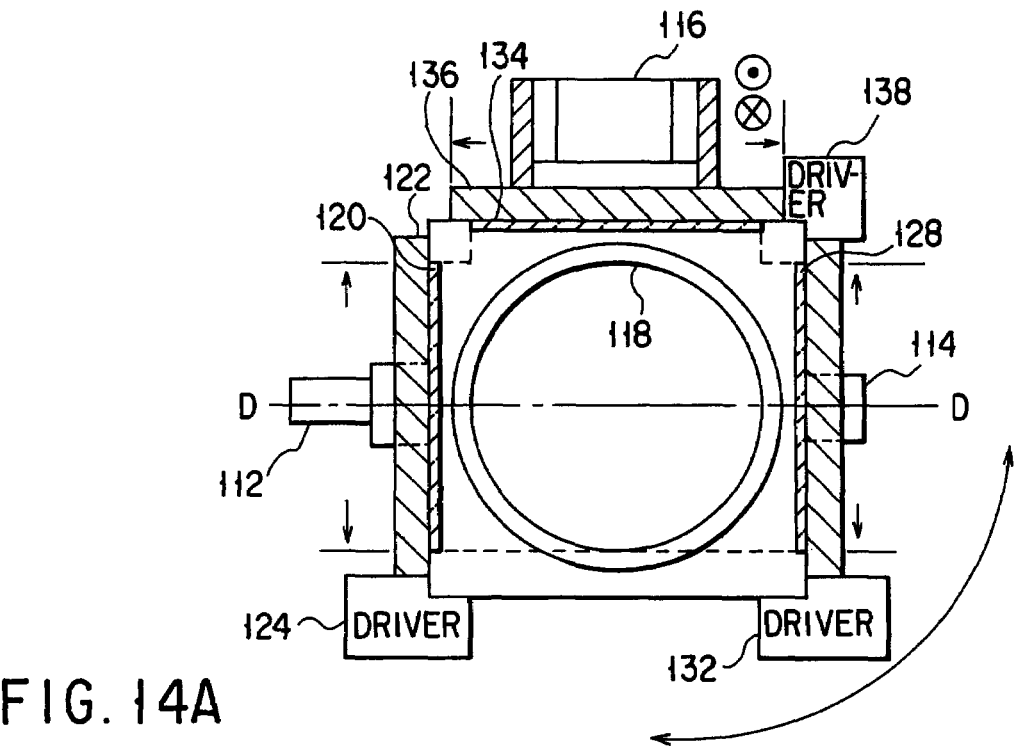
FIG. 14A and FIG. 14B are diagrams showing detailed constructions of the particle-measuring system relating to the second embodiment of the present invention.
Figure 14B:
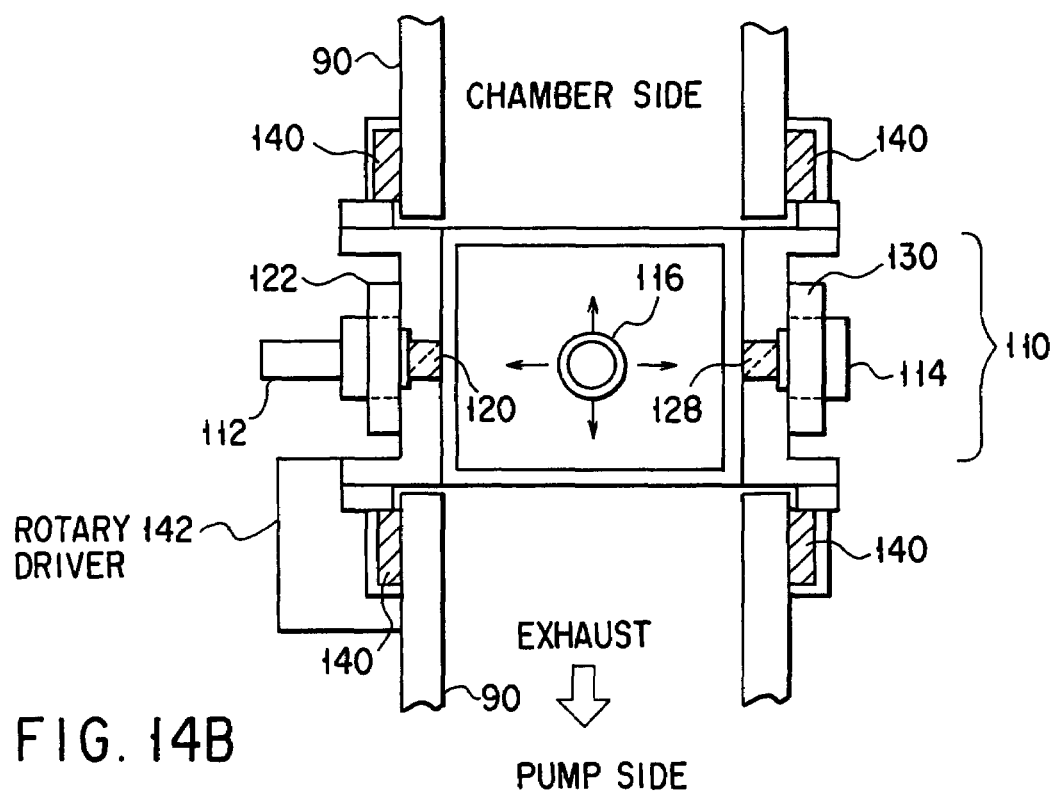

This particle-measuring system 110 consists of a stopper member 114 disposed opposite to a laser beam irradiator 112, and a scattered light detector 116 made of a light-receiving element or the like provided on the pipe wall in a direction approximately orthogonal with an irradiation direction of laser beams L, as shown in FIG. 14A. FIG. 14B is a diagram showing a configuration of a cross-sectional surface of the particle-measuring system 110 cut along a line D-D in FIG. 14A.

This laser beam irradiator 112 is disposed at the outside (atmosphere side) of a window 120 made of a transparent material provided in airtight in a radial direction of a manifold 118. A guiding mechanism 122 is provided along the window 120. The laser beam irradiator 112 is moved within the guiding mechanism 122 by a driver 124 having a motor or a linear motor.

The manifold 118 is formed using one of stainless steel, aluminum, aluminum alloy, or aluminum or aluminum alloy of which surface has been alumite processed. The window 120 is made of quartz glass or corrosion-proof sapphire glass or the like. Windows to be described later are also made of a similar material.

The stopper member 114 is also disposed at the outside of a window 128, and is always moved by a driver 132 having a motor or a linear motor to a position where laser beams irradiated by the laser beam irradiator 112 are received along a guiding mechanism 130.

The scattered light detector 116 is also moved in two-dimensional directions (up/down and left/right directions) so as to be basically in a position orthogonal with a direction of laser beams irradiated by the laser beam irradiator 112 at the outside of a window 134 provided on the manifold 118. The scattered light detector 116 is also moved to a position not orthogonal with laser beams in order to measure the number of particles at a position where the density of particles is high. The scattered light detector 116 is moved in two-dimensional directions on the window 134 by a driver 138 having a motor or a linear motor in an area encircled by a guiding mechanism 136.

As shown in FIG. 13, the particle-measuring system 110 is constructed to rotate along a radial direction of the exhaust pipe 90. Specifically, known magnetic fluid vacuum seals 140 for maintaining a vacuum state are disposed on both-end flanges, and each magnetic fluid vacuum seal 140 is fitted with the particle-measuring system 110 so as to be rotatable around the exhaust pipe 90. A rotary driver 142 executes this rotation. For example, this rotation may be carried out as follows. A gear is provided at the side of the exhaust pipe 90. A motor is connected to this gear to have an engagement with this gear. Thus, the whole particle-measuring system 110 is rotated based on the rotation of the motor. Alternatively, the particle-measuring system 110 may be rotated by magnetic force of a magnet.

For carrying out a positional adjustment of the laser beam irradiator 112, the stopper member 114 and the scattered light detector 116 respectively, a position sensor not shown is provided for each unit to detect positions. A position adjuster 144 drives each driver according to a detected position signal. Data based on a simulation may be input to this position adjuster 144 to retrieve an optimum point.

One example of a particle distribution state according to the computer simulation will be explained with reference to FIG. 15.

This simulation shows an example of exhausting a process gas of $WF_6$/DCS/Ar:4/150/450 sccm in a WSi process, with 0.7 Torr (93.3 Pa) for an internal pressure of the chamber by taking the weight into consideration. This shows a state of a result of data that a distance H3 from the center of a bent exhaust pipe connected to an assembling pipe is 300 mm.

As shown in FIG. 16, the data of this simulation is input to the position adjuster 144 to drive each driver. In this example, the laser beam irradiator 112 and the stopper member 114 are moved so that the laser beams of the laser beam irradiator 112 pass through the area in which the density of particles is highest. The scattered light detector 116 is moved to a position orthogonal with the laser beams.

The controller/processor 41 controls the laser beam irradiator 112 and the scattered light detector 116 to input measured data of particles and carry out an arithmetic processing. The control and process section 41 may be provided in or outside the system control section that controls the entire processing system. The display 43 is provided to make a display of processing results and expressions and various parameters to be used for simulations.

For example, it is possible to control and manage the controller/processor 41 and the position adjuster 144 by software by connecting these units to a user-operable controller such as a personal computer not shown.

Depending on the shape of the exhaust pipe, and also when there is a mounting table or an exhaust porous plate in front of the exhaust opening to hinder the flow of a gas, these obstacles affect the gas flow distribution within the exhaust pipe, and also affect the particle density.

Therefore, according to the present embodiment, a simulation is carried out based on parameters relating to the processing unit and the manufacturing process. Based on a result of data obtained from the simulation, the position adjuster 144 automatically moves the laser beam irradiator 112, the stopper member 114, and the scattered light detector 116, thereby to irradiate laser beams to a portion where the density of particles is the highest. Thus, the number of particles can be measured in a satisfactory condition. Particularly, it is possible to carry out a simulation and an actual measurement according to a kind of particles, or a kind of an exhaust gas including these particles, or a speed of exhausting the gas. As a result, it is possible to set an optimum measuring position.

Therefore, it is possible to find an optimum measuring point based on actual situation of measuring instead of the measuring at a constant design time. Thus, it is possible to obtain high degree of freedom of measuring and to achieve accurate measuring.

Figure 21:
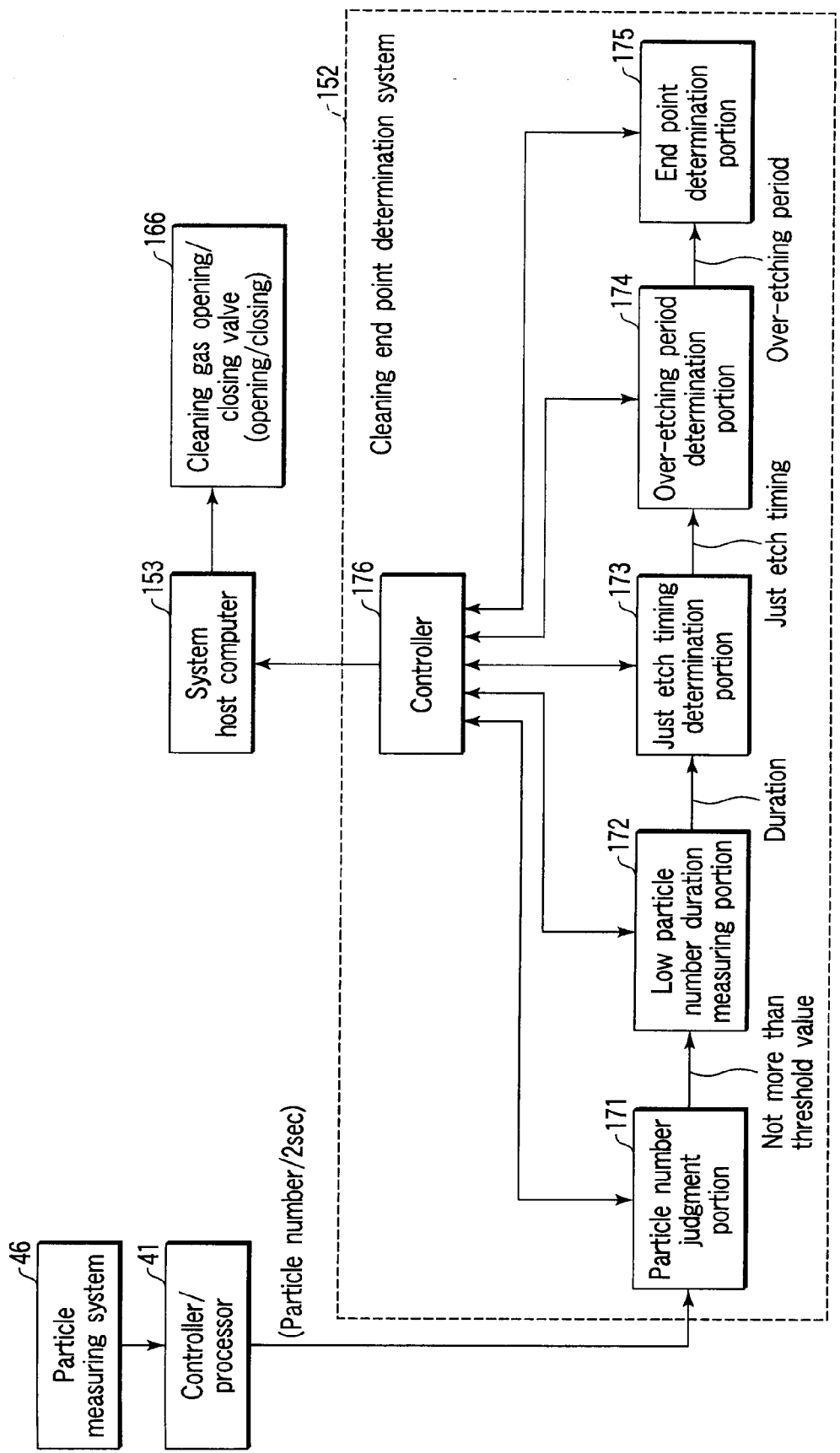
FIG. 21 is a block diagram showing a cleaning end point determination portion.
Figure 22:
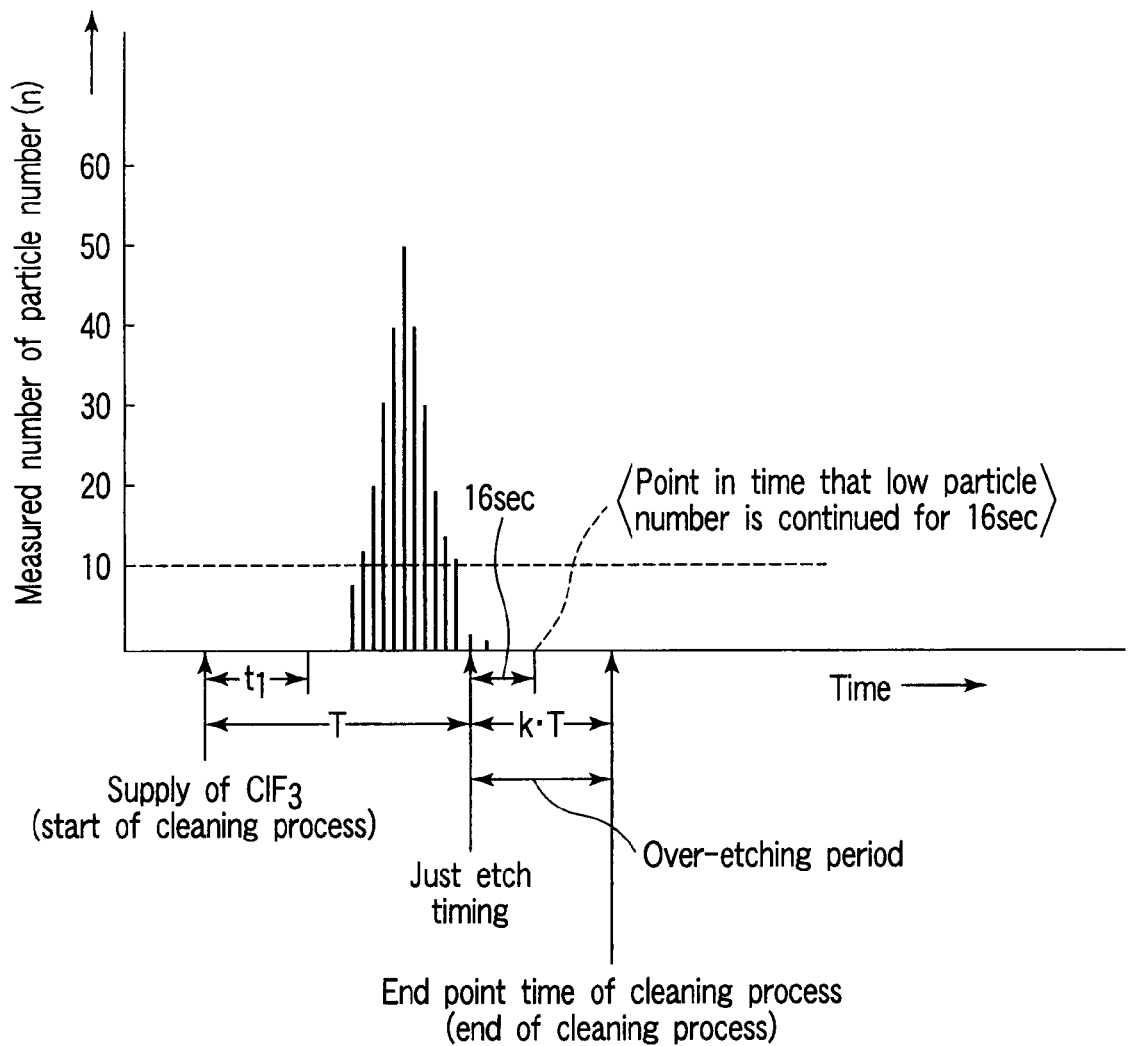
FIG. 22 is an explanatory view for illustrating a principle of determining an end point of cleaning processing.

FIG. 20 is a view showing a structural example of a processing system according to a third embodiment having a particle measuring portion mounted thereon, FIG. 21 is a block diagram showing a cleaning end point determination portion, and FIG. 22 is an explanatory view for illustrating the principle of determining an end point of the cleaning processing. In description of this embodiment, like reference numerals denote constituent parts shown in FIGS. 20 and 21 which are equivalent to those depicted in FIG. 1, thereby omitting the detailed explanation thereof. Further, reference is made to the positional relationship between a transmission window and an exhaust opening in the processing chamber shown in FIG. 2 and an attachment state of the particle measuring portion illustrated in FIG. 3.

In the third embodiment, description will be given taking a CVD system as an example of the processing system. Naturally, this can be likewise applied to all processing systems that require cleaning processing using a sputtering device, an etching device and others. Furthermore, although reference is made to a system having a structure as disclosed in Japanese patent application laid-open No. 2001-59808 proposed by the present applicant as a concrete example of a CVD system and particle measuring portion, this is equivalent to the first embodiment mentioned above except for the structures of a gas introducing system and a wafer attachment system.

As shown in FIG. 20, this CVD system 151 is roughly constituted by a processing unit 42 which performs film-forming processing to a wafer W and an exhaust system 44 which exhausts an atmosphere or a film-forming gas in the processing unit 42.

There is provided a particle measuring system 46 which measures the number of particles in the exhaust gas flowing through the exhaust gas 44. This particle measuring system 46 is controlled by a controller/processor 41. This controller/processor 41 may be incorporated in a system control portion (not shown) which controls the entire processing system or may be an independent device. Moreover, a later-described cleaning end point determination system 152 is connected to this particle measuring system 46.

An annular reflector 50 having the inner surface mirror-finished with a material which reflects a heat ray is arranged below the inside of the processing chamber 48 of the processing unit 42. A support column 84 is provided on the outer periphery of the reflector 50, and a mounting table 52 which attaches the wafer W is supported above this column through an attachment 60. Lifter pins 54 (only two are shown in the illustrative example) which lift up the wafer W from the lower surface thereof are arranged below the mount base 52 through lifter pin holes 50 and they are driven up and down by a non-illustrated drive system. This wafer W is transferred between a carriage mechanism having a non-illustrated arm, etc., and the mounting table 52 and carried into or from the processing chamber.

One end of an integral rod-shaped clamp support portion 155 is attached to the lifter pin 54. A clamp ring 156 is attached to the other end of the clamp support portion 155, and the peripheral edge portion of the wafer W is pushed and fixed so as to be appressed against the mounting table 52. A space between the processing space S and the lower side of the mounting table 52 becomes substantially airtight, and the wraparound of the film-forming gas to the back side of the wafer W or the back side of the mounting table 52 can be avoided, thereby preventing an unnecessary film from being formed.

In addition, a heating chamber 64 is provided on the bottom of the processing chamber directly below the mounting table 52 through a transmission window 62. A plurality of heating lamps 66 are attached to a rotary table 68 which also serves as a reflecting mirror in the heating chamber 64. This rotary table 68 is rotated by a motor 70. This rotation can uniformly heat the back side of the wafer W. It is to be noted that a resistance heater as a heating source may be embedded in the mounting table 52.

Additionally, a shower head portion 157 having many gas injection holes 158 formed thereto is provided to a processing chamber ceiling portion opposite to the mounting table 52. This shower head portion 157 is molded into a circular box shape by using, e.g., aluminium.

This shower head portion 157 is connected to a non-illustrated gas introducing system and has gas introducing openings 159, 160 and 161 for supplying the gasses provided thereto. Further, the film-forming gasses supplied from each of the two gas introducing openings 159 and 160 of these openings are mixed in a gas mixing portion 162 by rectification plates 162a, 162b and 163c laminated in the form of three layers, and led into a diffusion chamber 163 below the gas mixing portion 162.

Furthermore, a diffusion plate 164 having many diffusion holes is provided in the diffusion chamber 163, and the introduced mixed gas is diffused. Moreover, a cleaning gas supply pipe 165 is connected to the remaining gas introduction opening 161. The cleaning gas supply pipe 165 may be used by being commonly connected to one of the gas introducing openings 159 and 160 through a valve. This cleaning gas supply pipe 165 is connected to a flow rate controller 167 through an opening/closing valve 166. In the cleaning processing, a cleaning gas, e.g., a $ClF_3$ gas is caused to flow. Each gas supplied from each of the gas introducing openings 159, 160 and 161 of the shower head portion 157 flows into the diffusion chamber 163 in the shower head portion 157, is diffused by the diffusion plate 164, introduced into the gas diffusion chamber 168 from a gas discharge hole 164a formed in the diffusion plate 164, and diffused and injected into the processing space S from a plurality of gas injection holes 158 formed in a shower plate 169.

Figure 37:
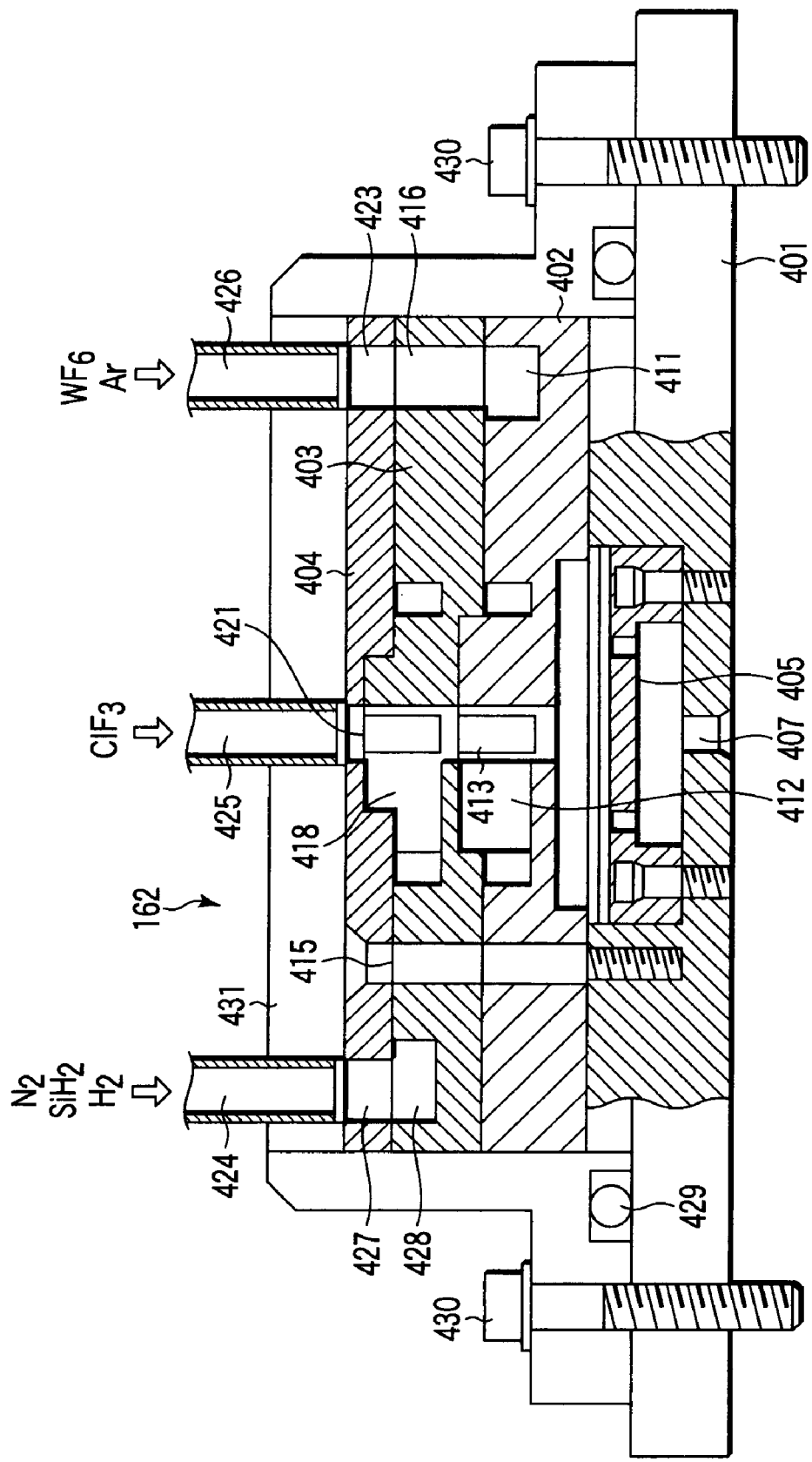
FIG. 37 is a cross-sectional view showing a structure inside a casing 431 of a gas introducing portion.

As shown in FIGS. 36 and 37, the shower head portion 157 which introduces the process gas is arranged on the upper portion of the processing chamber. The shower head portion 157 is constituted by a non-illustrated shower base, a gas introducing plate 401, a shower plate 169 and a non-illustrated gas mixing portion 162.

The gas mixing portion 162 which introduces the process gas is connected to the upper side of the gas introducing plate 401 arranged at the lowermost end, and the gas introducing plate 401 thereof is connected so as to be fitted to the upper part of the shower base on the inner peripheral side.

A concave portion 409 is formed at the center of the gas introducing plate 401, and a rectification plate 405 having a cylindrical shape with a lid fitted to the upper part of the gas introducing plate 401, a lower plate (rectification plate 163c), a middle plate 403 (rectification plate 162b) and an upper plate 404 (rectification plate 162a) are provided so as to be fitted in a casing 431. As shown in FIG. 37, the gas introducing plate 401 and the casing 431 are fastened by a plurality of bolts 430 through a sealing member 429 and air-tightly fixed. The upper part of the casing 431 has gas introducing openings 424, 425 and 426.

FIG. 37 is a cross-sectional view showing a structure of the inside of the casing 431 of the gas introducing portion. To the upper plate 404 are provided a duct 421 which communicates with the cleaning gas introducing opening 425 of the casing 431, a duct 427 which communicates with the first main gas introducing opening 424 of the casing 431, and a duct 423 which communicates with the second process gas introducing opening 426 of the casing 431.

The duct 427 which communicates with the first process gas introducing opening 424 communicates with a groove 418 formed at the center of the middle plate 403 through a groove 415 provided at a semi-circumferential portion of the middle plate 403 on the outer peripheral side, and slits are formed in a plurality of vertical directions to a convex portion 417 which protrudes so as to facilitate mixing the gas in the groove 418, and they continuously communicate with the duct 421 of the upper plate 404 and the grooves 418 and 412 of the middle plate 403 and the lower plate 402.

In addition, the duct 423 communicating with the second process gas introducing opening 426 communicates with a groove 412 formed at the center of the lower plate 402 through a groove 411 provided at the semi-circumferential part of the lower plate 402 on the outer peripheral side via the duct 416 provided to the middle plate 403, slits are formed in a plurality of vertical directions to a convex portion 413 which protrudes so as to facilitate mixing of the gas in the groove 412, and they communicate with a space between the lower plate 402 and the rectification plate 405.

This space communicates with the main gas duct 407 through a space 409 formed by the gas introducing plate 401 and the rectification plate 405 via an open hole 410 of the rectification plate 405. With such a structure, an $H_2$ gas and a $WF_6$ gas or the like are sufficiently mixed in the groove 412, and the mixed gas is uniformly supplied into the processing chamber 48 from the shower head portion 157 through the process gas duct 407.

Additionally, a cavity may be provided to the upper plate 404 so as to communicate with the outer peripheral side of the shower plate 169 so that the $H_2$ gas is supplied from a peripheral gas introducing hole to the periphery. In the gas mixing portion 162, when $H_2$, $SiH_4$ and $N_2$ gasses are supplied to the first process gas introducing opening 424 and $WF_6$, and Ar and the like are supplied to the second process gas introducing port 426, these gasses are mixed and are supplied from the main gas duct 407 into the shower head portion 157 as described in connection with FIG. 37. Further, the $ClF_3$ gas supplied to the cleaning gas introducing opening 425 is supplied into the shower head portion 157 through the cleaning gas duct 418 formed at the center of the upper plate 404 and via the slits of the convex portion 417 of the middle plate 403, the slits of the convex portion 413 of the lower plate 402 and the main gas duct 407.

Then, the first and second process gasses supplied to the main gas duct 407 are mixed, diffused in a second space portion 168 after passing through a plurality of gas discharge openings formed in the rectification plate 164 from the first space portion 163 in the shower head portion 157, and uniformly discharged toward the wafer W from the plurality of gas discharge holes 158 formed in the shower plate 169. Furthermore, the cleaning gas $ClF_3$ gas used to remove an unnecessary film adhered to the inner wall and the like of the processing chamber 48 is supplied to the cleaning gas duct 418 and, like the process gas, passes through a plurality of gas discharge holes formed in the rectification plate 164 from the first space portion 163 in the shower head portion 157, is diffused in the second space portion 168, discharged from the plurality of gas discharge holes 158 formed in the shower plate 169 and removes the unnecessary film which has adhered in the processing chamber.

Each gas is uniformly diffused in the second space portion by increasing the pressure in the first space portion 163 more than that in the second space portion 168 and reducing the conductance of the rectification plate 164 less than that of the shower plate 165.

Moreover, a rectification plate 82 is provided on the outer peripheral side of the mounting table 52. The rectification plate 82 has a ring-like shape and a plurality of rectification holes 80 formed thereto and is supported in the vertical direction by an annular support column 84. In addition, a through hole 84a is opened on the side wall of the support column 84, and a relief valve 168 is attached so as to cover the through hole 84a, thereby adjusting the pressure between the upper and lower parts of the wafer W in the chamber. This pressure adjustment prevents jounce of the wafer W from being generated due to the pressure difference between the pressure under the mounting table 52 and the processing space S when carrying in/out the wafer W. Additionally, a plurality of exhaust openings 86 are provided on the bottom of the chamber below the rectification plate 82.

As shown in FIG. 20, four exhaust openings 86 are arranged at substantially even intervals along the circumferential part of the bottom, and exhaust ports 88 are provided for each exhaust opening 86.

Further, the exhaust openings 86 may be provided at the center of the bottom of the processing chamber 48.

These exhaust ports 88 are air-tightly connected to the respective exhaust pipes 90. Like the first embodiment, one or a plurality of exhaust pipes 90 are used to provide a particle measuring system 46 in the middle of the route to a collecting pipe 100.

A film-forming process using the CVD system will now be described.

The film-forming process is substantially equivalent to that of the first embodiment mentioned above, and description will be given to parts having different effects in this embodiment but description on other parts will be simplified.

The wafer W is delivered into the lifted lifter pin 54 in the processing chamber 48 by a non-illustrated carrying arm from an opened gate valve G, the carrying arm is then retracted, and the gate valve G is closed.

Also, the lifter pin 54 is moved down and the wafer W is mounted on the mounting table 52. Further, the outer peripheral edge part of the wafer W is pressed with the inner peripheral edge part of the clamp ring 156. Thereafter, the air in the processing chamber 48 is exhausted by the exhaust system 44. At this moment, the relief valve 168 is actuated and a difference between the pressure below the mounting table 52 and the pressure on the wafer W side is decreased. As a result, jounce of the wafer W generated in exhaust is avoided, and occurrence of particles is restricted.

Then, various kinds of gasses for the process gas are introduced into the processing chamber 48, the exhaust system 44 is adjusted to set a predetermined degree of vacuum, and a temperature of the wafer W is increased to a predetermined value, e.g., 350 to 700° C. and maintained by a heating lamp 66 which rotationally moves. As a result, a predetermined chemical reaction occurs in the film-forming gas, and a thin film is deposited and formed on the surface of the wafer W.

In this structure, the particle measuring system 46 measures the number of particles included in the exhaust gas which passes through the exhaust pipe 90.

When a process of the wafer W is continuously or intermittently carried out, a command to perform the cleaning process is issued from a system host computer 153 in accordance with a predetermined cleaning schedule.

This cleaning process is carried out by introducing the $ClF_3$ gas into the processing chamber 48 through the cleaning gas supply pipe 165. As a result, an unnecessary film which has adhered to the inner wall of the processing chamber 48 or the internal structure in the chamber, e.g., the surface of the mounting table 52, the clamp ring 156, the shower head portion 157, etc., is removed. Furthermore, in order to obtain the just etch in the above-described cleaning process and determine the end point even in the middle of the cleaning process, the number of particles included in the exhaust gas is measured by the particle measuring system 46.

Description will now be given as to the particle measuring system 46 and the cleaning end point determination device 152.

As shown in FIG. 3, this particle measuring system 46 is constituted by a laser beam irradiator 102, a stopper member 104 and a scattered light detector 106. As a laser element in the laser beam irradiator 102, a semiconductor laser element such as a minimized GaAlAs or the like is used, and an output of several W to several tens of W is preferable as an output therefrom. It is to be noted that a YAG laser with a high output can be used as the semiconductor laser element.

Although a laser beam L emitted by this laser bean irradiator 102 is emitted at the center of the cross section of the exhaust pipe 90, it is preferably emitted so as to be parallel to a line segment connecting the center point O of the cross section and the central axis of the chamber 92 as shown in FIG. 3 like the first embodiment mentioned above. Moreover, the scattered light detector 106 is provided on the pipe wall in a direction substantially orthogonal to the irradiation direction of the laser beam L, and it receives the scattered lights SL generated when the laser beam L is emitted on the particle P.

This scattered light detector 106 outputs a detection signal to the controller/processor 41. This controller/processor 41 counts the number of particles per unit time. As this unit time, 0.1 seconds or above can be set, but 2 seconds is set in this example. When the unit time is set to 2 seconds, the number of particles is measured every 2 seconds. Of course, this unit time can be freely set according to need. The number of particles obtained every 2 seconds is outputted to the cleaning end point determination portion 152 as a measured value.

The cleaning end point determination device 152 outputs a direction of the end point to the system host computer 153 which controls the entire CVD system. The system host computer 153 controls, e.g., an opening/closing valve 166. It is to be noted that a control system having a parameter to be controlled incorporated therein in advance may be provided in place of the system host computer 153. As to this parameter, constituent parts such as a film thickness measurement, a pressure gauge, a film-forming gas density and component and a film quality measurement can be provided and an optimum film forming method can be carried out based on the respective measurement results.

Then, the cleaning end point determination device 152 will now be described with reference to FIGS. 21 and 22.

As shown in FIG. 22, when the $ClF_3$ gas is introduced into the processing chamber 48 and the cleaning process is started, a large quantity of particles due to etching is generated after a while and exhausted to the exhaust pipe 90 together with the gas. Then, at a point in time the number of particles is reduced to substantially a few, this is the just etch timing, as will be described later. This timing is automatically detected, and the end point of the cleaning process is determined based on this.

As shown in FIG. 21, the cleaning end point determination device 152 is constituted by a particle number judgment portion 171, a low particle number duration measuring portion 172, a just etch timing determination portion 173, an over-etching period determination portion 174, an end point determination portion 175 and a control portion 176 each of which will be described later.

The above-described controller/processor 41 measures the number of particles at intervals of, e.g., 2 seconds as a unit time in this embodiment. Naturally, the unit time can be appropriately set in accordance with situations and the like. The obtained measured value is outputted from the controller/processor 41 to the particle number judgment portion 171.

The particle number judgment portion 171 receives the measured value from the controller/processor 41 and judges whether this measured value is not more than a predetermined judgment value, e.g., 10/2 seconds. It is to be noted that this judgment value is not restricted to a particular value and an arbitrary value can be appropriately set. Incidentally, the size of the particle to be measured can be selected within a range of not less than 0.001 μm in many ways by selectively setting a parameter by the controller/processor 41.

The judgment result is inputted to the low particle number duration measuring portion 172 on the next stage. This low particle number duration measuring portion 172 measures a time during which the state that the number of particles is not more than the judgment value, e.g., 10 is continued, and outputs the measured result (duration) to the just etch timing determination portion 173.

Then, the just etch timing determination portion 173 determines the just etch timing based on the inputted duration. As shown in FIG. 22, this determination decides whether the duration of the low particle number is continued for a predetermined threshold value, e.g., 16 seconds (corresponding to 8 unit times with respect to the unit time mentioned above) or above. When the duration reaches this threshold value or above, a point in time obtained by tracing back for the time of the threshold value, i.e., 16 seconds from that moment is determined as a just etch time. It is to be noted that a point in time when the time of the threshold value, i.e., 16 seconds has passed may be determined as the just etch time. Incidentally, 16 seconds as the threshold value is just an example, a range of, e.g., 1 to approximately 300 seconds is assumed, and the threshold value can be appropriately set from this range. Of course, the threshold value is not restricted to this range.

In addition, the over-etching period determination portion 174 determines an over-etching period to be subsequently carried out based on a cleaning process period T from the start of etching to the just etch timing. This over-etching period determination portion 174 determines an over-etching period by multiplying the cleaning process period T by a predetermined coefficient k. Although this coefficient k is predetermined based on cleaning conditions, such as the type of deposited film, temperature, quantity of flow of the cleaning gas and others, a range of approximately 0.1 to 1 is usually assumed, and it preferably falls within a range of 0.2 to 0.6. Here, the coefficient k is set to, e.g., k=0.5.

Additionally, the end point determination portion 175 determines the finish time of the over-etching period as an end point (finish time) of the cleaning process. That is, the time obtained by adding the over-etching period (k·T) to the time of the just etch timing is the cleaning process finish time. In order to stop supply of the cleaning gas when the end point is reached, the system host computer 153 performs control to close the opening/closing valve 66. This cleaning end point determination device 152 is constituted by, e.g., a microcomputer and the like, and the operation of each constituent part is controlled by the controller 176 in accordance with a predetermined program.

As shown in FIG. 22, although particles are hardly generated for a while after starting supply of the ClF$_3$ gas which is the cleaning gas, the operation to determine the end point of the cleaning process mentioned above is controlled to be started after the particle number higher than a threshold value of the particle number is once detected. Here, referring to FIGS. 23A and 23B in which the correlation between the just etch timing and increase/decrease in the particle number is actually examined, the experiment results will now be described.

FIG. 23A shows increase/decrease in the particle number when performing the cleaning process after carrying out the film-forming process of a WSi film to five wafers, and FIG. 23B shows increase/decrease in the particle number when performing the cleaning process after carrying out the film-forming process of the WSi film to 25 semiconductor wafers. However, in these drawings, scales of the vertical axis are different. Further, a numeric figure of the time in the horizontal axis represents hours, minutes and seconds.

Here, ClF$_3$ gas is used as the cleaning gas, and the just etch timing is determined by visually confirming a change in color of the mounting table. That is, a point in time when the surface of the mounting table in the processing chamber is observed from an observation window on the chamber wall and a color of the surface of the mounting table is changed is determined as the just etch timing.

As shown in FIGS. 23A and 23B, when the ClF$_3$ gas is supplied into the processing chamber 48 and the cleaning process is started, the particles are hardly generated for approximately 50 seconds. This can be considered as a time lag until the cleaning gas is introduced into the processing chamber 48 after the opening/closing valve 166 (see FIG. 21) for the cleaning gas is "opened".

Then, the particles are suddenly generated when approximately 50 seconds pass, and they are then decreased after a peak is once reached. At this moment, in case of processing the 25 wafers shown in FIG. 23B, a large peak value is once suddenly detected. Thereafter, the particles are greatly reduced for approximately 10 seconds, and the particle number is again increased and a second peak is reached. After this peak, the particle number is gradually decreased.

In this manner, a measuring pattern differs depending on a thickness of an adherent film. Here, in the etch timing determination portion 174, as described in connection with FIG. 21, a point in time when the detection state that the particle number per unit time (2 seconds) is not more than 10 is continued for 16 seconds is determined as a just etch timing, for example. Therefore, this just etch timing is the time obtained by tracing back from that moment.

As a result, in FIG. 23A, the time of the just etch timing is after elapse of 57 seconds from start of cleaning in the case of visual confirmation, and it is after elapse of 54 seconds in the case of the particle measuring system 46, and their difference is just 3 seconds. Furthermore, in FIG. 23B, the time of the just etch timing is after elapse of 135 seconds from start of cleaning in the case of visual confirmation, and it is after elapse of 134 seconds in the case of the particle measuring system 46. Their difference is just 1 second, the substantial correlation is obtained based on this.

As described above, the just etch timing determined by using the parameter measuring system 46 is substantially the same as that determined by visual confirmation, and it can be confirmed that the just etch timing is appropriately and automatically determined. That is, the time at which the particles are generated due to etching after introducing the cleaning gas can be measured irrespective of an accumulation number of wafers processed in the processing chamber, and the over-etching timing can be automatically and correctly determined.

Therefore, by applying the over-etching process in the calculated over-etching period with the just etch timing being determined as a start time, an appropriate cleaning process can be realized. That is, the appropriate cleaning process can be constantly executed by performing setting in the system host computer or an APC (Advance Process Control) control system in advance without effecting the operation and the like by an operator, irrespective of the number of wafers processed in the processing chamber 48.

Figure 24:
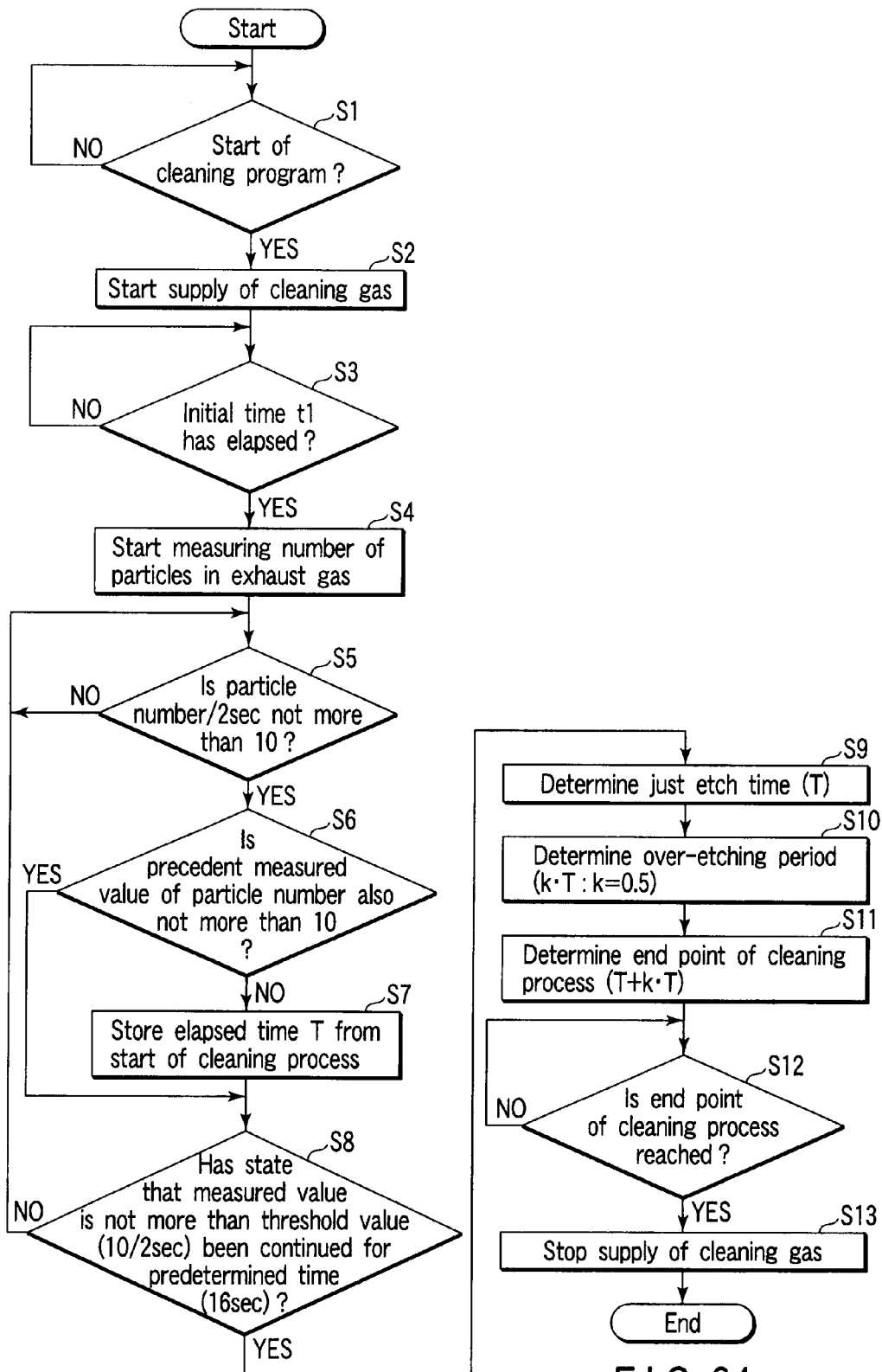
FIG. 24 is a flowchart for illustrating a process of determining an etching end point in time.

The process to determine an etching end point will now be described with reference to FIG. 24.

When a command to start the cleaning process is issued by a non-illustrated host computer and the like, the cleaning program is started (step S1), and supply of the cleaning gas into the processing chamber 48 (see FIG. 20) begins (step S2). With this start, measurement of an elapsed time of the cleaning process begins.

Subsequently, a judgment is made upon whether an initial time t1 (see FIG. 22) has elapsed after start of supply of the cleaning gas (step S3). That is because the particles are not generated immediately after start of supply of the cleaning gas, but the particles are not generated for a while even though the cleaning gas is supplied into the processing chamber, and measurement of the particles in this period is avoided. This initial time t1 is, e.g., approximately 1 to 120 seconds depending on a quantity of the cleaning gas to be supplied and the like. It is to be noted that problems do not occur even if the particle measurement is carried out during this initial time t1 as long as the arithmetic operation is not performed based on a measured value which will be described later.

Moreover, when the initial time t1 has elapsed, measurement of the particle number in the exhaust gas is started by the particle measuring system 46 (step S4). At this moment, namely, at a point in time when the initial time t1 has elapsed, as shown in FIG. 23, a sufficiently large quantity of particles is generated by the cleaning process. Thus, as a measured value of the particle number at this moment, a measured value far greater than 10 which can be assuredly a threshold value is outputted. This measured value is inputted to the particle number judgment portion 171, and a judgment is made upon whether the particle number is not more than 10 (step S5).

Subsequently, a result of this judgment is inputted to the low particle number duration measuring portion 172. When the particle number is not more than 10 (YES), a judgment is made upon whether the particle number of the precedent measured value is also not more than 10 (step S6). On the other hand, if it is not more than 10 (NO), measurement is continued as it is.

If the precedent particle number is not more than 10 (YES) in the judgment at the step S6, the processing advances to a step S7 which will be described later. If the particle number of the precedent measured value exceeds 10 (NO), this means the particle number becomes lower than the threshold value at this moment. Therefore, it is considered that there is the possibility that this point in time becomes the just etch time, and the elapsed time after start of supply of the cleaning gas to a current point in time is stored as a cleaning process period T (step S7). This elapsed time T is updated to a time (period) when the particle number becomes not more than 10 last time if the measured value of the particle number is in the vicinity of 10 which is the threshold value.

Then, a judgment is made upon whether the state that the particle number is not more than the threshold value (10) is continued for a set time (step S8). Here, the set time is set to 16 seconds which is a threshold value. In this judgment, if the low particle number duration that a measured value of the particle number is not more than 10 is 16 seconds or below (NO), the processing returns to the step S5, and measurement of the particle number is continued. In other words, the low particle number duration that the measured value of the particle number is not more than 10 is measured by the low particle number duration measuring portion 172 and the just etch timing determination portion 173 at the steps S5 to S8. On the other hand, if the low particle number duration is continued for the set time (16 seconds) (YES), a point in time obtained by tracing back from that time for 16 seconds is determined as the just etch timing (step S9).

Then, the cleaning process timing to the moment obtained by harking back for 16 seconds becomes the stored time T. It is to be noted that a point in time that the low particle number state is continued for 16 seconds may be set as the just etch timing without harking back 16 seconds as mentioned above. Based on this result, the over-etching period determination portion 174 determines an over-etching period by executing (cleaning process period T×coefficient k) (step S10).

Moreover, based on this over-etching period, the end point determination portion 175 determines an end point of the etching process (etching finish time) (step S11). In addition, if this etching point is reached (step S12), supply of the cleaning gas is stopped (step S13), and the over-etching process is terminated. That is, the cleaning process is terminated. It is to be noted that the size of the particles to be measured here can be selected within a range of 0.001 μm or above in many ways by selectively setting a parameter in the controller/processor 41.

As described above, an appropriate and substantially correct just etch timing can be obtained irrespective of the number of wafers processed in the processing chamber 48 before starting the cleaning process. Additionally, an end point of the cleaning process can be determined from this just etch timing. By setting a series of these sequences or a parameter in the system host computer or the APC control system in advance, an adequate cleaning process can be constantly automatically carried out without the operation by an operator. Therefore, damage to the inner wall of the processing chamber or its internal structure can be reduced when carrying out cleaning processing, and the duration of life of the chamber or the internal structure can be prolonged. Further, since only a necessary quantity of the expensive cleaning gas is used, wasteful consumption can be avoided.

In this embodiment, although description has been given as to an example of the WSi film as the unnecessary film which should be removed by the cleaning process, the present invention is not restricted thereto, and the cleaning process method according to the present invention can be applied to any film type. For example, the present invention can be applied to the cleaning process to films of Ti, W, WN, TiN, Ta, TaOx, $SiO_2$, SiN, SiON, TaN, $HfO_2$, $ZrO_2$, $PaO_2$ and the like. Furthermore, the cleaning gas is not restricted to $ClF_3$ gas, and any other cleaning gas such as $NF_3$, ClF, HF and others can be applied to the present invention. Moreover, the present invention can be applied to an end point of plasma cleaning. In addition, the present invention can be applied to an end point of plasma cleaning. As a plasma source, it is possible to apply to a plasma processing system of, e.g., a capacitance type (parallel plate), an ICP, a helicon wave, a micro wave (radial line slot antenna type) and the like. Here, although description has been given to an example of the semiconductor wafer as the object to be processed, the present invention is not restricted thereto, and the cleaning method according to the present invention can be readily applied to a glass substrate, an LCD substrate, a chemical compound semiconductor substrate and the like.

<Continuous Film Formation of Titanium Film and Titanium Nitride Film>

Figure 25:
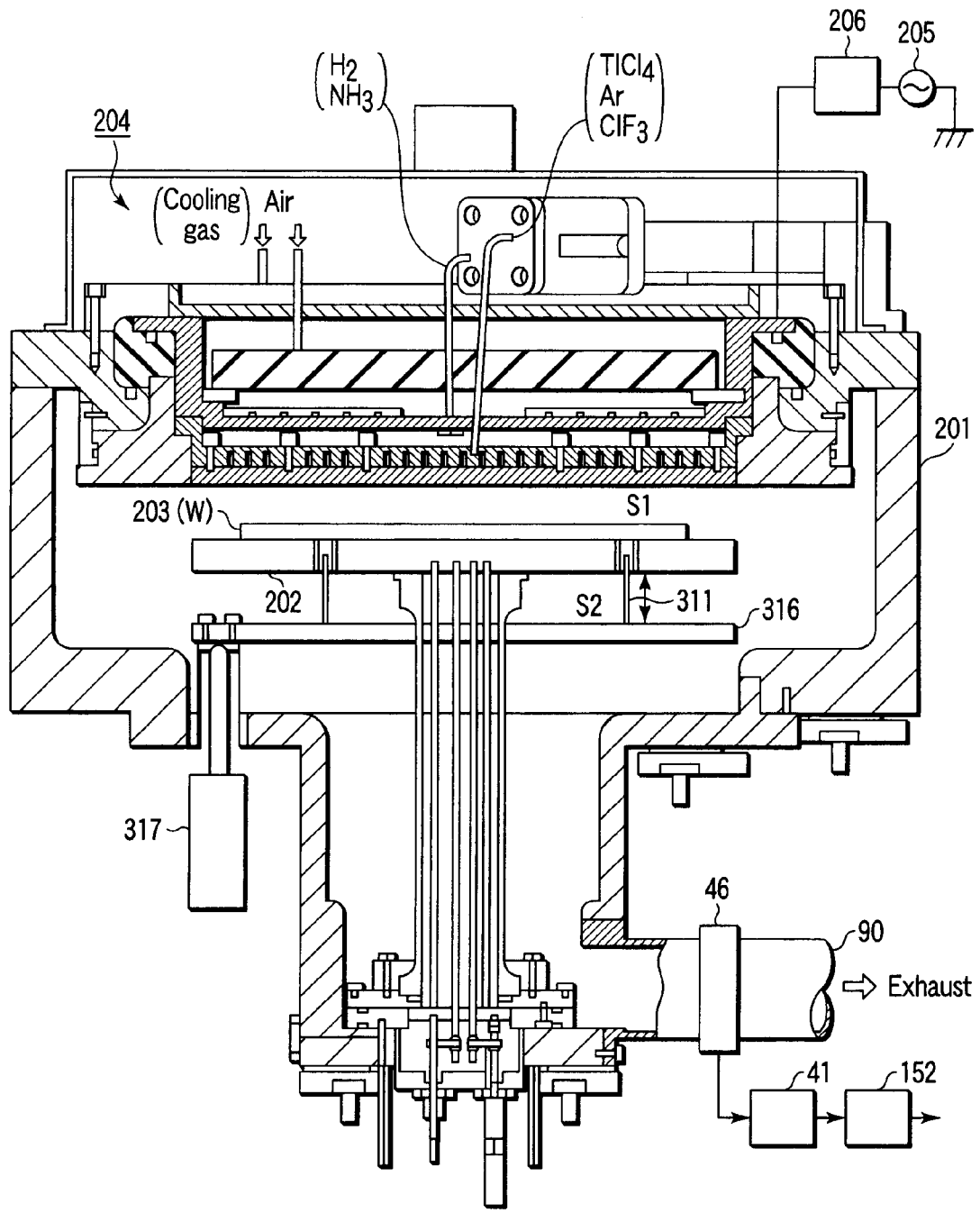
FIG. 25 is a view showing a structural example of a processing system having a push-up pin and its drive mechanism mounted thereon.

Description will now be given as to continuous film formation of a titanium film and a titanium nitride film as a related invention of the present invention with reference to FIG. 25 and FIGS. 26A to 26D. This technique is a related technique of the technique disclosed in Jpn. Pat. Appln. KOKAI Publication No. 10-106974 proposed by the present applicant. FIG. 25 is a view showing a plasma film-forming system, and FIGS. 26A to 26D are process charts showing processes of film formation. Here, description will be given as to a method of continuously forming a titanium film and a titanium nitride film on a substrate surface of an object to be processed, e.g., a semiconductor wafer.

Figure 27:
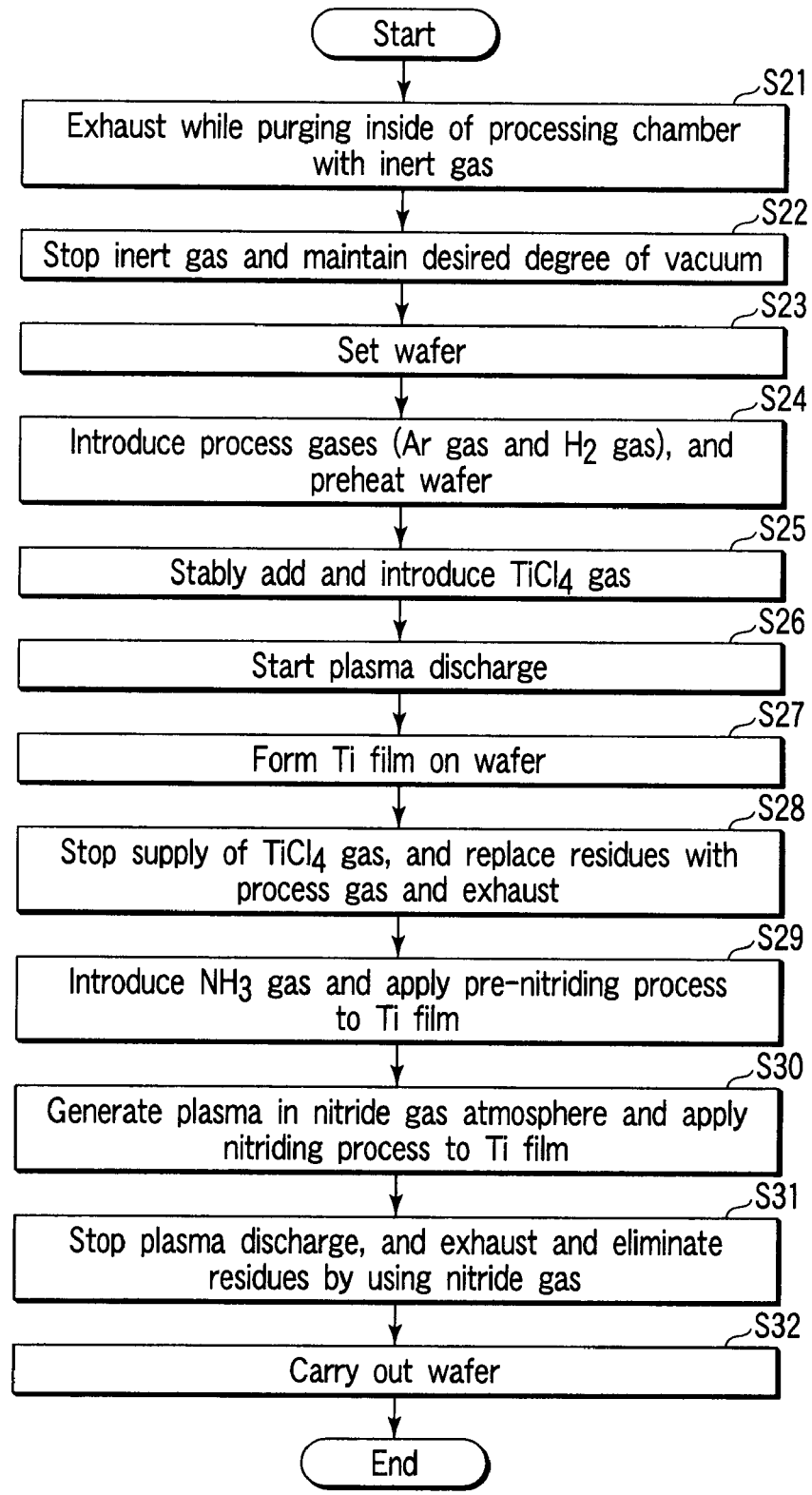
FIG. 27 is a flowchart for illustrating a continuous film-forming method of a titanium film/titanium nitride film as a first example.

A method of forming a titanium film will be first described with reference to a flowchart of FIG. 27.

Exhaust is carried out while purging the inside of the processing chamber with an inert gas (step S21).

Then, when the inside of the processing chamber reaches a desired degree of vacuum, it is maintained (step S22).

A wafer is mounted on the mounting table in the processing chamber through a non-illustrated vacuum load lock mechanism while maintaining the vacuum state (step S23).

Thereafter, the wafer is preheated while introducing a process gas (for example, an Ar gas and an $H_2$ gas) into the processing chamber (the wafer is preheated to the same temperature as that of the film-forming process) (step S24).

Then, the $TiCl_4$ gas is not introduced from the gas supply system into the chamber but caused to flow through an evac line provided as a bypass for a predetermined time. After a quantity of flow is stabilized, a non-illustrated preflow valve is operated, and this gas is introduced into the processing chamber (step S25).

This causes the $TiCl_4$ gas to be introduced into the processing chamber after stabilizing a quantity of flow thereof.

Further, when a quantity of flow of the $TiCl_4$ gas is stabilized at the step S25, the preflow valve is switched, the $TiCl_4$ gas is introduced into the processing chamber, and plasma discharge is started (step S26). At this moment, a time lag until the gas reaches the inside of the processing chamber occurs. However, even if a high-frequency power supply is turned on simultaneously with switching of the preflow valve, a lag of the plasma discharge also occurs since a response of a high-frequency matching device is slow. Therefore, the time lag and the delay of the matching response are canceled out, and the plasma discharge is consequently smoothly started.

However, if the gas line is short and there is no time lag in introduction of the $TiCl_4$ gas into the processing chamber, the timing must be adjusted so as to increase a speed of response of the high-frequency matching device or perform $TiCl_4$ gas introduction adapted for the response of the high-frequency matching device.

With this plasma discharge, a Ti film is formed on the wafer (step S27). Supply of the $TiCl_4$ gas is stopped, residues (film-forming components) in the chamber are exhausted while being replaced with a plasma gas (Ar and $H_2$ gases), the plasma gas being introduced in the chamber (step S28).

Then, an $NH_3$ gas is further introduced into the processing chamber, and the formed titanium film is subjected to a pre-nitriding process (step S29). Thereafter, the high-frequency power supply is turned on, the plasma is generated, and the pre-nitrided titanium film is further nitrided with a nitride gas (Ar, $H_2$ and $NH_3$ gases) (step S30). Then, the plasma discharge is stopped, the nitride gas is introduced continuously, and the residues in the processing chamber are exhausted and removed (step S31). Subsequently, the wafer subjected to a film-forming process is carried to the outside from the inside of the processing chamber (step S32).

As to process conditions of the pre-nitriding process at the step S29, a quantity of flow of the $H_2$ gas is 500 to 4000 sccm, a quantity of flow of the Ar gas is 280 to 2500 sccm, and a quantity of flow of the $NH_3$ gas is 200 to 3000 sccm. Preferably, a quantity of flow of the $H_2$ gas is 1000 to 3000 sccm, a quantity of flow of the Ar gas is 750 to 2250 sccm, and a quantity of flow of the $NH_3$ gas is 650 to 2100 sccm. A ratio of a quantity of flow of the $NH_3$ gas to a total gas flow quantity is 0.026 to 0.8 or, preferably, it is 0.16 to 0.36. A ratio of a quantity of flow of $H_2$ is 0.07 to 0.9 or, preferably, it is 0.18 to 0.68. In addition, a ratio of flow quantity of the $NH_3$ gas to the $H_2$ gas is 0.05 to 3 or, preferably, 0.2 to 2. Furthermore, as to process conditions of the nitriding process at the step S30, the plasma is generated with the same quantity of flow as that at the step S29 and the Ti film is subjected to plasma nitriding. As to film-forming conditions of the Ti film at the step S27, a quantity of flow of $TiCl_4$ gas is 2 to 20 sccm, a quantity of flow of Ar gas is 500 to 10000 sccm, a quantity of flow of $H_2$ gas is 500 to 10000 sccm or, preferably, a quantity of flow of $TiCl_4$ gas is 4 to 16 sccm, a quantity of flow of Ar gas is 800 to 3200 sccm, and a quantity of flow of $H_2$ gas is 200 to 7500 sccm. A ratio of a quantity of flow of $TiCl_4$ gas to a total gas flow quantity is 0.00017 to 0.02 or preferably 0.00037 to 0.0057, and a ratio of a quantity of flow of $TiCl_4$ gas to $H_2$ gas is 0.002 to 0.038 or preferably 0.00053 to 0.008. A titanium (Ti) film with the good quality can be formed by performing the film-forming process with the above-described flow quantity ratios.

Figure 28:
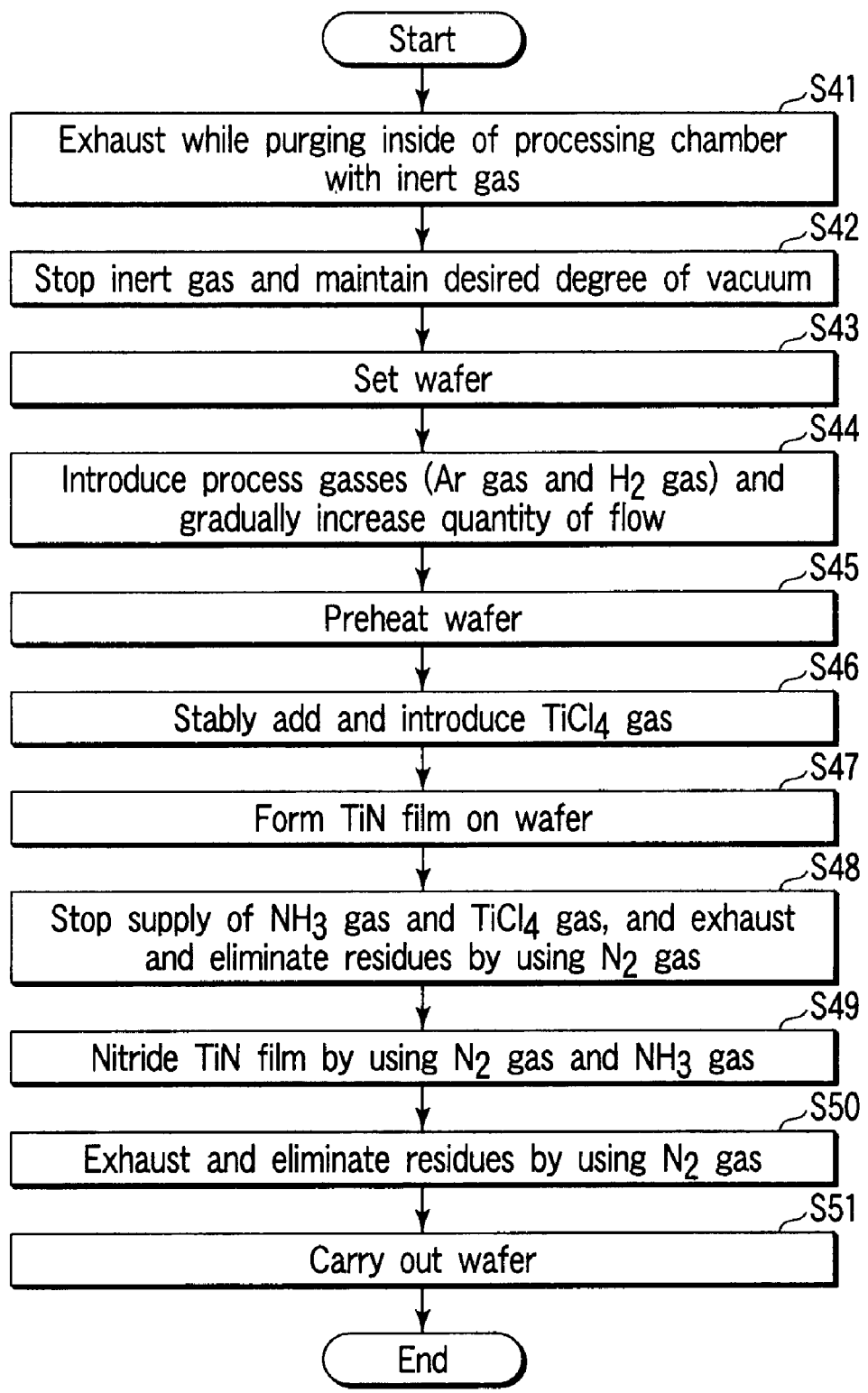
FIG. 28 is a flowchart for illustrating the continuous film-forming method of a titanium film/titanium nitride film as a second example.

A film-forming method of a titanium nitride film will now be described with reference to a flowchart of FIG. 28.

The inside of the processing chamber is first purged with an inert gas while performing exhaust (step S41). Then, introduction of the inert gas is stopped. When the inside of the processing chamber reaches a desired degree of vacuum, this state is maintained (step S42). A wafer is mounted on a mounting table in the processing chamber through a non-illustrated vacuum load lock mechanism while maintaining the vacuum state (step S43).

Further, a process gas other than $TiCl_4$ gas (for example, an $N_2$ gas and an $NH_3$ gas) is introduced into the processing chamber, the flow rate of which is gradually increased (step S44). This is carried out because a warpage may be probably generated to the wafer when the process gas is introduced into the processing chamber so as to rapidly increase a quantity of flow of this gas.

Thereafter, the wafer is preheated while introducing the process gas ($N_2$ and $NH_3$ gasses) into the processing chamber (wafer is previously heated to the same temperature as that of the film-forming process before the process) (step S45).

Then, after the $TiCl_4$ gas is not introduced into the chamber but temporarily caused to flow to an evac line provided as a bypass from the gas supply system for a predetermined time and a quantity of flow thereof is stabilized while introducing the process gas ($N_2$ and $NH_3$ gasses), a non-illustrated preflow valve is operated and that gas is introduced into the processing chamber (step S46). This is carried out in order to correctly stabilize a quantity of flow of the $TiCl_4$ gas, introduce this gas into the processing chamber and form a correct film thickness. In regard to perfect formation of a thin film, since the film thickness varies due to fluctuations in a quantity of flow of the material gas, this processing is important.

A TiN film is formed on the wafer in this gas atmosphere (step S47). Then, when the TiN film is formed to a desired thickness, supply of the $NH_3$ and $TiCl_4$ gasses is stopped, and residues (film-forming components) in the chamber are purged and exhausted while introducing the $N_2$ gas into the chamber (step S48).

Then, the $NH_3$ gas is further introduced while leading the $N_2$ gas into the processing chamber, and the TiN film is further nitrided (step S49). This is carried out in order to subject a chlorine component in the formed TiN film to reduction nitriding and removal. Furthermore, introduction of the $NH_3$ gas is stopped, and residues in the processing chamber are exhausted and removed while maintaining introduction of the $N_2$ gas into the processing chamber (step S50). Then, the wafer is carried to the outside from the inside of the processing chamber (step S51).

Incidentally, as to process conditions of the film-forming process of the TiN film at the step S47, a quantity of flow of the $TiCl_4$ gas is 10 to 100 sccm, a quantity of flow of the $NH_3$ gas is 20 to 2000 sccm, a quantity of flow of the $N_2$ gas is 500 to 12220 sccm or, preferably, a quantity of flow of the $TiCl_4$ gas is 25 to 60 sccm, a quantity of flow of the $NH_3$ gas is 100 to 1000 sccm, and a quantity of flow of the $N_2$ gas is 500 to 6000 sccm. A gas flow quantity ratio of the $TiCl_4$ gas to a total gas flow quantity is 0.000087 to 0.16 or preferably 0.0036 to 0.09, and a flow quantity ratio of the $TiCl_4$ gas to the $NH_3$ gas is 0.005 to 5 or preferably 0.025 to 0.6. Moreover, as to process conditions of the nitriding process at the step S49, a gas flow quantity ratio of the $NH_3$ gas to the total gas flow quantity is 0.0016 to 0.8 or 0.016 to 0.66. A TiN film with the good quality can be formed by the film-forming process with the above-described ratios.

A concrete example using such a plasma film-forming system as shown in FIG. 25 will now be described.

In this plasma film-forming system, a resistance heater (not shown) is embedded in the mounting table provided in the processing chamber 201. The wafer 203 is heated to a predetermined temperature, e.g., approximately 400° C. by this resistance heater and, for example, an Ar gas as a film-forming process gas and a gas including an $H_2$ gas, an SiH gas and a Ti gas as a reduction gas are introduced from the shower head portion 204 into the processing chamber 201 in predetermined quantities. Also, a high-frequency voltage of 450 kHz to 60 MHz is applied to the shower head portion 204, and the plasma is generated, thereby forming a titanium film. For example, as gasses including titanium, there are $TiCl_4$, $TiI_4$, $TiBr_4$, organic Ti, Ti $(C_2H_5)_3$ gasses.

Figure 26A:
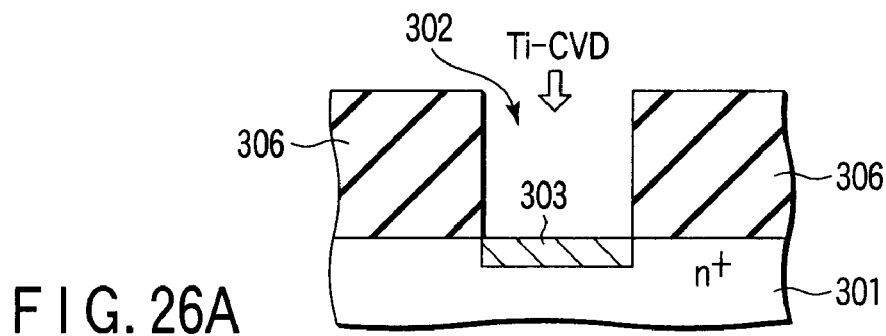
FIGS. 26A to 26D are process charts for illustrating a film-forming process.

A process pressure at this moment is 0.5 to 10 Torr or, preferably, 1 to 5 Torr. Under this condition, as shown in FIG. 26A, a titanium film 303 is selectively deposited on a conductor (substrate) 301 exposed at the bottom of a contact hole 302 opened to the insulating layer 306. In this case, $TiSi_2$ is formed in the self-matching manner from the reaction with Si in the substrate simultaneously with film formation of Ti. A thickness of this titanium film 303 is, e.g., 5 to 50 nm and, preferably, 10 to 30 nm.

In this manner, upon completion of the titanium film-forming process, the substrate 301 is subjected to a titanium nitriding process at the same mounting position. At first, after stopping supply of the process gas for titanium film formation, the process gas atmosphere in the processing chamber 201 is exhausted during supply of Ar and $H_2$ gasses. Then, as the plasma nitriding gas, a gas obtained by mixing the Ar gas, the $H_2$ gas and at least one of the $N_2$, $NH_3$ and MMH (mono methyl hydrazine) gasses or the respective gasses are individually supplied from the shower head portion 204 into the processing chamber 201 and mixed in the chamber. The nitrided gas atmosphere is formed in the processing chamber 201 by introducing the nitriding gas. Then, a high-frequency voltage of 450 kHz to 60 MHz is applied from a high-frequency power supply 205 to the shower head portion 204 which becomes an upper electrode through a matching box 206, and the nitriding plasma is generated in the chamber.

Figure 26B:
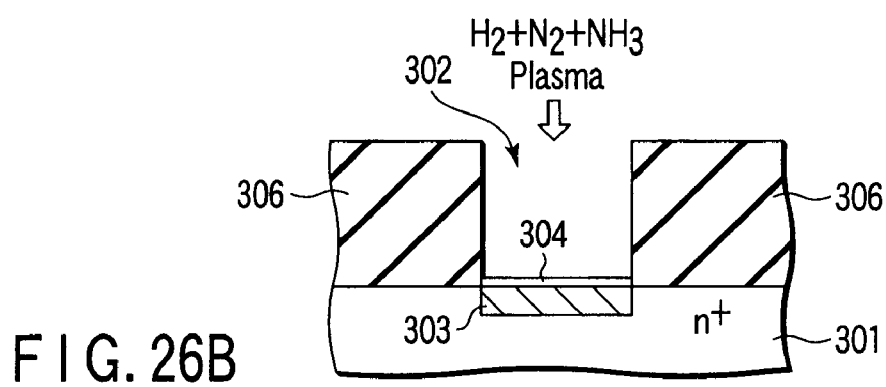

As a result, the surface of the titanium film 303 is subjected to the nitriding process, and a nitrided film 304 is formed as shown in FIG. 26B. Moreover, nitriding is possible by supplying the mixed gas of $H_2+N_2$ or $N_2+NM_3$ or $H_2+NH_3$. More preferably, the mixed gas consists of $Ar+H_2+NH_3$. In this case, all of the titanium film may be nitrided.

As nitriding process conditions at this moment, quantities of the respective gases to be supplied are as follows. $H_2$: approximately 250 to 3000 sccm, $N_2$: approximately 50 to 1000 sccm, $NH_3$: approximately 50 to 1000 sccm, and MMH: approximately 1 to 100 sccm. The process pressure is approximately 0.5 to 10 Torr or preferably 1 to 5 Torr, and the process temperature is approximately 350 to 700° C. Moreover, the high-frequency power is 100 to 2000 W, and preferably 500 to 1000 W. It is to be noted that appropriately selecting each of quantities of flow of the $H_2$ gas, the $N_2$ gas, the $NH_3$ gas and the MMH gas can suffice and these quantities of flow are not restricted to those mentioned above.

This nitriding process improves the adhesion of the Ti film and the TiN film. That is, an unreacted product such as $TiCl_4$ in the Ti film or on the surface of the Ti film is reduced and Ti is nitrided. In addition, since $TiCl_4$, which is the film-forming gas, etches the Ti film when forming the TiN film after formation of the Ti film, this process can suppress such etching.

Figure 26C:
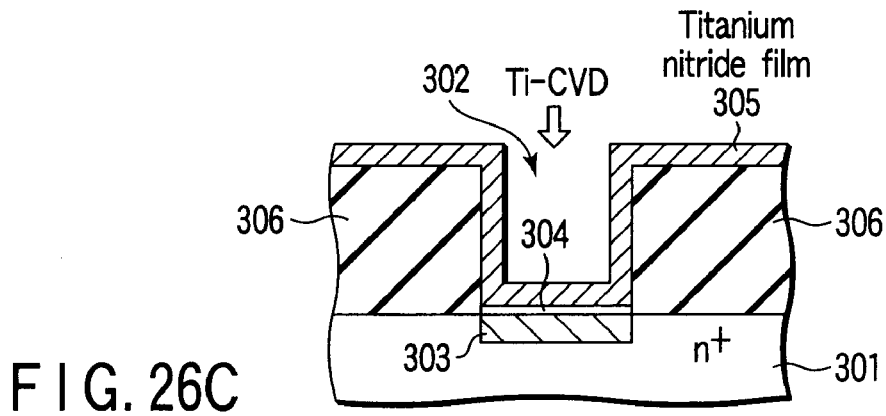

Upon completion of the titanium nitriding process in this manner, the substrate 301 is moved into another film-forming system which is maintained in a vacuum state in advance, and there is carried out a film-forming process in the film-forming system to form such a titanium nitride film as sown in FIG. 26C by using the known processing method. A titanium nitride film 305 which functions as a barrier metal layer is formed by CVD on the inner wall surface of the contact hole 302 and the entire upper surface of the insulating layer 306.

As the process gas in this process, for example, $TiCl_4$, $NH_3$ and $N_2$ can be used. Additionally, the process temperature is approximately 400 to 600° C., and the process pressure is approximately 0.1 to 10 Torr or preferably 0.5 to 5 Torr. Further, a TiN film can be formed by alternately passing the $TiCl_4$ gas and the $NH_3$ gas. Based on this, the density of chlorine impurities can be reduced, and a film with the high-barrier property can be formed.

Figure 26D:
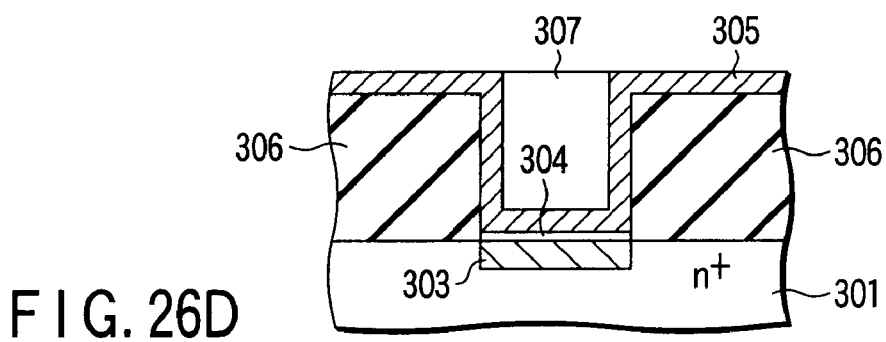

When this titanium nitride film-forming process is terminated, the processed substrate 301 is carried out from the film-forming system, and thereafter a conductive material 307 such as tungsten, aluminium or copper is embedded in the contact hole as shown in FIG. 26D.

When subjecting the surface of the titanium film to the nitriding process in this manner, the plasma is generated in the atmosphere of a mixed gas consisting of the Ar gas, the $H_2$ gas and at least one of the $N_2$ gas, the $NH_3$ gas and the MMH (mono methyl hydrazine) gas, and the surface of the Ti film is nitrided. Therefore, the adhesion with the TiN film is improved, and peeling from the substrate can be suppressed. In the conventional method using only the $N_2$ gas or only the $NH_3$ gas, a large quantity of nitrogen radicals with a high nitriding capability is generated and the TiClx by-product material on the surface of the Ti film or in the Ti film is not reduced. Therefore, nitriding Ti is suppressed, the adhesion is lowered, and peeling occurs.

However, as a result of performing the plasma process by using the mixed gas consisting of the Ar gas, the $H_2$ gas and at least one of the $N_2$ gas, the $NH_3$ gas and the MMH (mono methyl hydrazine) gas, active hydrogen atoms reduce the TiClx by-product material on the surface of the Ti film or in the Ti film and remove Cl, and the active Ti and the active N radical react with each other, thereby efficiently nitriding the surface of the Ti film. Accordingly, the adhesion with the TiN film is improved. For verification, the present applicant actually performed the titanium film-forming process and the nitriding process, formed the TiN film which is the barrier metal, and carried out a scratch test. However, peeling of the film from the substrate was not confirmed.

Moreover, when the plasma nitriding process is performed by using the mixed gas consisting of the Ar gas, the $H_2$ gas and at least one of the $N_2$ gas, the $NH_3$ gas and the MMH gas in this manner, there can be obtained a result that the contact resistance can be greatly reduced. That is because gasses such as $Cl_2$ or HCl are removed to the outside of the system by removal of Cl by strong reduction of the $TiCl_4$ material remaining in the titanium film by the $H_2$ gas and degasification from the by-product, and hence chlorine (Cl) which can be factor of an increase in resistance does not remain in the film or on the surface of the film.

Since the nitriding process of the titanium film surface is carried out by the plasma process in the atmosphere of the mixed gas consisting of the Ar gas, the $H_2$ gas and at least one of the $N_2$ gas, the $NH_3$ gas and the MMH gas, the contact resistance can be greatly reduced, and a stable nitride can be formed from the by-product in the chamber which is generated in formation of the titanium film. Therefore, peeling of this nitride can prevent the particles from being produced.

Here, description will now be given as to a result obtained by performing evaluation of a change in degree (%) of the chip number depending on presence/absence of each gas or when changing a quantity follow.

Figure 38A:
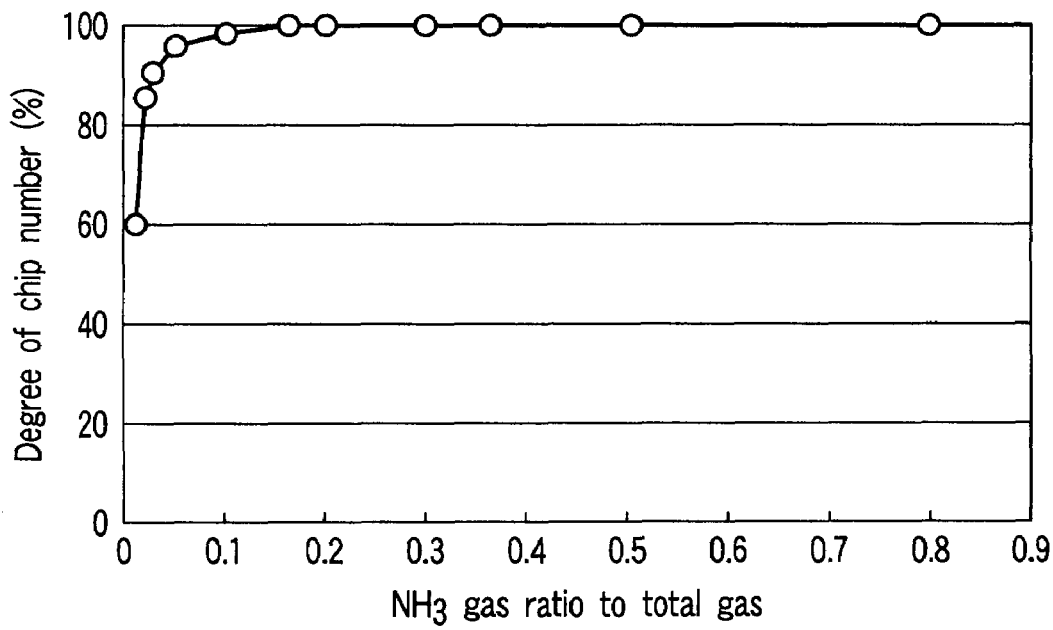
FIG. 38A is a view showing the relationship between an $NH_3$ gas ratio with respect to all gases and a degree of the chip number.
Figure 38B:
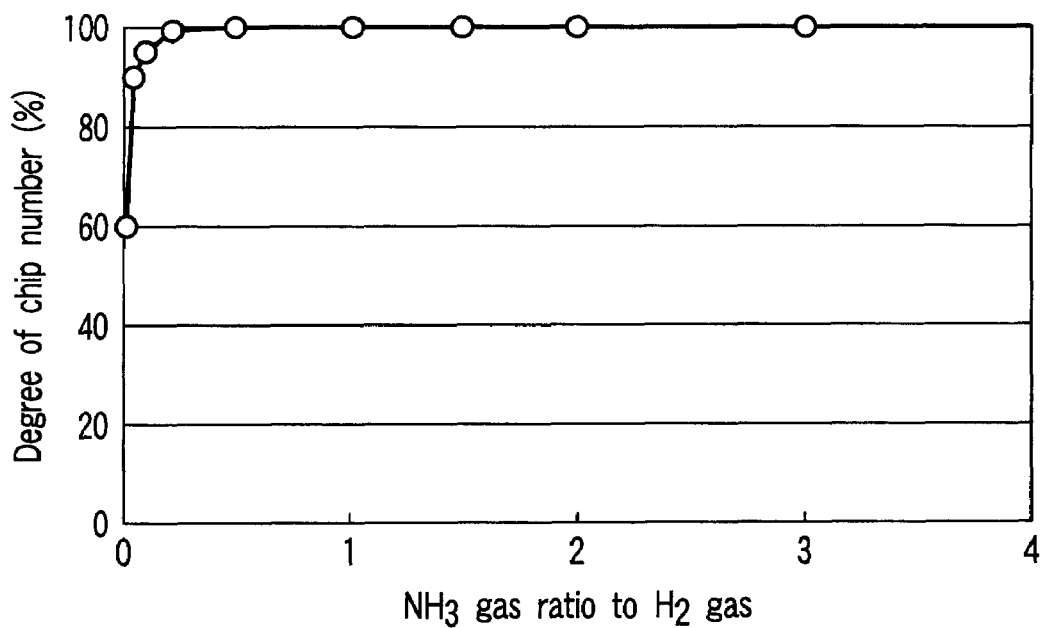
FIG. 38B is a view showing the relationship between an $NH_3$ gas ratio with respect to an $H_2$ gas and a degree of the chip number.

FIGS. 29A to 29D are views showing degrees (%) of the chip number depending on presence/absence of each gas or when changing a flow quantity. Here, the degree of the chip number is shown as a resistance value, but this is a ratio of the chips in a range of arbitrary resistance values. In addition, FIG. 38A shows the relationship between an $NH_3$ gas ratio relative to the entire gas and the degree of the chip number, and FIG. 38B is a view showing the relationship between an $NH_3$ gas ratio relative to the $H_2$ gas and the degree of the chip number.

FIG. 29A shows the degree of the chip number when the $H_2$ gas and the $N_2$ gas are used without the $NH_3$ gas and a quantity of flow of the $H_2$ gas is changed. FIG. 29B shows the degree of the chip number when the $N_2$ gas and the $NH_3$ gas are used without using the $N_2$ gas and a quantity of flow of the $NH_3$ gas is changed, and FIGS. 27C and 29D show the degrees of the chip number when all of the $N_2$ gas, the $H_2$ gas and the $NH_3$ gas are used and a quantity of flow of the $NH_3$ gas is changed. Further, a quantity of the $N_2$ gas is 50 sccm in FIG. 27C, and a quantity of the $N_2$ gas is 500 sccm in FIG. 29D. Besides, the Ar gas is used as the plasma gas.

In the example shown in FIG. 29A, the degree of the chip number is increased as a quantity of flow of the $H_2$ gas is increased. However, a quantity of the $H_2$ gas must be increased to approximately 2000 sccm and caused to flow. Furthermore, in the example shown in FIG. 29B, although the degree of the chip number is increased as a quantity of flow of the $NH_3$ gas is increased, the extent of increase is low. When a quantity of the $NH_3$ gas is approximately 400 sccm, the degree of the chip number is approximately 90% and does not reach 100%. On the other hand, in the example shown in FIG. 29C, a quantity of flow of the $N_2$ gas is 50 sccm, and the degree of the chip number is increased as a quantity of flow of the $NH_3$ gas is increased. The extent of increase is high, and the degree of the chip number reaches approximately 100% when a quantity of flow of the $NH_3$ gas is approximately 400 sccm. Furthermore, in the example shown in FIG. 29D, a quantity of flow of the $N_2$ gas is set to 500 sccm which is a large number, and the degree of the chip number stably maintains approximately 100% when a quantity of flow of the $NH_3$ gas is not less than 50 sccm.

According to the cleaning method of the film-forming system of the third embodiment mentioned above, the number of particles actually flowing through the exhaust system is measured. The number of particles is reduced after the peak, and a time when the number becomes lower than a predetermined quantity is judged as a just etch timing. Based on this judgment, setting of the end pint to terminate the cleaning process can be appropriately set. Therefore, excessive over-etching in the cleaning process can be avoided without being affected by the number of accumulated objects subjected to the process before the cleaning process. Therefore, not only reduction in duration of the life of the structure in the chamber can be prevented but also wasteful consumption of the cleaning gas can be suppressed.

Here, description will now be given as to a structure of a delivery mechanism for an object (for example, a wafer or a glass substrate) on the mounting table adopted in this embodiment.

Known delivering mechanism, such as shown in FIG. 1, have a structure that a plurality of push-up pins used to support the wafer respectively move up and down through pin insertion holes of the mounting table. In this structure, when the push-up pins move up and down and pass through the pin insertion holes in order to deliver the wafer, they may slide while coming into contact with the inner wall of the pin insertion holes and generate particles if the sliding accuracy is deteriorated or thermal deformation occurs. The generated particles enter the gas atmosphere in the vicinity of the wafer and adhere to the surface of the wafer when forming a film, which leads to a defect in a circuit pattern. Moreover, they adhere on the back side of the wafer, which can be a factor of bringing the particles into another chamber when carrying the wafer. In addition, the end of the push-up pin may collide with the opening portion of the pin insertion hole and the push-up pin may be damaged in some cases.

In addition, when the wafer is moved up, the mounting position of the wafer on the mounting table may be shifted or the wafer may fall from the above of the push-up pin due to vibrations caused by sliding of the push-up pin or existence of a gas in a space between the back side of the wafer and the mounting surface of the mounting table (however, it depends on the degree of vacuum in the processing chamber).

Thus, in the delivering mechanism adopted in this embodiment, the respective push-up pins are inserted into a plurality of pin insertion holes of the mounting table. This push-up pin is formed to have a length which can be accommodated in a range of a depth of the pin insertion hole. A push-up member which pushes up the respective push-up pins from the lower side (direction along the pin insertion holes) is connected. The push-up pins smoothly move up and down from the upper surface of the mounting table (wafer mounting surface) by moving up and down the push-up member (positioning drive pin) with a predetermined stroke.

Figure 30A:
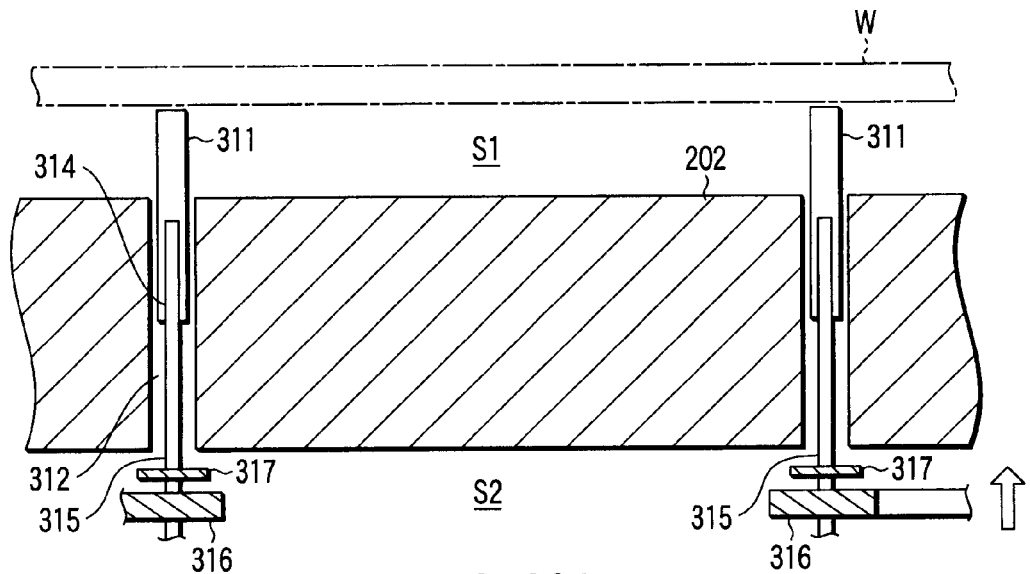
FIGS. 30A and 30B are views for illustrating a structure of an object delivering mechanism in a mounting table adopted inn a third embodiment.
Figure 30B:
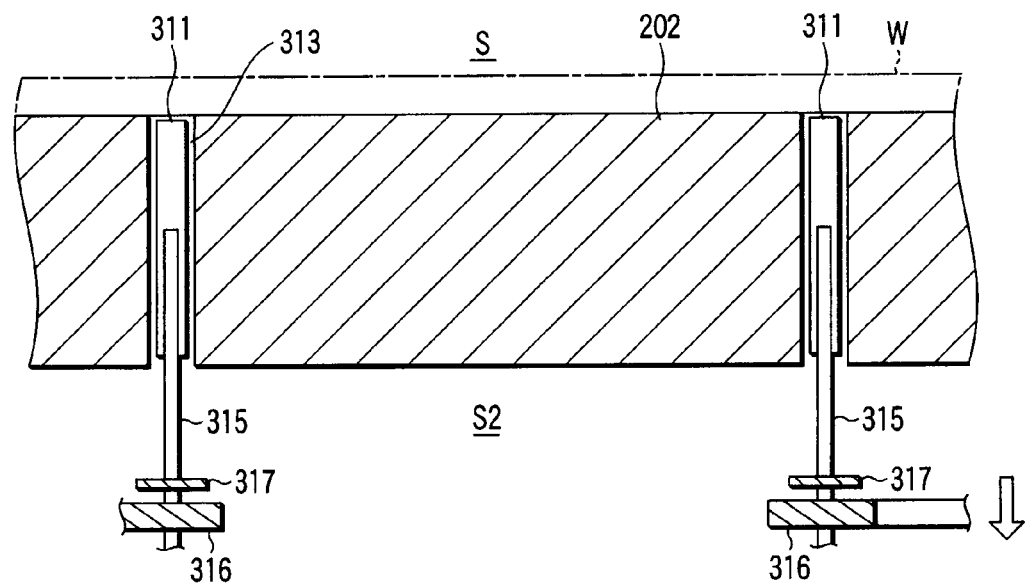

Concretely, as shown in FIGS. 30A and 30B, the entire body of the push-up pin 311 is formed of ceramics or quartz, and the push-up pins 311 are respectively fitted into a plurality of pin rod insertion holes 312 provided to the mounting table 202. In this case, the outside diameter of the push-up pin 311 is similarly smaller than the inside diameter of the pin rod insertion hole and a small gap 313 is formed therebetween. This pin rod insertion hole 312 communicates with a space S1 between the back side of the wafer W and the upper surface of the mounting table 96 and a space S2 on the back side (lower side) of the mounting table 202 through the gap 313.

This push-up pin 311 has a flat upper end surface, and a fitting hole 314 is formed to the lower end of this pin so as not to allow insertion. The upper end part of the positioning drive pin 315 is inserted and fixed in this fitting hole 314. The lower end of the positioning drive pin 315 pierces and is fixed to the push-up member 316. This push-up member 316 is connected to a later-described actuator 317 shown in FIG. 25 and driven upward and downward. A stopper 317 to restrict upward movement is provided to the lower side of the positioning drive pin 315. A lifting position of a catch-up pin may be defined by bringing it into contact with the stopper and stopping it when lifting up.

With such a structure, as shown in FIG. 30A, the positioning drive pin 315 and the push-up pin 311 move up by lifting drive of the push-up member 316, and the wafer W is delivered to a non-illustrated carrying arm. On the contrary, as shown in FIG. 30B, the positioning drive pin 315 and the upper surface of the push-up pin 311 move down so as to be parallel with or lower than the upper surface of the pin rod insertion hole 312 of the mounting table 202 by downward drive of the push-up member 316, and the supported wafer W is mounted on the upper surface of the mounting table 202. The wafer W is held by a non-illustrated electrostatic chuck mechanism provided to the mounting table 202.

Now, FIG. 25 shows a structural example of the processing system having mounted therein the push-up pin having such a structure and their drive mechanism.

The processing chamber 201 is connected to a non-illustrated load lock chamber through a gate valve, and can maintain the vacuum state by exhausting the inside of the both chambers. The wafer is carried between these chambers by a non-illustrated carrying arm. Further, a non-illustrated resistance heater is embedded in the mounting table 202 having the wafer W mounted thereon, and the wafer can be heated to a desired temperature and stably maintained.

The insides of the load lock chamber and the processing chamber 201 are first maintained at the high degree of vacuum. The wafer W to be processed is held by the carrying arm and carried to a predetermined position in the processing chamber 201 through the opened gate valve and a carry-in entrance. At this moment, when the actuator 317 is driven and the push-up member 316 is moved up as shown in FIG. 30A, the positioning drive pin 315 moves up to a delivering position (uppermost position) from a standby position (lowermost position). The upward movement of the positioning drive pin 315 pushes up the push-up pin 311 so as to be pushed up from the pin insertion hole 312. The upper end of the push-up pin 311 pushes up the wafer W held by the carrying arm, and the wafer W is consequently delivered from the carrying arm to the push-up pin 311. Thereafter, the carrying arm is retired.

Then, when the actuator 316 is driven and the push-up member 316 is moved down as shown in FIG. 30B, the positioning drive pin 315 and the push-up pin 311 move down, and the push-up pin 311 is completely immersed in the pin insertion hole 312. At this moment, the wafer W is also moved down and mounted on the upper surface (mounting surface) of the mounting table 202 and held by a non-illustrated electrostatic chuck mechanism. Thereafter, various processes, such as film-forming processes of Ti and TiN films or a nitriding process are applied to the wafer W.

Furthermore, upon completion of the processes, the push-up member 316 is again moved up. The positioning drive pin 315 is pushed up by this upward movement, and the push-up pin 311 having the wafer W mounted thereon is moved up. The carrying arm is inserted under the lifted wafer W, and the wafer W is delivered to the carrying arm by downward movement of the push-up pin 311. The wafer W is carried to the outside simultaneously with evacuation of the carrying arm.

With this structure, since the push-up pin 311 inserted into the pin insertion hole 312 smoothly moves up and down with a small contact when delivering, it is possible to avoid the contact which generates particles or collision or sliding which may damage the push-up pin.

Moreover, since the space S1 between the back side of the wafer W and the mounting surface of the mounting table 202 communicates with the space S2 on the back side (lower side) of the mounting table 202 through the gap 313, it is possible to let the gas existing in the space S1 out to the space S2 when moving down the wafer or prevent shifting of the mounting position or falling of the wafer which occurs when the space S1 is formed in the state that the back side of the wafer W is appressed against the mounting surface in the case of moving up the wafer W.

Figure 31:
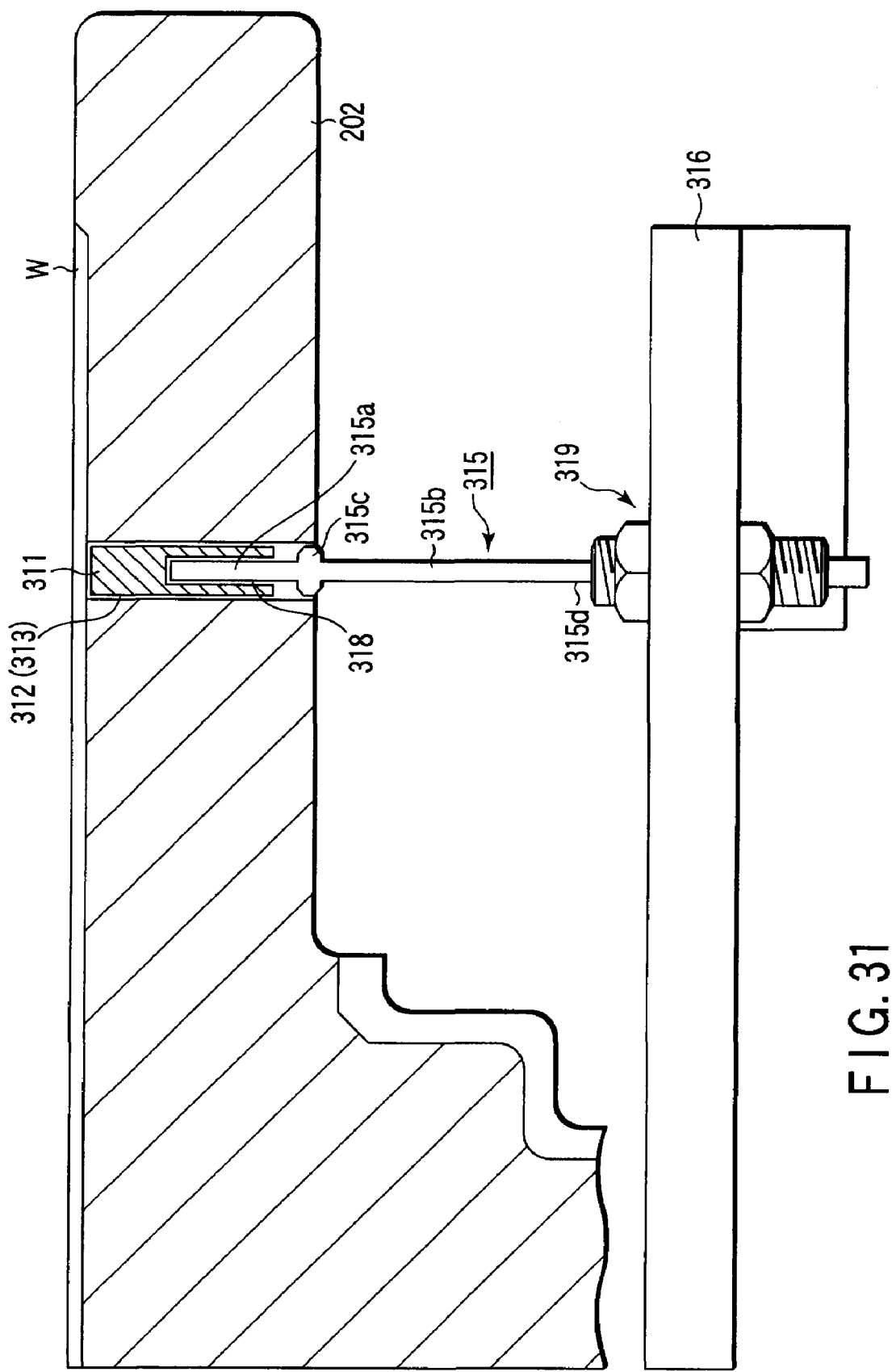
FIG. 31 is a view showing a cross-sectional structure of a first modification of the delivering mechanism.

FIG. 31 shows a cross-sectional structure of a first modification of the delivering mechanism. Although the push-up pin 311 is supported by the upper end part of the positioning drive pin 315 in the delivering mechanism mentioned above, a flange portion 315c is provided in the middle of the positioning drive pin 315 and the push-up pin 311 is supported by the flange portion 315c of the positioning drive pin 315 in this modification. Other structures are equivalent to that of the delivering mechanism mentioned above.

This positioning drive pin 315 has the outside diameter of the upper part 315a which is fitted to the fitting hole 318 of the push-up pin 311 being slightly smaller than the inside diameter of the fitting hole 318, and has a gap between itself and the push-up pin 311. Moreover, the outside diameter of the flange portion 315c of the positioning drive pin 315 is slightly smaller than the inside diameter of the pin insertion hole 312, and there is a gap 313 between the flange portion 315c and the inner wall of the pin insertion hole 312. In addition, the outside diameter of the lower part 315b of the positioning drive pin 315 is smaller than the inside diameter of the pin insertion hole 312, and there is a gap between the lower part 315b and the inner wall of the pin insertion hole 312.

With this structure, in addition to the effects and advantages of the delivering mechanism mentioned above, since the push-up pin 311 is substantially vertically held in the fitting hole 318, the push-up pin 311 can be prevented from being inclined when moving, and the push-up pin 311 can be smoothly moved up and down with less contact.

Additionally, a reference position (lowering position) and a delivering position (lifting position) of the push-up pin 311 can be readily adjusted by adjusting fixing positions of the positioning drive pin 315 and the push-up member 316.

In this modification, the lower end part 315d of the positioning drive pin 315 is fixed to the push-up member 316 by a nut 320 and the like. However, when there is no high requirement in the positioning accuracy, the lower end part 315d and the push-up member 316 may be slidably attached in a given range. With such a structure, even if the push-up member 316 expands and contracts due to heat, the influence of the upward and downward fluctuations of the push-up pin 311 can be reduced. It is to be noted that the gap 313 is likewise provided between the push-up pin 311 and the pin insertion hole 312 in the second modification and hence the gas passes through the gap 313 during the upward movement and shifting of the position of the wafer W on the mounting surface or falling from the push-up pin 311 and the like can be prevented.

Figure 32:
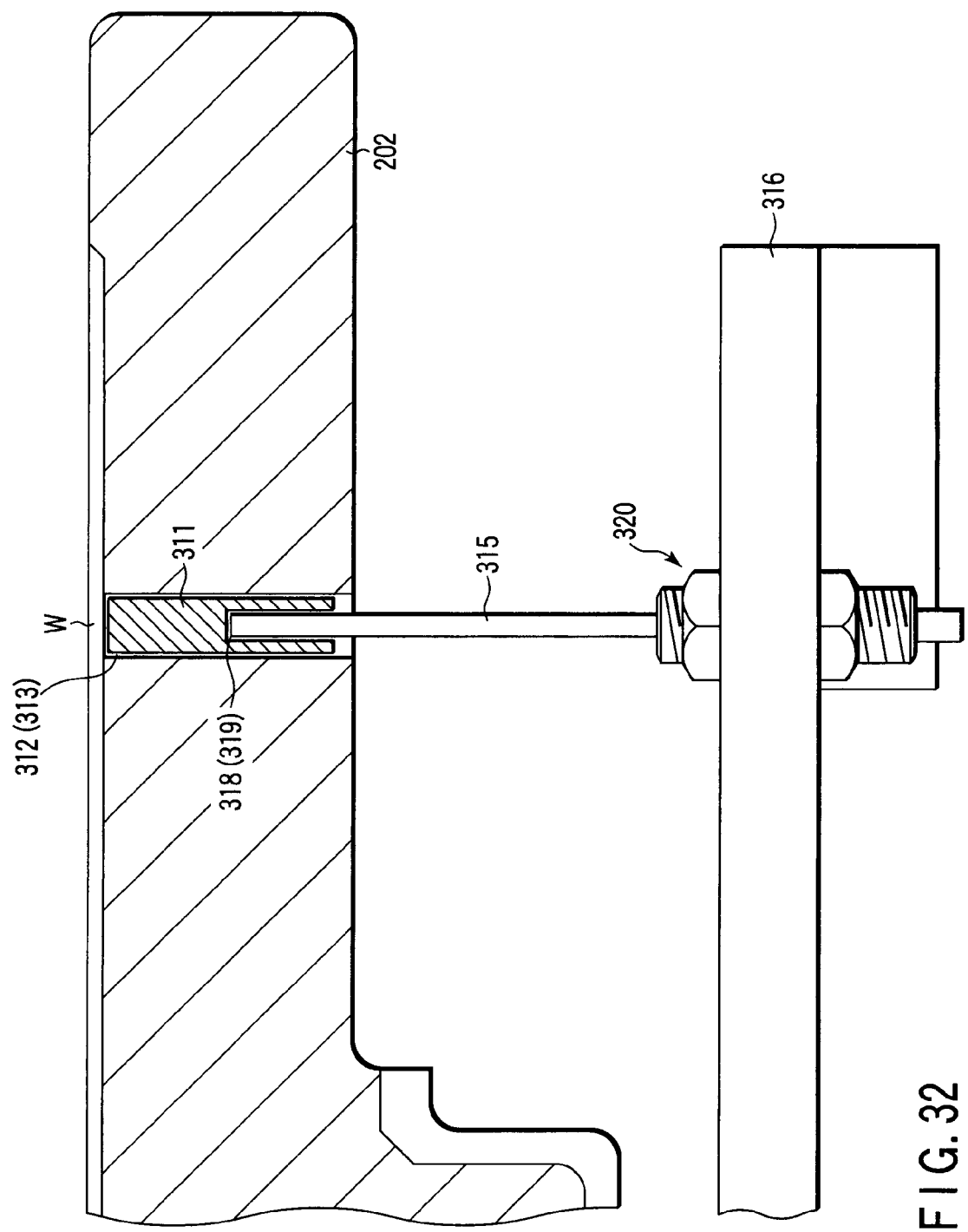
FIG. 32 is a view showing a cross-sectional structure of a second modification of the delivering mechanism.

FIG. 32 shows a cross-sectional structure of a second modification of the delivering mechanism mentioned above. In this second modification, a gap 319 is provided between the wall surface of the fitting hole 318 and the upper part side surface of the positioning drive pin which is fitted in this fitting hole 318, and there is provided a free state that only the upper end part is in contact. It is to be noted that a plurality of the push-up pins 311 are provided to the mounting table 202. Clearances in the gaps 313 between these push-up pins 311 and the respective pin insertion holes 312 are equivalent to each other, and these push-up pins 311 move down all at once at the same speed even in the free state. Further, the lower end part of the positioning drive pin 315 is fixed to the push-up member 316 by a nut 320 and the like.

With such a structure, the effects and advantages similar to those of the above-described delivering mechanism can be obtained, and since the gap 319 is provided between the push-up pin 311 and the positioning drive pin 315, heat generated in the mounting table 202 is hardly transferred to the positioning drive pin 315, thereby preventing thermal deformation and the like of the positioning drive pin 315.

Figure 33:
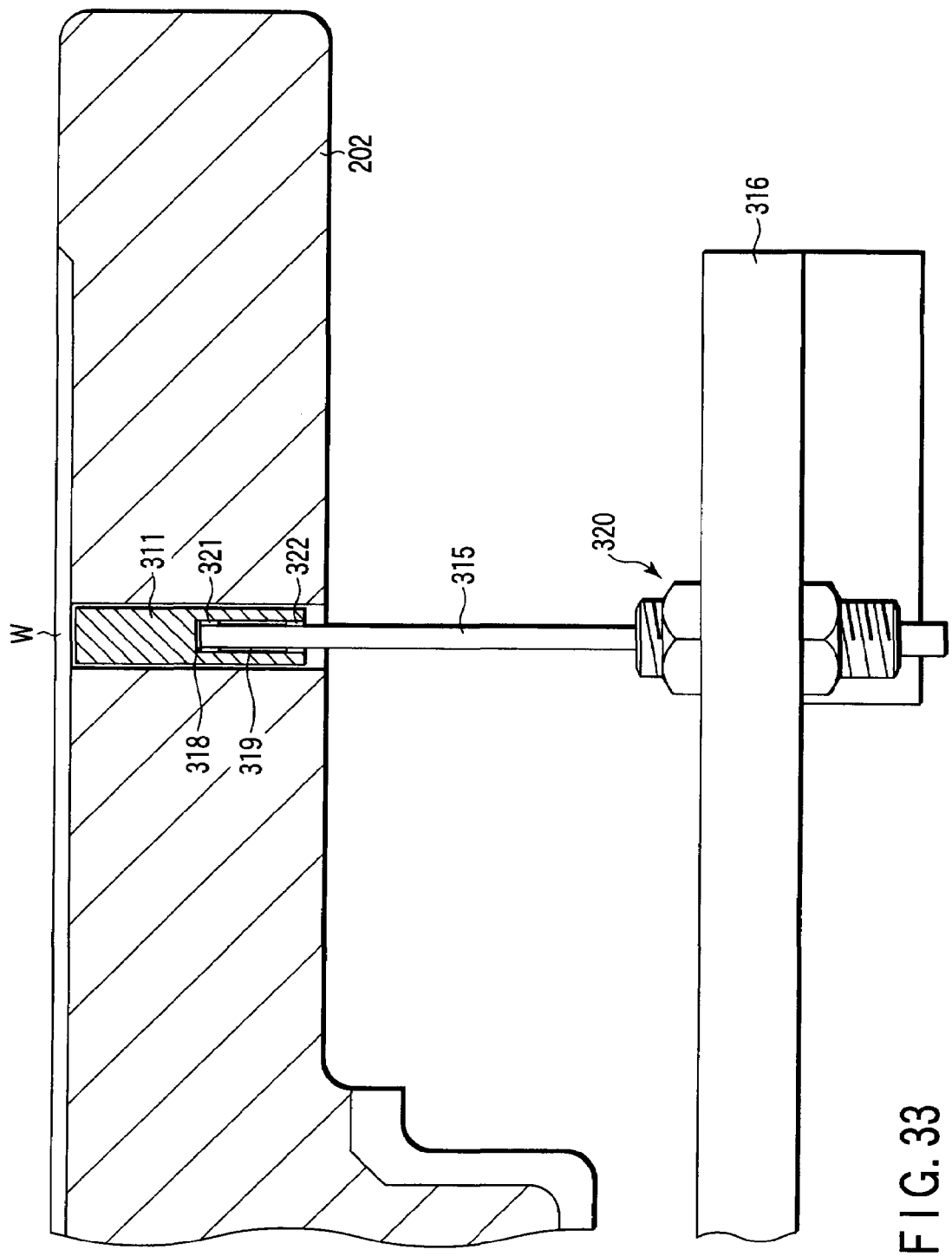
FIG. 33 is a view showing a cross-sectional structure of a third modification of the delivering mechanism.

FIG. 33 shows a cross-sectional structure of a third modification of the above-described delivering mechanism.

In this third modification, a plurality of push-up pins 311 with a short length are formed so as not to pierce the pin insertion holes 312 formed to the mounting table 202. There is provided a structure to assuredly move down the push-up pins 311 by a stopper-like function when moving down these push-up pins 311.

As shown in FIG. 33, an evagination portion 321 which protrudes in the form of a flange is formed at the upper end part of the positioning drive pin 315. Furthermore, a constriction portion 322 is formed at a lowermost part of the fitting hole 318 of the push-up pin 311. The maximum outside diameter dimension of the evagination portion 321 is formed so as to be larger than the minimum inside diameter dimension of the constriction portion 322, namely, it is good enough that the evagination portion 321 is caught by the constriction portion 322 and does protrude from the fitting hole 318. The evagination portion 321 and the constriction portion 322 are a male screw and a female screw, respectively, and the upper end part of the positioning drive pin 315 is inserted into the fitting hole 318 by screwing the evagination portion 321.

It is to be noted that the evagination portion 321 and the constriction portion 322 may be engaged by not only the screw shapes but also by forming, e.g., a key way to the constriction portion 322, forming a key protrusion portion (fitting to the key way) which partly protrudes to the evagination portion 321, fitting and rotating this key protrusion portion. However, the key way must have a double-lamination structure or a stopper must be provided inside of the key way in order to prevent the key protrusion portion from easily bursting through. Moreover, the lower end part of the positioning drive pin 315 is fixed to the push-up member 316 by a nut 320 and the like.

With such a structure, when moving down the positioning drive pin 315 and returning the push-up pin 311 into the mounting table 202, providing the constriction portion (or the key way) 322 to the push-up pin 311 enables engagement with the evagination portion (or the key protrusion portion) 321 and forcible downward movement. Further, since the gap 319 is provided between the push-up pin 311 and the positioning drive pin 315, heat generated on the mounting table is hardly transferred to the positioning drive pin 315, thereby avoiding thermal deformation and the like of the positioning drive pin 315.

Furthermore, play of the upper end part of the positioning drive pin 315 relative to the fitting hole 318 is eliminated by providing the constriction portion 322 at a position above the bottom of the fitting hole 52 by a length of the evagination portion 321, and the push-up pins 311 can be uniformly moved down.

FIG. 34 shows a cross-sectional structure of a fourth modification of the delivering mechanism mentioned above. This modification is a structure obtained by adding a stopper function of the push-up pins 311 to the structure of FIG. 32. That is, a flange portion 323 is provided at an opening part of the pin rod insertion hole 312 of the mounting table 202 and caused to function as a stopper when the push-up pin 311 is moved down (accommodated in the pin rod insertion hole 312). The lower end part of the push-up pin 311 comes into contact with the flange portion 323. At this moment, the upper surface of the upper end part of the push-up pin 311 is configured to be on the same level as the mounting surface of the mounting table 202 or stopped at a position lower than the mounting surface.

With such a structure, since the push-up pin 311 can be engaged with and supported by the flange portion 323 when accommodated in the mounting table 202, the push-up pin 311 can be always stopped at an appropriate position. Further, since the gap 319 is provided between the push-up pin 311 and the positioning drive pin 315, heat generated on the mounting table 202 is hardly transferred to the positioning drive pin 315, thereby avoiding thermal deformation and the like of the positioning drive pin 315.

FIG. 35 shows a cross-sectional structure of a fifth modification of the delivering mechanism mentioned above. This modification has a configuration that the structures of the evagination portion and the constriction portion in FIG. 33 are combined with the structure of the flange portion in FIG. 34 and the positioning drive pin 315 is separated from the push-up member 316. A pin support plate 324 is provided at a position of the push-up member 316 where it comes into contact with the lower end part of the positioning drive pin 315.

In this structure, when the push-up member 316 is moved up by a non-illustrated actuator and the like, it comes into contact with the lower end part of the positioning drive pin 315 and pushes up the positioning drive pin 315. Then, the upper end part of the positioning drive pin 315 moves up, the push-up member 316 comes into contact with the uppermost part (bottom) of the fitting hole 318, and the push-up pin 311 moves up so as to be thrusted out from the pin insertion hole 312. Then, when upward movement of the push-up member 316 is stopped, the push-up pin 311 is thereby stopped at the wafer delivery position.

Furthermore, when the push-up member 316 moves down, the positioning drive pin 315 and the push-up pin 311 integrally move down by their weights. Moreover, the push-up pin 11 comes into contact and engages with the flange portion, the positioning drive pin 315 moves down, and the evagination portion of the positioning drive pin 315 comes into contact and engages with the constriction portion. With the structure of the fifth embodiment, it is possible to obtain the effects and advantages including both the third and fourth modifications.

In the above-described delivering mechanism for an object to be processed, the push-up pin pierces the mounting table and does not move up and down, and the push-up pin having the length equal to or smaller than the thickness of the mounting table is inserted into the pin rod insertion hole of the mounting table. The push-up pin is supported so as to be cable of moving in the direction along the pin rod insertion hole, namely, the vertical direction, and the push-up pin smoothly moves up and down by the positioning drive pin. Therefore, generation of particles is suppressed, and damage to the push-up pin due to collision of the end of the push-up pin with the opening part of the pin insertion hole can be avoided. The space between the back side of the wafer and the mounting surface of the mounting table communicates with the space on the back side of the mounting table by the gap provided between the pin rod insertion hole and the push-up pin, and the gas can be smoothly moved when mounting and removing the wafer onto/from the mounting table, thereby preventing the displacement of the wafer or falling of the wafer. Furthermore, it is possible to avoid shifting of mounting of the wafer or falling of the wafer from the pin due to vibrations caused by sliding of the mounting table and the push-up pin.

The invention claimed is:

1. A processing apparatus for processing a substrate, comprising:
   a processing chamber into which the substrate is transferred;
   an exhaust pump which exhausts an atmosphere or gas from the processing chamber;
   an exhaust pipe connecting the processing chamber and the exhaust pump; and
   a particle measuring system, which is attached to the exhaust pipe and detects particles included in an exhaust gas flowing through the exhaust pipe,
   wherein the particle measuring system includes a laser beam irradiator, a scattered light detector and a beam stopper, and emits a laser beam from the laser beam irradiator to a part having a high density of particles included in the exhaust gas on an outer side away from a center of the exhaust pipe which is exhausted through the exhaust pipe, thereby detecting scattered light from the particles by the scattered light detector, and measuring the number of the particles included in the exhaust gas.

2. The processing apparatus according to claim 1, wherein the scattered light detector of the particle measuring system is provided to direct a detection direction to a part having a high density of the particles included in the exhaust gas exhausted in the exhaust pipe.

3. The processing apparatus according to claim 1, wherein the laser beam irradiator of the particle measuring system has a semiconductor laser.

4. The processing apparatus according to claim 1, wherein the particle measuring system is attached to a manifold.

5. The processing apparatus according to claim 1, wherein the particle measuring system is attached to an exhaust pipe of a vacuum exhaust system provided in a vacuum room comprised in any one of a film-forming system, etching system and annealing system.

6. The processing apparatus according to claim 1, wherein the laser beam irradiator of the particle measuring system is provided in a position away from a central axis of the processing chamber to direct a detection direction to the part having the high density of the particles included in the exhaust gas exhausted in the exhaust pipe.

7. The processing apparatus according to claim 1, wherein an attachment position on the exhaust pipe of the particle measuring system is determined as a position where the density of the particles included in the exhaust gas in the exhaust pipe is variable at a minimal distance to the processing chamber where light generated in the processing chamber does not reach.

8. A processing apparatus for processing a substrate, comprising:
a processing space in which the substrate is processed;
an exhaust pump which exhausts an atmosphere or gas from the processing space to generate an exhaustion atmosphere;
an exhaust flow path connecting the processing space and the exhaust pump; and
a particle measuring system, which is attached to the exhaust flow path and detects particles included in an exhaust gas flowing through the exhaust flow path,
wherein the particle measuring system includes a laser beam irradiator, a scattered light detector and a beam stopper, and emits a laser beam from the laser beam irradiator to a part having a high density of particles included in the exhaust gas on an outer side away from a center of the exhaust flow path which is exhausted through the exhaust flow path, thereby detecting scattered light from the particles by the scattered light detector, and measuring the number of the particles included in the exhaust gas.

9. The processing apparatus according to claim 8, wherein the scattered light detector of the particle measuring system is provided to direct a detection direction to a part having a high density of the particles included in the exhaust gas exhausted in the exhaust pipe.

10. The processing apparatus according to claim 8, wherein the laser beam irradiator of the particle measuring system has a semiconductor laser.

11. The processing apparatus according to claim 8, wherein the particle measuring system is attached to a manifold.

12. The processing apparatus according to claim 8, wherein the particle measuring system is attached to an exhaust pipe of a vacuum exhaust system provided in a vacuum room comprised in any one of a film-forming system, etching system and annealing system.

13. The processing apparatus according to claim 8, wherein the laser beam irradiator of the particle measuring system is provided in a position away from a central axis of the processing space to direct a detection direction to the part having the high density of the particles included in the exhaust gas exhausted in the exhaust pipe.

14. The processing apparatus according to claim 8, wherein an attachment position on the exhaust pipe of the particle measuring system is determined as a position where the density of the particles included in the exhaust gas in the exhaust pipe is variable at a minimal distance to the processing chamber where light generated in the processing space does not reach.

15. A processing apparatus for processing a substrate, comprising:
a processing chamber into which the substrate is transferred;
an exhaust pump which exhausts an atmosphere or gas from the processing chamber;
an exhaust pipe connecting the processing chamber and the exhaust pump; and
a particle measuring system, which is attached to the exhaust pipe and detects particles included in an exhaust gas flowing through the exhaust pipe,
wherein the particle measuring system includes a laser beam irradiator, a scattered light detector and a beam stopper,
the laser beam irradiator is provided so as to emit a laser beam into the exhaust pipe along a line segment connecting a center point in a lateral cross section of the exhaust pipe with a central axis running through a center of the processing chamber in the vertical direction, and
the scattered light detector is provided in a direction substantially orthogonal to an irradiation direction of the laser beam.

16. The processing apparatus according to claim 15, wherein the scattered light detector of the particle measuring system is provided to direct a detection direction to a part having a high density of the particles included in the exhaust gas exhausted in the exhaust pipe.

17. The processing apparatus according to claim 15, wherein the laser beam irradiator of the particle measuring system has a semiconductor laser.

18. The processing apparatus according to claim 15, wherein the particle measuring system is attached to a manifold.

19. The processing apparatus according to claim 15, wherein the particle measuring system is attached to an exhaust pipe of a vacuum exhaust system provided in a vacuum room comprised in any one of a film-forming system, etching system and annealing system.

20. The processing apparatus according to claim 15, wherein the laser beam irradiator of the particle measuring system is provided in a position away from a central axis of the processing chamber to direct a detection direction to the part having the high density of the particles included in the exhaust gas exhausted in the exhaust pipe.

21. The processing apparatus according to claim 15, wherein a center of the scattered light detector of the particle measuring system is set so as to face a point which is offset by a predetermined distance from the center point in the cross section of the exhaust pipe in a direction opposite to a direction along which the central axis running through the center of the processing chamber in the vertical direction is positioned.

22. The processing apparatus according to claim 21, wherein a maximum value of the predetermined distance to be offset is 0.75 times as much as a radius of the exhaust pipe.

23. The processing apparatus according to claim 15, wherein an attachment position on the exhaust pipe of the particle measuring system is determined as a position where the density of the particles included in the exhaust gas in the exhaust pipe is variable at a minimal distance to the processing chamber where light generated in the processing chamber does not reach.

24. A processing apparatus for processing a substrate, comprising:

a processing chamber into which the substrate is transferred;

an exhaust pump which exhausts an atmosphere or gas from the processing chamber, an exhaust pipe connecting the processing chamber and the exhaust pump; and a particle measuring system, which is attached to the exhaust pipe and detects particles included in an exhaust gas flowing through the exhaust pipe, wherein the particle measuring system includes a laser beam irradiator, a scattered light detector and a beam stopper, the laser beam irradiator is provided to emit the laser beam so as to pass through the part having the high density of the particles included in the exhaust gas exhausted on a wall side of the exhaust pipe away from the center point in a cross section of the exhaust pipe, and the scattered light detector is provided in a direction substantially orthogonal to the irradiation direction of the laser beam.

25. The processing apparatus according to claim 24, wherein the scattered light detector of the particle measuring system is provided to direct a detection direction to a part having a high density of the particles included in the exhaust gas exhausted in the exhaust pipe.

26. The processing apparatus according to claim 24, wherein the laser beam irradiator of the particle measuring system has a semiconductor laser.

27. The processing apparatus according to claim 24, wherein the particle measuring system is attached to a manifold.

28. The processing apparatus according to claim 24, wherein the particle measuring system is attached to an exhaust pipe of a vacuum exhaust system provided in a vacuum room comprised in any one of a film-forming system, etching system and annealing system.

29. The processing apparatus according to claim 24, wherein the laser beam irradiator of the particle measuring system is provided in a position away from a central axis of the processing chamber to direct a detection direction to the part having the high density of the particles included in the exhaust gas exhausted in the exhaust pipe.

30. The processing apparatus according to claim 24, wherein an attachment position on the exhaust pipe of the particle measuring system is determined as a position where the density of the particles included in the exhaust gas in the exhaust pipe is variable at a minimal distance to the processing chamber where light generated in the processing chamber does not reach.

31. A processing apparatus for processing a substrate, comprising:

a processing chamber into which the substrate is transferred;

an exhaust pump which exhausts an atmosphere or gas from the processing chamber, an exhaust pipe connecting the processing chamber and the exhaust pump; and a particle measuring system, which is attached to the exhaust pipe and detects particles included in an exhaust gas flowing through the exhaust pipe, wherein the particle measuring system includes a laser beam irradiator, a pattered light detector and a beam stopper, the laser beam irradiator is provided to emit the laser beam so as to pass trough the part having the high density of the particles included in the exhaust gas exhausted on a wall side of the exhaust pipe away from the center point in a cross section of the exhaust pipe, the scattered light detector is provided in a direction substantially orthogonal to the irradiation direction of the laser beam, and an attachment position on the exhaust pipe of the particle measuring system is determined as a position where the density of the particles included in the exhaust gas in the exhaust pipe is variable at a minimal distance to the processing chamber where light generated in the processing chamber does not reach.

32. The processing apparatus according to claim 31, wherein the scattered light detector of the particle measuring system is provided to direct a detection direction to a part having a high density of the particles included in the exhaust gas exhausted in the exhaust pipe.

33. The processing apparatus according to claim 31, wherein the laser beam irradiator of the particle measuring system has a semiconductor laser.

34. The processing apparatus according to claim 31, wherein the particle measuring system is attached to a manifold.

35. The processing apparatus according to claim 31, wherein the particle measuring system is attached to an exhaust pipe of a vacuum exhaust system provided in a vacuum room comprised in any one of a film-forming system, etching system and annealing system.

36. The processing apparatus according to claim 31, wherein the laser beam irradiator of the particle measuring system is provided in a position away from a central axis of the processing chamber to direct a detection direction to the part having the high density of the particles included in the exhaust gas exhausted in the exhaust pipe.

* * * * *